US012583928B2

(12) United States Patent
Lickert

(10) Patent No.: US 12,583,928 B2
(45) Date of Patent: Mar. 24, 2026

(54) ANTIBODIES AGAINST IGFR-LIKE RECEPTOR AND USES THEREOF

(71) Applicant: Helmholtz Zentrum München - Deutsches Forschungszentrum Für Gesundheit Und Umwelt (GmbH), Neuherberg (DE)

(72) Inventor: Heiko Lickert, Munich (DE)

(73) Assignee: Helmholtz Zentrum München—Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 1036 days.

(21) Appl. No.: 17/679,545

(22) Filed: Feb. 24, 2022

(65) Prior Publication Data

US 2023/0025525 A1 Jan. 26, 2023

Related U.S. Application Data

(63) Continuation-in-part of application No. 15/757,568, filed as application No. PCT/EP2016/071126 on Sep. 7, 2016, now abandoned.

(30) Foreign Application Priority Data

Sep. 7, 2015 (LU) .......................................... 92818

(51) Int. Cl.

| | |
|---|---|
| ***C07K 16/28*** | (2006.01) |
| ***A61K 39/00*** | (2006.01) |
| ***C07K 16/06*** | (2006.01) |
| ***G01N 33/53*** | (2006.01) |

(52) U.S. Cl.

CPC ........ *C07K 16/2863* (2013.01); *C07K 16/065* (2013.01); *G01N 33/53* (2013.01); *A61K 2039/505* (2013.01); *C07K 2317/24* (2013.01); *C07K 2317/34* (2013.01); *C07K 2317/565* (2013.01); *C07K 2317/76* (2013.01); *G01N 2800/042* (2013.01)

(58) Field of Classification Search

CPC .............. C07K 16/2863; C07K 16/065; C07K 2317/24; G01N 33/53; G01N 2800/042; A61K 2039/505

See application file for complete search history.

(56) References Cited

U.S. PATENT DOCUMENTS

2003/0017563 A1 1/2003 Baker et al.

FOREIGN PATENT DOCUMENTS

| | | | |
|---|---|---|---|
| JP | 2015518704 A | 7/2015 | |
| WO | 2007005987 A2 | 1/2007 | |
| WO | WO2013151663 | * 10/2013 | ............... C12N 9/10 |

OTHER PUBLICATIONS

G. Proetzel and H. Ebersbach, eds. Antibody methods and protocols, Humana Press, ISBN 978-1-61779-930-3, 2012. (Year: 2012).*

Altschul et al. (1997) “Gapped BLAST and PSI-BLAST: A new generation of protein database search programs”, Nucleic Acids Research, 25(17):3389-3402.

Arnaldez et al. (2012) “Targeting the insulin growth factor receptor 1”, Hematology/Oncology Clinics of North America, 26(3):527-542.

B6.BKS(D)-Lepr-db/J, Stock No. 000697, Congenic Mice, product document;The Jackson Laboratory, May 22, 2019, 4 pages.

Boerner et al. (1991) “Production of antigen-specific human monoclonal antibodies from in vitro-primed human splenocytes”, The Journal of Immunology, 147(1):86-95.

Chang et al. (2004) “Insulin signaling and the regulation of glucose transport”, Molecular Medicine, 10(7-12):65-71.

First Office Action received in Chinese Patent Application No. 201680051667.1, mailed on Nov. 23, 2020, 1 Page.

Hameed et al. (2015) “Type 2 diabetes mellitus: from a metabolic disorder to an inflammatory condition”, World Journal of Diabetes, 6(4):598-612.

Hoogenboom et al. (1992) “By-passing immunisation: human antibodies from synthetic repertoires of germline VH gene segments rearranged in vitro”, Journal of Molecular Biology, 227(2):381-388.

Kulkarni et al. (1999) “Tissue-Specific knockout of the insulin receptor in pancreatic β cells creates an insulin secretory defect similar to that in type 2 diabetes”, Cell, 96(3):329-339.

Li et al. (2006) “Human antibodies for immunotherapy development generated via a human B cell hybridoma technology”, Proceedings of the National Academy of Sciences of USA, 103(10):3557-3562.

Lloyd et al. (2009) “Modelling the human immune response: performance of a 1011 human antibody repertoire against a broad panel of therapeutically relevant antigens”, Protein Engineering, Design & Selection, 22(3):159-168.

Marks et al. (1991) “By-passing immunization. Human antibodies from V-gene libraries displayed on phage”, Journal of Molecular Biology, 222(3):581-597.

Notification of Reasons for Rejection received in Japanese Patent Application No. 2018-512274, mailed on Jul. 21, 2020, 7 pages.

International Search Report and Written Opinion received in PCT Application No. PCT/EP2016/071126, mailed on Dec. 2, 2016, 23 pages.

Pollak, Michael (2012) “The insulin and insulin-like growth factor receptor family in neoplasia: An update”, Nature Reviews Cancer, 12(3):159-169.

(Continued)

*Primary Examiner* — Elly-Gerald Stoica

(74) *Attorney, Agent, or Firm* — Kagan Binder, PLLC

(57) ABSTRACT

The present invention provides a novel IGFR-like receptor and antagonists and agonists for targeting said receptor. Said antagonists and agonists are envisaged for use as a medicament, and in particular for treatment of diabetes.

15 Claims, 37 Drawing Sheets

(14 of 37 Drawing Sheet(s) Filed in Color)

Specification includes a Sequence Listing.

(56) References Cited

OTHER PUBLICATIONS

Sarfstein et al. (2013) "Mini review: Nuclear insulin and insulin-like growth factor-1 receptors: A novel paradigm in signal transduction", Endocrinology, 154(5):1672-1679.

Siddle, Kenneth (2011) "Signalling by insulin and IGF receptors: supporting acts and new players", Journal of Molecular Endocrinology, 47(1):R1-R10.

Srivastava et al. (1998) "Trends in pharmacological sciences", Elsevier, Haywarth, GB, 19(6):205-209.

Ueki et al. (2006) "Total insulin and IGF-1 resistance in pancreatic β cells causes overt diabetes", Nature Genetics, 38(5):583-588.

Van Dijk et al. (2001) "Human antibodies as next generation therapeutics", Current Opinion in Chemical Biology, 5(4):368-374.

* cited by examiner

Figure 1

SEQ ID No. 1 (IGFR-like receptor)

```
10         20         30         40         50
MAEPGHSHHL SARVRGRTER RIPRLWRLLL WAGTAFQVTQ GTGPELHACK
        60         70         80         90        100
ESEYHYEYTA CDSTGSRWRV AVPHTPGLCT SLPDPIKGTE CSFSCNAGEF
       110        120        130        140        150
LDMKDQSCKP CAEGRYSLGT GIRFDEWDEL PHGFASLSAN MELDDSAAES
       160        170        180        190        200
TGNCTSSKWV PRGDYIASNT DECTATLMYA VNLKQSGTVN FEYYYPDSSI
       210        220        230        240        250
IFEFFVQNDQ CQPNADDSRW MKTTEKGWEF HSVELNRGNN VLYWRTTAFS
       260        270        280        290        300
VWTKVPKPVL VRNIAITGVA YTSECFPCKP GTYADKQGSS FCKLCPANSY
       310        320        330        340        350
SNKGETSCHQ CDPDKYSEKG SSSCNVRPAC TDKDYFYTHT ACDANGETQL
       360        370        380        390        400
MYKWAKPKIC SEDLEGAVKL PASGVKTHCP PCNPGFFKTN NSTCQPCPYG
       410        420        430        440        450
SYSNGSDCTR CPAGTEPAVG FEYKWWNTLP TNMETTVLSG INFEYKGMTG
       460        470        480        490        500
WEVAGDHIYT AAGASDNDFM ILTLVVPGFR PPQSVMADTE NKEVARITFV
       510        520        530        540        550
FETLCSVNCE LYFMVGVNSR TNTPVETWKG SKGKQSYTYI IEENTTTSFT
       560        570        580        590        600
WAFQRTTFHE ASRKYTNDVA KIYSINVTNV MNGVASYCRP CALEASDVGS
       610        620        630        640        650
SCTSCPAGYY IDRDSGTCHS CPTNTILKAH QPYGVQACVP CGPGTKNNKI
       660        670        680        690        700
HSLCYNDCTF SRNTPTRTFN YNFSALANTV TLAGGPSFTS KGLKYFHHFT
       710        720        730        740        750
LSLCGNQGRK MSVCTDNVTD LRIPEGESGF SKSITAYVCQ AVIIPPEVTG
       760        770        780        790        800
YKAGVSSQPV SLADRLIGVT TDMTLDGITS PAELFHLESL GIPDVIFFYR
       810        820        830        840        850
SNDVTQSCSS GRSTTIRVRC SPQKTVPGSL LLPGTCSDGT CDGCNFHFLW
       860        870        880        890        900
ESAAACPLCS VADYHAIVSS CVAGIQKTTY VWREPKLCSG GISLPEQRVT
       910        920        930        940        950
ICKTIDFWLK VGISAGTCTA ILLTVLTCYF WKKNQKLEYK YSKLVMNATL
       960        970        980        990       1000
KDCDLPAADS CAIMEGEDVE DDLIFTSKKS LFGKIKSFTS KRTPDGFDSV
      1010
PLKTSSGGLD MDL
```

Figure 1 (continued)

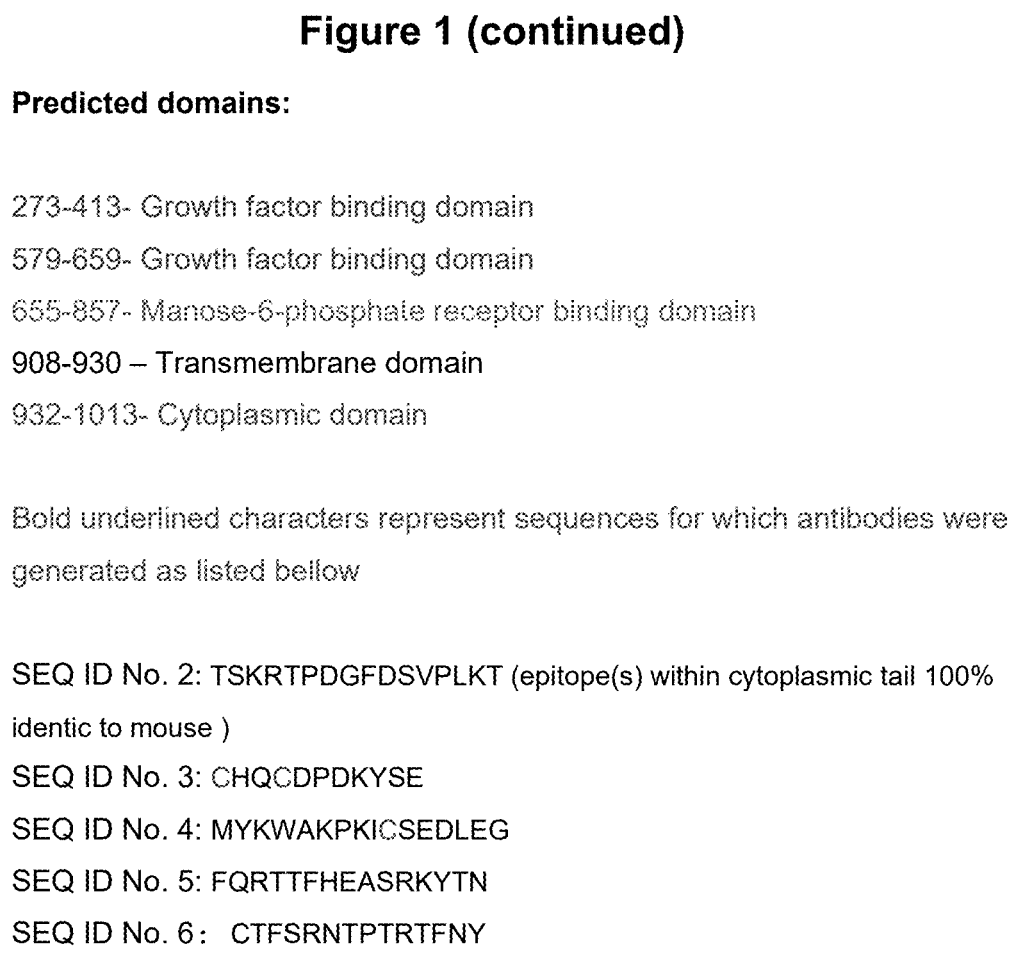

Predicted domains:

273-413- Growth factor binding domain 579-659- Growth factor binding domain 655-857- Manose-6-phosphate receptor binding domain 908-930 – Transmembrane domain 932-1013- Cytoplasmic domain Bold underlined characters represent sequences for which antibodies were generated as listed bellow SEQ ID No. 2: TSKRTPDGFDSVPLKT (epitope(s) within cytoplasmic tail 100% identic to mouse )

SEQ ID No. 3: CHQCDPDKYSE

SEQ ID No. 4: MYKWAKPKICSEDLEG

SEQ ID No. 5: FQRTTFHEASRKYTN

SEQ ID No. 6 : CTFSRNTPTRTFNY

Figure 3
A
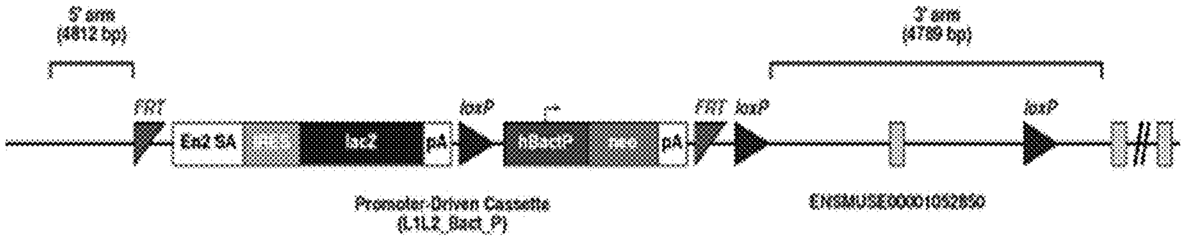
B
CD1 Background
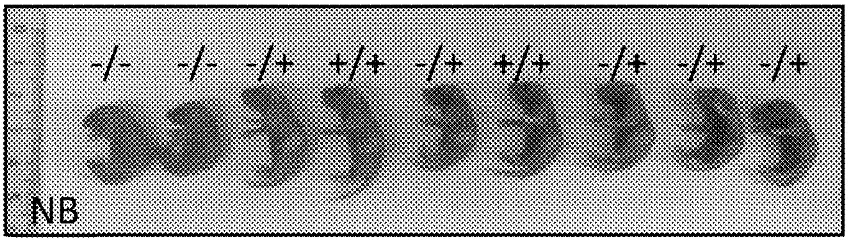
C
Embryos/pups
| | +/+ (%) | +/- (%) | -/- (%) |
|---|---|---|---|
| E14.5 | 3 (17.6%) | 7 (41.1%) | 7 (41.1%) |
| E16.5 | 8 (34.7%) | 8 (34.7%) | 7 (30.4%) |
| E18.5 | 5 (20.8%) | 15(62.5%) | 4 (16.6%) |
| P1 | 12 (24.4%) | 20 (40.8%) | 17 (34.6%) |
| P2 | 3 (21.4%) | 11 (78.5%) | 0 (0) |
| 3weeks | 62 (36.68%) | 101 (59.76%) | 6 (3.55%) |
D
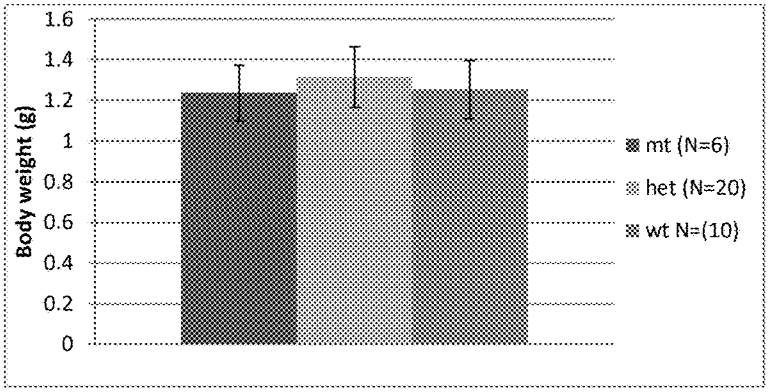

Min6 starvation assay time course

(HBSS 0mM Glc and 0.2% BSA)

IGF-3R

TMD-KKNQKLEYKYSKLVMNATLKDCDLPAADSCAIMEGEDVEDDLIFTSKKSLFGKIKSFTSKRTPDGFDSVPLKTSSGGLDMDL SEQ ID NO: 10

YxxΦ (where Phi can be F, I, L, M or V) recongnized by μ2 subunit of AP-2 SEQ ID NO: 11

NX_A8MWY0-1 UPF0577 protein KIAA1324-like *(KIAA1324L)* [NX_A8MWY0-1]

1029aa 58% 257 4.2e-23 score 103.6 bits (257), identities 48/74, positives 61/74, gaps 0/74

Fragment of SEQ ID NO: 1

```
query     1 KKNQKLEYKYSKLVMNATLKDCDLPAADSCAIMEGEDVEDDLIFTSKKSLFGKIKSFTSKRTPDGFDSVPLKTS    74
              KKNQKLEYKYSKLVM    K+C+LPAADSCAIMEGED E+++++++K+SL GK+KS  +K   D F+SV LKTS
subject 951 KKNQKLEYKYSKLVMTTNSKECELPAADSCAIMEGEDNEEEVVYSNKQSLLGKLKSLATKEKEDHFESVQLKTS  1024
```

942 S → F ; COSMIC: 527241

942 S → C ; COSMIC: 1472378

SEQ ID NO: 12

Interaction with AP-2 under starvation conditions

| Identifier | Position on gene | Length | Coding for Iso 1 ENST00000369939 | Coding for Iso 3 ENST00000529753 |
|---|---|---|---|---|
| ENSE00002163328 | 323 - 658 | 336 | Met 1 - Glu 51 | |
| ENSE00002142416 | 477 - 658 | 182 | | Met 1 - Glu 51 |
| ENSE00003470284 | 48216 - 48336 | 121 | Ser 52 - Ser 92 | Ser 52 - Ser 92 |
| ENSE00003686523 | 50821 - 51013 | 193 | Ser 92 - Ser 156 | Ser 92 - Ser 156 |
| ENSE00003539220 | 58188 - 58335 | 148 | Ser 156 - Phe 205 | Ser 156 - Phe 205 |
| ENSE00003644627 | 58810 - 58890 | 81 | Val 206 - Ser 232 | Val 206 - Ser 232 |
| ENSE00001665257 | 59796 - 59879 | 84 | | Val 233 - Leu 260 |
| ENSE00003585024 | 59796 - 59901 | 106 | Val 233 - Gly 268 | |
| ENSE00003687030 | 60010 - 60159 | 150 | Gly 268 - Glu 318 | |
| ENSE00003491577 | 71367 - 71455 | 89 | Glu 318 - Glu 347 | |
| ENSE00003581990 | 74499 - 74676 | 178 | Thr 348 - Asp 407 | Thr 261 - Asp 320 |
| ENSE00003585444 | 75388 - 75516 | 129 | Asp 407 - Gly 450 | Asp 320 - Gly 363 |
| ENSE00003567810 | 75914 - 76004 | 91 | Gly 450 - Arg 480 | Gly 363 - Arg 393 |
| ENSE00003505690 | 77688 - 77793 | 106 | Arg 480 - Val 515 | Arg 393 - Val 428 |
| ENSE00003605994 | 78048 - 78185 | 138 | Gly 516 - Ala 561 | Gly 429 - Ala 474 |
| ENSE00003603237 | 78933 - 79196 | 264 | Ser 562 - Lys 649 | Ser 475 - Lys 562 |
| ENSE00003468515 | 80743 - 80916 | 174 | Ile 650 - Gln 707 | Ile 563 - Gln 620 |
| ENSE00003538222 | 83796 - 83976 | 181 | Gly 708 - Gly 768 | Gly 621 - Gly 681 |
| ENSE00003469577 | 84301 - 84397 | 97 | Gly 768 - Arg 800 | Gly 681 - Arg 713 |
| ENSE00003558615 | 84895 - 84996 | 102 | Arg 800 - Gly 834 | Arg 713 - Gly 747 |
| ENSE00003626838 | 86176 - 86302 | 127 | Gly 834 - Gln 876 | Gly 747 - Gln 789 |
| ENSE00003467882 | 86381 - 86559 | 179 | Lys 877 - Lys 936 | Lys 790 - Lys 849 |
| ENSE00003650058 | 87057 - 87222 | 166 | Lys 936 - Lys 991 | Lys 849 - Lys 904 |
| ENSE00002151239 | 89266 - 89427 | 162 | | Arg 905 - Leu 926 |
| ENSE00001451285 | 89266 - 89551 | 286 | Arg 992 - Leu 1013 | |

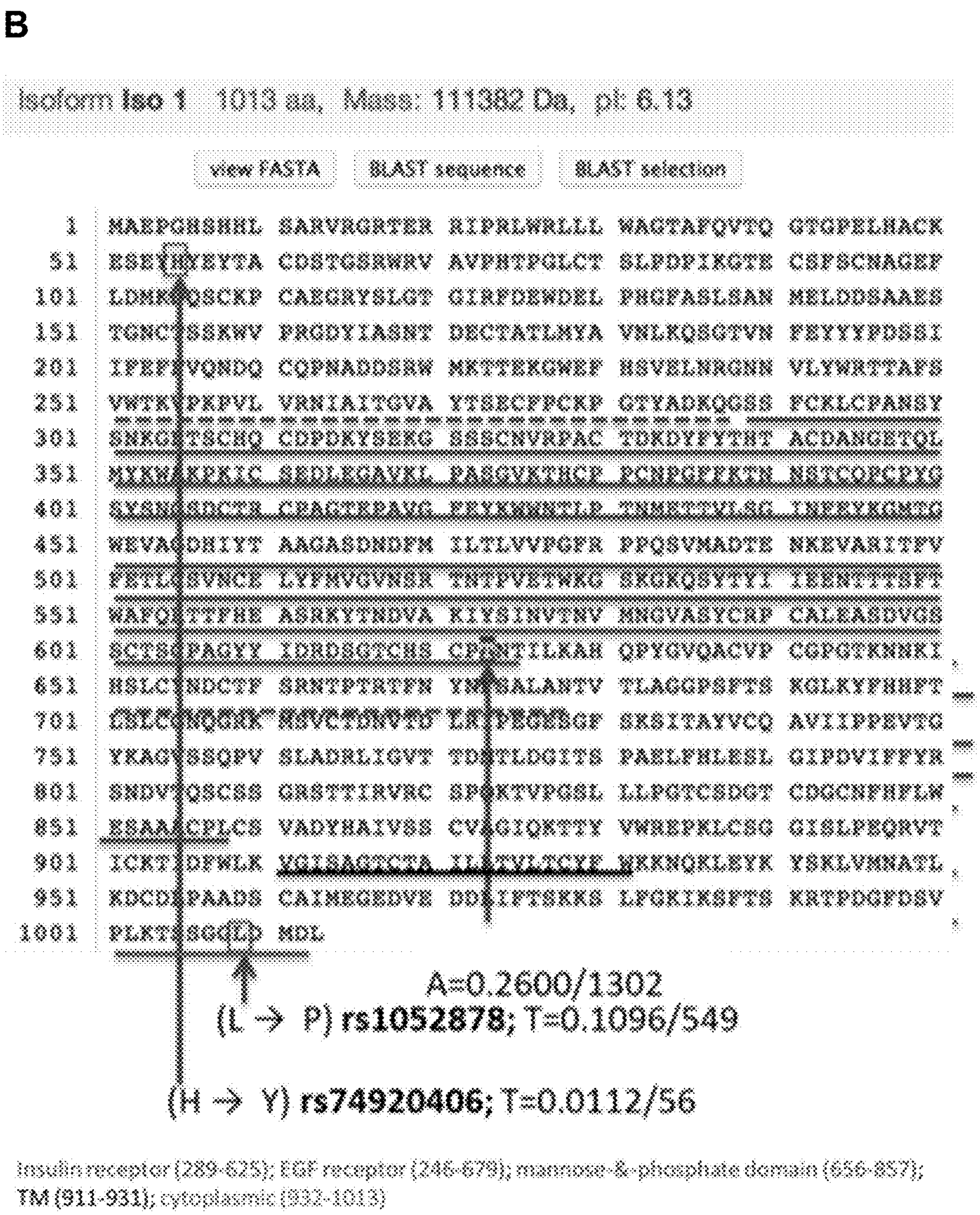

B

Isoform Iso 1 1013 aa, Mass: 111382 Da, pI: 6.13 view FASTA | BLAST sequence | BLAST selection

```
   1 MAEPGHSHHL SARVRGRTER RIPRLWRLLL WAGTAFQVTQ GTGPELHACK
  51 ESEYHYEYTA CDSTGSRWRV AVPHTPGLCT SLPDPIKGTE CSFSCNAGEF
 101 LDMK[illegible]QSCKP CAEGRYSLGT GIRFDEWDEL PHGFASLSAN MELDDSAAES
 151 TGNC[illegible]SSKWV PRGDYIASNT DECTATLMYA VNLKQSGTVN FEYYYPDSSI
 201 IFEF[illegible]VQNDQ CQPNADDSRW MKTTEKGWEF HSVELNRGNN VLYWRTTAFS
 251 VWTK[illegible]PKPVL VRNIAITGVA YTSECFPCKP GTYADKQGSS FCKLCPANSY
 301 SNKG[illegible]TSCHQ CDPDKYSEKG SSSCNVRPAC TDKDYFYTHT ACDANGETQL
 351 MYKW[illegible]KPKIC SEDLEGAVKL PASGVKTHCP PCNPGFFKTN NSTCQPCPYG
 401 SYSN[illegible]SDCTR CPAGTEPAVG FEYKWWNTLP TNMETTVLSG INFEYKGMTG
 451 WEVA[illegible]DHIYT AAGASDNDFM ILTLVVPGFR PPQSVMADTE NKEVARITFV
 501 FETL[illegible]SVNCE LYFMVGVNSR TNTPVETWKG SKGKQSYTYI IEENTTTSFT
 551 WAFQ[illegible]TTFHE ASRKYTNDVA KIYSINVTNV MNGVASYCRP CALEASDVGS
 601 SCTS[illegible]PAGYY IDRDSGTCHS CP[illegible]NTILKAH QPYGVQACVP CGPGTKNNKI
 651 HSLC[illegible]NDCTF SRNTPTRTFN YN[illegible]SALANTV TLAGGPSFTS KGLKYFHHFT
 701 [illegible] SKSITAYVCQ AVIIPPEVTG
 751 YKAG[illegible]SSQPV SLADRLIGVT TD[illegible]TLDGITS PAELFHLESL GIPDVIFFYR
 801 SNDV[illegible]QSCSS GRSTTIRVRC SP[illegible]KTVPGSL LLPGTCSDGT CDGCNFHFLW
 851 ESAA[illegible]CPLCS VADYHAIVSS CV[illegible]GIQKTTY VWREPKLCSG GISLPEQRVT
 901 ICKT[illegible]DFWLK VGISAGTCTA IL[illegible]TVLTCYF WKKNQKLEYK YSKLVMNATL
 951 KDCD[illegible]PAADS CAINEGEDVE DD[illegible]IFTSKKS LFGKIKSFTS KRTPDGFDSV
1001 PLKT[illegible]SGGLD MDL
```

A=0.2600/1302

(L → P) rs1052878; T=0.1096/549

(H → Y) rs74920406; T=0.0112/56

Insulin receptor (289-625); EGF receptor (246-679); mannose-6-phosphate domain (656-857); TM (911-931); cytoplasmic (932-1013)

C

C

| Variant | Chrom | Position | Protein Consequence | Filter | Annotation | Allele Count | Allele Number | Number of Homozygotes | Allele Frequency |
|---|---|---|---|---|---|---|---|---|---|
| 1:109704525 C / T (rs74920406) | 1 | 109704525 | p.His55Tyr | PASS | missense | 3351 | 120426 | 69 | 0.02783 |
| 1:109735416 A / C (rs659543) | 1 | 109735416 | p.Thr623Pro | PASS | missense | 94935 | 121258 | 38276 | 0.7829 |
| 1:109735416 A / G (rs659543) | 1 | 109735416 | p.Thr623Ala | PASS | missense | 1 | 121258 | 0 | 0.000008247 |
| 1:109745618 T / C (rs1052878) | 1 | 109745618 | p.Leu1009Pro | PASS | missense | 109914 | 121366 | 49957 | 0.9056 |

**Table. Associations of *KIAA1324* tagging SNPs with insulin sensitivity ($N_{OGTT}$=2,223; $N_{Clamp}$=502)**

| | Genotype | N OGTT | Insulin, fasting (pmol/L) | HOMA-IR ($10^{-6}$ mol*U*$L^{-2}$) | ISI, OGTT ($10^{19}$ $L^{2}$*$mol^{-2}$) | N Clamp | ISI, Clamp ($10^{6}$ L*$kg^{-1}$*$min^{-1}$) |
|---|---|---|---|---|---|---|---|
| Rs74920406 | CC | 2,038 | 81.6 ±72.2 | 3.21 ±3.07 | 13.7 ±9.8 | 460 | 0.086 ±0.052 |
| | CT | 182 | 75.8 ±59.2 | 2.97 ±2.48 | 12.7 ±8.1 | 42 | 0.082 ±0.059 |
| | TT | 3 | 72.3 ±16.3 | 2.75 ±0.77 | 11.8 ±6.0 | - | - |
| $p_{Association}$ | - | - | 0.7 | 0.7 | 0.5 | - | 0.5 |
| $p_{Gender\ interaction}$ | - | - | 0.4 | 0.5 | 0.5 | - | - |
| Rs659543 | GG | 1,267 | 80.6 ±70.8 | 3.17 ±2.97 | 13.7 ±9.7 | 296 | 0.087 ±0.052 |
| | GT | 828 | 81.9 ±73.1 | 3.22 ±3.17 | 13.7 ±9.9 | 184 | 0.086 ±0.055 |
| | TT | 128 | 80.2 ±61.8 | 3.12 ±2.53 | 12.3 ±7.5 | 22 | 0.073 ±0.037 |
| $p_{Association}$ | - | - | **0.0292** | **0.0364** | 0.06 | - | 0.6 |
| $p_{Gender\ interaction}$ | - | - | 0.5 | 0.6 | 0.8 | - | - |
| Rs1052878 | CC | 1,793 | 80.6 ±69.6 | 3.17 ±2.95 | 13.7 ±9.6 | 402 | 0.086 ±0.052 |
| | CT | 408 | 83.0 ±78.0 | 3.27 ±3.36 | 13.6 ±9.9 | 96 | 0.084 ±0.053 |
| | TT | 22 | 83.0 ±65.3 | 3.20 ±2.53 | 13.3 ±8.7 | 4 | 0.104 ±0.065 |
| $p_{Association}$ | - | - | 0.8 | 0.9 | 0.9 | - | 0.9 |
| $p_{Gender\ interaction}$ | - | - | 0.1 | 0.2 | 0.2 | - | - |

Metabolic data are shown as unadjusted raw data (means ±SD). Associations between SNP genotypes and insulin sensitivity were tested by multiple linear regression analyses (standard least squares method) with gender, age, and BMI as covariates. For SNP-gender interaction analysis, cross effects on insulin sensitivity were tested by multiple linear regression analyses with age and BMI as covariates. $p_{Association}$ – p-value for association between SNP and insulin sensitivity (additive inheritance model); $p_{Gender\ interaction}$ – p-value for interaction effect between SNP and gender on insulin sensitivity. Nominal associations ($p<0.05$) are marked by using bold fonts, significant associations ($p<0.0170$ after Bonferroni correction for 3 SNPs) by using bold fonts and underlining. BMI – body mass index; HOMA-IR – homeostasis model assessment of insulin resistance; ISI – insulin sensitivity index; OGTT – oral glucose tolerance test; SNP – single nucleotide polymorphism

Table. Associations of *KIAA1324* tagging SNPs with adipokines and inflammatory traits ($N_{Leukos/CRP}$=2,198; $N_{Cytokines}$=470; $N_{Adipokines}$=1,304)

| | Genotype | N Leukos/CRP | Leukocytes ($\mu l^{-1}$) | CRP (mg/dL) | N Cytokines | IL-6 (pg/mL) | TNF-α (pg/mL) | N Adipokines | Leptin (ng/mL) | Adiponectin (μg/mL) |
|---|---|---|---|---|---|---|---|---|---|---|
| Rs74920406 | CC | 2,020 | 6,650 ±1,942 | 0.397 ±0.547 | 431 | 0.871 ±0.817 | 2.91 ±5.59 | 1,193 | 28.8 ±33.3 | 14.4 ±7.5 |
| | CT | 175 | 6,474 ±1,754 | 0.375 ±0.466 | 38 | 0.804 ±0.614 | 1.66 ±1.78 | 110 | 33.9 ±33.5 | 14.8 ±7.3 |
| | TT | 3 | 7,287 ±2,454 | 0.713 ±0.548 | 1 | 2.550 | 1.87 | 1 | 44.6 | 8.0 |
| $p_{Association}$ | - | - | 0.6 | 0.7 | - | 0.5 | 0.07 | - | **0.0159** | 0.4 |
| $p_{Gender\ interaction}$ | - | - | 0.6 | 0.06 | - | - | - | - | 0.5 | 0.9 |
| Rs659543 | GG | 1,250 | 6,673 ±1,936 | 0.407 ±0.561 | 274 | 0.886 ±0.821 | 2.95 ±5.69 | 742 | 29.2 ±32.7 | 14.5 ±7.6 |
| | GT | 821 | 6,562 ±1,902 | 0.381 ±0.523 | 167 | 0.786 ±0.675 | 2.73 ±5.28 | 485 | 29.3 ±34.6 | 14.4 ±7.4 |
| | TT | 127 | 6,772 ±2,012 | 0.374 ±0.442 | 29 | 1.195 ±1.190 | 2.02 ±2.15 | 77 | 28.7 ±31.7 | 14.4 ±6.7 |
| $p_{Association}$ | - | - | 0.8 (♀ 0.1, ♂ 0.06) | 0.8 | - | 0.7 | 0.4 | - | 0.8 (♀ 0.2, ♂ 0.0293) | 0.6 |
| $p_{Gender\ interaction}$ | - | - | **0.0181** | 0.4 | - | - | - | - | **0.0438** | 0.9 |
| Rs1052878 | CC | 1,767 | 6,626 ±1,932 | 0.397 ±0.553 | 377 | 0.860 ±0.771 | 2.81 ±5.52 | 1,045 | 28.6 ±32.9 | 14.4 ±7.5 |
| | CT | 409 | 6,660 ±1,903 | 0.390 ±0.496 | 89 | 0.909 ±0.934 | 2.82 ±4.93 | 243 | 31.3 ±35.1 | 14.4 ±7.4 |
| | TT | 22 | 7,111 ±2,091 | 0.360 ±0.377 | 4 | 0.943 ±1.063 | 2.69 ±2.85 | 16 | 34.4 ±38.1 | 15.7 ±7.9 |
| $p_{Association}$ | - | - | 0.8 | 0.9 | - | 0.9 | 0.6 | - | 0.6 | 0.8 |
| $p_{Gender\ interaction}$ | - | - | 0.5 | 0.1 | - | - | - | - | 1.0 | 0.5 |

Data are shown as unadjusted raw data (means ±SD). Associations between SNP genotypes and adipokines/inflammatory parameters were tested by multiple linear regression analyses (standard least squares method) with gender, age, and BMI as covariates. For SNP-gender interaction analysis, cross effects on adipokines/inflammatory parameters were tested by multiple linear regression analyses with age and BMI as covariates. $p_{Association}$ – p-value for association between SNP and adipokines/inflammatory parameters (additive inheritance model); $p_{Gender\ interaction}$ – p-value for interaction effect between SNP and gender on adipokines/inflammatory parameters. Nominal associations (p<0.05) are marked by using bold fonts, significant associations (p<0.0170 after Bonferroni correction for 3 SNPs) by using bold fonts and underlining. BMI – body mass index; CRP – C-reactive protein; IL – interleukin; MCP – monocyte chemoattractant protein; SNP – single nucleotide polymorphism; TNF – tumor necrosis factor

Table. Associations of *KIAA1324* tagging SNPs with proinsulin conversion ($N_{OGTT}$=2,036)

| | Genotype | N OGTT | Proinsulin/insulin, fasting | Proinsulin/insulin, 30 min | $AUC_{0-120\ min}$ Proinsulin/ $AUC_{0-120\ min}$ Insulin |
|---|---|---|---|---|---|
| Rs74920406 | CC | 1,861 | 0.100 ±0.139 | 0.026 ±0.028 | 0.041 ±0.035 |
| | CT | 172 | 0.087 ±0.088 | 0.021 ±0.016 | 0.035 ±0.026 |
| | TT | 3 | 0.037 ±0.023 | 0.014 ±0.011 | 0.021 ±0.013 |
| $P_{Association}$ | - | - | 0.2 | **0.0112** | **0.0432** |
| $P_{Gender\ interaction}$ | - | - | 0.6 | 0.7 | 0.7 |
| $P_{BMI\ interaction}$ | - | - | 0.8 | 0.5 | 0.5 |
| $P_{IS\ interaction}$ | - | - | 0.9 | 0.5 | 0.4 |
| $P_{Glucose\ interaction}$ | - | - | 0.3 | 0.3 | 0.2 |
| Rs659543 | GG | 1,159 | 0.097 ±0.133 | 0.026 ±0.025 | 0.041 ±0.035 |
| | GT | 758 | 0.101 ±0.143 | 0.026 ±0.031 | 0.039 ±0.034 |
| | TT | 119 | 0.101 ±0.112 | 0.026 ±0.017 | 0.043 ±0.033 |
| $P_{Association}$ | - | - | 0.3 | 0.5 | 0.6 |
| $P_{Gender\ interaction}$ | - | - | 0.2 | 0.4 | 0.2 |
| $P_{BMI\ interaction}$ | - | - | 0.4 | 0.5 | 0.4 |
| $P_{IS\ interaction}$ | - | - | 0.7 | 0.4 | 0.9 |
| $P_{Glucose\ interaction}$ | - | - | 0.7 | 0.4 | 0.9 |
| Rs1052878 | CC | 1,640 | 0.098 ±0.136 | 0.025 ±0.025 | 0.040 ±0.034 |
| | CT | 375 | 0.100 ±0.138 | 0.028 ±0.034 | 0.043 ±0.036 |
| | TT | 21 | 0.101 ±0.089 | 0.022 ±0.016 | 0.037 ±0.027 |
| $P_{Association}$ | - | - | 0.4 (♀ 0.7, ♂ 0.0282) | 0.3 | 0.1 (♀ 0.9, ♂ 0.0103) |
| $P_{Gender\ interaction}$ | - | - | **0.0490** | 0.06 | **0.0463** |
| $P_{BMI\ interaction}$ | - | - | 0.8 | 0.3 | 0.3 |
| $P_{IS\ interaction}$ | - | - | 0.4 | 0.4 | 0.5 |
| $P_{Glucose\ interaction}$ | - | - | 0.7 | 0.2 | 0.4 |

Non Diabetic

Diabetic

Strategy to generate IGFR-I knock-out and knock-in Venus fusion
1
Knock-out
20,000
20,100
20,200
5'upstream seq
exon 1
5'UTR
START
2
Venus Knock-in
98,000
99,000
100,000
101,000
102,000
103,000
Venus
Neo
exon 22
exon 22
bGHpA
PGK promotor
RGS-His Tag
FRT
EM7
Overlap with Neo
3'UTR
STOP Wild-type Min6 clones (x8)

A. Genomic PCR for IGFR-I WT and knock-out Min6 clones
B5-WT
B6-WT
B7-WT
B8-WT
B9-WT
B10-WT
B11-WT
B12-WT
H5-KO
F9-KO
B3-KO
E10-KO
C5-KO
E5-KO
G9-KO
E8-KO
D5-KO
H3-KO
G11-KO
H2-KO
A7-KO
500bp
400bp
300bp
200bp
100bp
395bp
356bp
B. Western blot for IGFR-I WT and knock-out Min6 clones
Parental
B5-WT
B6-WT
B7-WT
B8-WT
B9-WT
B10-WT
H3-KO
A7-KO
B3-KO
B11-WT
B12-WT
Parental
C5-KO
D5-KO
E5-KO
E8-KO
E10-KO
H9-KO
G9-KO
G11-KO
H2-KO
H5-KO

Min6 IGFR-I (C22Rik) knock-out show increase AMPK and Insulin receptor activation in growth medium

IGFR-I-Venus fusion knock-in Min6 cell line

Homo- and hetero-dimerization via CRD and TM growth factor receptor CRD

M6P

TM

Venus

IGFR-I

GFP

Golgi

Merged

IGFR-I is strongly upregulated PDX1$^+$/NKX6.1$^+$ endocrine progenitors differentiated from induced pluripotent stem cells (iPSCs)

Rat and mouse abs against peptides B and D of IGFR-I ectodomain used in western blotting EIG-B clones are rat EIG-D clones are mouse IGFR-I SNPs are highly associated with coronary artery disease, LDL cholesterol and type 2 diabetes in GWAS metastudies

IGFR-I SNPs are highly associated with coronary artery disease, LDL cholesterol and type 2 diabetes in GWAS metastudies www.type2diabetesgenetics.com

ANTIBODIES AGAINST IGFR-LIKE RECEPTOR AND USES THEREOF

PRIORITY CLAIM

This application is a continuation-in-part of U.S. patent application Ser. No. 15/757,568, filed Mar. 5, 2018, which claims priority to International Application No. PCT/EP2016/071126, filed Sep. 7, 2016, which claims priority to Luxembourg Application No. 92818, filed Sep. 7, 2015, wherein the contents of said applications are incorporated herein by reference in their entireties. Also, the entire contents of the ASCII text file entitled "IPM0118US2_Sequence_Listing.txt" created on Feb. 23, 2022, and having a size of 36 kilobytes, is incorporated herein by reference.

BACKGROUND

The insulin/insulin-like growth factors (IGFs) constitute a network of ligands, cell-surface receptors, and binding proteins involved in the regulation of multiple physiological and pathological processes. Insulin/IGFs play key developmental and metabolic roles at every stage of life. Insulin/IGF signaling also contributes to regulation of lifespan, while dysregulation of signaling has been implicated in neoplasia. Although the insulin receptor (InsR) and IGF-1 receptor (IGF1R) share the majority of their downstream cytoplasmic mediators, most experimental and clinical evidence is consistent with the notion that InsR activation (mainly by insulin) leads primarily to metabolic activities, whereas IGF1R activation (mainly by IGF-1 or IGF-2) leads to proliferative and differentiative events (Sarfstein R and Werner H Endocrinology. 2013 May; 154(5): 1672-9; Siddle K J Mol Endocrinol. 2011 Jun. 17; 47 (1): R1-10).

InsR and IGF1R belong to a family of transmembrane tyrosine kinase-containing receptors. In their mature form, they present as heterotetramers composed of 2 extracellular α-subunits and 2 transmembrane β-subunits harboring the tyrosine kinase activity. Both IGF- and insulin receptors show a high degree of homology (84% in the tyrosine kinase domain, 45%-65% in the ligand binding domain, and above 50% in overall amino acid sequence). In addition, the receptors display a remarkable similarity in genomic organization (Sarfstein R and Werner H, loc. cit.; Arnalez F and Heiman L. Hematol Oncol Clin North Am. 2012 June; 26(3): 527-42).

There are also "hybrid" receptors composed of half an insulin receptor and half an IGF receptor (IRaβ linked to IGF1Rαβ). Hybrids bind IGFs with similar affinity to IGFR, but bind insulin with substantially lower affinity than InsR. It is unclear whether hybrid receptors have a distinct physiological role (Sarfstein R and Werner H, loc. cit.; Arnalez F and Heiman L., loc. cit).

The insulin receptor exists in two splice variant isoforms as a result of alternative splicing of the sequence encoded by exon 11; the 'B' isoform recognizes only insulin, but the 'A' isoform, which is the isoform that is most commonly expressed by tumours, recognizes both insulin and IGF1 and 2. Both isoforms are differentially expressed during development, with InsR-A predominantly ex-pressed in fetal tissues and InsR-B predominately expressed in adult tissues, particularly liver, muscle, and adipocytes. The IGF1R displays an opposite pattern of expression, being absent in liver and present at low levels in adipose tissue and at high levels in brain. In addition, and consistent with its potent anti-apoptotic, pro-survival role, the IGF1R is overexpressed in most tumors and malignant cells (Pollak M Nat Rev Cancer. 2012 Feb. 16; 12(3): 159-69, Sarfstein R and Werner H, loc. cit.; Siddle K, loc cit).

IGF1 and IGF2 can be expressed in endocrine, paracrine or autocrine manners, the latter being common in transformed cells. The liver is their main site of production. By contrast, insulin production is confined to pancreatic β-cells. Insulin and the IGFs bind with high affinity to their specific receptor and with lower affinity to the non-cognate receptor, with the exception of IGF2, which also binds InsR-A with high affinity (Pollak M, loc cit.; Siddle K, loc. cit.).

Ligand binding induces conformational changes in the structures of the InsR and IGF1R and activates their intrinsic tyrosine kinase activity. Although insulin and IGFs play distinct physiological roles, they utilize the same signaling pathways. Downstream signaling of the InsR and IGF1R is mostly channeled through the MAPK/Ras-Raf-Erk pathway, the phosphatidylinositol-3-kinase/AKT/mTOR (PI3K/AKT) pathway and the Janus kinase/signal transducer and activator of transcription (JAK/STAT) pathway. Ultimately, activation of IGF1R results in increased cell proliferation and decreased apoptosis, whereas activation of the InsR by insulin-binding promotes the storage and synthesis of lipids, protein, and carbohydrates and inhibits their breakdown and release into the circulation. The first step by which insulin increases energy storage or utilization involves the regulated transport of glucose into the cell, mediated by the facilitative glucose transporter Glut4 (Chang et al. Mol Med. 2004 July-December; 10(7-12): 65-71.). Insulin expression is confined to specialized pancreatic β-cells, and under normal circumstances it is tightly regulated by the level of circulating glucose. Insulin-stimulated glucose uptake by classic insulin-sensitive organs (liver, muscle and adipose tissue) reduces circulating glucose levels. The β-cells are thus glucose 'thermostats', sensing glucose and releasing insulin to maintain physiologic glucose levels within a relatively narrow range. Breakdown of the delicately balanced InsR signaling pathways results in an uncontrolled or impaired insulin-secretion, dysregulated blood glucose levels, and eventually to pancreatic β cell destruction or loss-of-function, a condition commonly known as diabetes (Pollak M, loc cit.; Siddle K, loc. cit.; Sarfstein R and Werner H, loc. cit; Arnalez F and Heiman L., loc. cit)

Diabetes mellitus, affecting 8.3% of the adult population of the world and increasing at an alarming rate, is one of the most common diseases of current era. The number of diabetes mellitus patients is projected to increase from 382 million in 2013 to 592 million by 2035, denoting a net increase of 55%. The predominant form is type 2 diabetes (T2D) which accounts for nearly 90% of all diabetes cases (Hameed et al. World J Diabetes. 2015 May 15; 6(4): 598-612).

Type 1 diabetes (T1D) is an autoimmune disorder afflicting millions of people worldwide and occurs as a consequence of the organ-specific immune destruction of the insulin-producing β-cells in the islets of Langerhans within the pancreas. Once those cells are destroyed, patients with type 1 diabetes lose blood glucose control, which can result in both acute conditions (for example, ketoacidosis and severe hypoglycemia) and secondary complications (including heart disease, blindness and kidney failure). Type 1 diabetes is thought to develop as a consequence of a combination of genetic predisposition, largely unknown environmental factors, and stochastic events, however, the precise immunologic, genetic and physiologic events that control disease initiation and progression continue to be elucidated.

Early type 2 diabetes (T2D) is caused by insulin resistance of classic insulin-target organs (i.e. reduced uptake of glucose by normal insulin-target cells, often induced by excess calorific intake) leading to hyperinsulinemia. Initially, these increased levels of insulin are sufficient to overcome insulin resistance and to avoid hyperglycemia. However, hyperglycemia eventually occurs not only because of increasing insulin resistance but also because of decreasing insulin output by pancreatic β-cells.

Controlling blood glucose levels is the major goal of diabetes treatment. T1D is commonly managed with administration of insulin as well as dietary changes and exercise. However, the life-long requirement of insulin injections after nutritional intake may severely reduce quality of life of the patient. Moreover, appropriate dosage and timing of insulin injection can prove difficult. Cure or prevention of T1D is severely impaired by the absence of biomarkers that are reliably correlated with the pathogenic process, resulting in β-cell numbers being markedly reduced at the time of diagnosis. The goal of most clinical trials in type 1 diabetes today is to improve functional residual β-cell mass, optimally through induction of immunologic tolerance, while preserving protective immune responses. By definition, this will rarely "cure" the disease because of the significant β-cell destruction that preceded the treatment. Therefore, reliable biomarkers preferably expressed at disease onset would be highly desirable. Other methods focus on the transplantation of either the pancreas or pancreatic β-cells to reconstitute the insulin-secreting function. However, this technique is hampered by a shortage of donor organs. For T2D, besides insulin, other non-insulin therapeutics including synthetic blood sugar lowering agents are available, which are however often limited in terms of their practical effect, convenience of administration, and may elicit adverse reactions.

The safety concerns and adverse effects of available diabetes therapeutics, as well as the lack of permanent remission of disease with any agent tested to date have heightened interest in specific interventions that might modulate the disease.

It is the object of the invention to comply with the needs in the prior art.

SUMMARY

The present inventors observed that the protein encoded by the human KIAA1324 gene, also known as estrogen-induced gene 121 protein (Q6UXG2), co-localizes with IGF-1R, IGF-2R and InsR, in particular in the pancreas. Estrogen-induced gene 121 protein was assigned a function in regulation of autophagy and in promoting cell survival under stress. A variant protein encoded by the estrogen-induced gene 121 is also known in the art and was designated MABA-1 (WO 2007/005987). MABA-1 differs from the protein encoded by the estrogen-induced gene 121 at one position. MABA-1 was deemed to play a role in cancer, since blocking the protein resulted in growth inhibition of cancer cells. However, nothing was known, let alone speculated about a role of said protein in metabolism. This role was for the first time attributed to said protein by the present inventors.

Due to its domain structure that resembles that of IGFRs, the present inventors assigned to the protein a function of a receptor and thus they called the protein IGFR-like receptor. The present inventors also observed highest expression of their IGFR-like receptor in pituitary gland, hypothalamus and islet cells which constitute the endocrine axis that controls food intake and metabolism.

Furthermore, the present inventors elucidated that either knocking down or knocking-out IGFR-like receptor results in increased phosphorylation of InsR and IGFR1 as well in increased phosphorylation of AMPK, a downstream signaling component that becomes active when either IGFRs or InsR or both transmit a signal, e.g., binding of insulin. Hence, IGFR-like seems to negatively regulate InsR and/or IGFR-mediated signaling. Also, with their knowledge of the invention, i.e., that the protein encoded by the KIAA1324 gene acts indeed as an IGFR-like receptor, the present inventors, by inspecting genome wide association studies (GWAS), found a strong association of SNPs in the KIAA1324 gene with type 2 diabetes, LDL cholesterol and/or coronary artery disease.

In sum, the protein encoded by the human KIAA1324 gene which the present inventors assigned a function of a modulator of IGFR2 and/or InsR, plays a role in metabolism, in particular in insulin signaling and also likely in LDL cholesterol metabolism as well as in attending ills such as coronary heart disease. This finding is of outstanding importance, since it was not believed that apart from IGFRs and InsR, there may be a further player in insulin signaling. Due to its presumed negative regulatory function on IGFRs and/or InsR, the IGFR-like receptor of the present invention appears to be an attractive target for modulators and may thus open new avenues for the development of medicaments, e.g. for treating diabetes, LDL cholesterol-associated disorder as well as coronary artery disease, particularly however diabetes mellitus type II.

Therefore, antagonists of said receptor open up new and urgently needed possibilities to revert, e.g. insulin resistance as commonly seen in diabetes mellitus type II pathogenesis, whereas agonists could be used to block insulin signaling. Strikingly, the present inventors could also show that the IGFR-like receptor is associated with β cell de-differentiation in the pancreas, an early event in disease onset that ultimately leads to β cell destruction or loss-of-function. Hence, the IGFR-like receptor is also a promising diagnostic tool enabling early diagnosis and treatment of diabetes before irrevocable loss of β cells, thereby potentially paving the way for the treatment of diabetes mellitus type I.

Accordingly, the present invention provides an isolated DNA sequence encoding an IGF receptor (IGFR)-like receptor which is capable of reacting with antibodies raised against an IGFR-like receptor of SEQ ID No: 1, wherein said antibodies specifically bind to at least one epitope of the sequence

```
(i)
                                  (SEQ ID NO.: 2)
TSKRTPDGFDSVPLKT;
and/or

(ii)
                                  (SEQ ID NO.: 3)
CHQCDPDKYSE;
and/or

(iii)
                                  (SEQ ID NO.: 4)
MYKWAKPKICSEDLEG;
and/or

(iv)
                                  (SEQ ID NO.: 5)
FQRTTFHEASRKYTN
```

-continued and/or (v)
(SEQ ID NO.: 6)
CTFSRNTPTRTFNY

In particular, said isolated DNA sequence may encode an IGFR-like receptor comprising a sequence corresponding to SEQ ID No. 1.

The isolated DNA sequence may in particular comprise a sequence corresponding to SEQ ID No. 7 (NM_0200775.4).

Further provided herein is a vector comprising the DNA sequence as described herein. Said vector may further comprise a gene regulation element operatively linked to the DNA sequence encoding said IGFR-like receptor. A host cell comprising said vector is also envisaged.

Further provided herein are binding agents capable of specifically binding an IGFR-like receptor, said IGFR-like receptor comprising a sequence corresponding to sequence SEQ ID No.1 for use as a diagnostic marker for diabetes or the risk of developing diabetes.

Antagonists and agonists of the IGFR-like receptor of the invention, said IGFR-like receptor comprising for example a sequence corresponding to SEQ ID No. 1, are also provided herein. Said antagonists and agonists are in general envisaged for use as a medicament. Specifically, the antagonists and agonists provided herein are intended for use in a method of prophylactic and/or therapeutic treatment of diabetes. Antagonists are however preferred.

The antagonists and agonists are envisaged to bind specifically to said IGFR-like receptor and may be selected from inter alia an antibody, a siRNA, a nucleic acid, an aptamer, a peptide, a protein, or a small molecule organic compound etc. The antibody may be a monoclonal or polyclonal antibody.

In particular, said antibody, which is preferably a monoclonal antibody, may be an antibody (e.g. a monoclonal antibody) specifically binding to an epitope of said IGFR-like receptor, the epitope comprising or consisting of the sequence:

(i)
(SEQ ID NO.: 2)
TSKRTPDGFDSVPLKT;
and/or (ii)
(SEQ ID NO.: 3)
CHQCDPDKYSE;
and/or (iii)
(SEQ ID NO.: 4)
MYKWAKPKICSEDLEG;
and/or (iv)
(SEQ ID NO.: 5)
FQRTTFHEASRKYTN
and/or (v)
(SEQ ID NO.: 6)
CTFSRNTPTRTFNY The present invention also provides a method of generating an antibody against an epitope of an IGFR-like receptor. The antibody can be prepared by a method including the following steps: (a) administering to a mammal an antibody-generating peptide from an IGFR-like receptor as set forth in SEQ ID NO: 1, wherein the peptide comprises a sequence selected from the group consisting of SEQ ID NO: 4 and 6; and (b) purifying the antibody.

The present invention also provides a binding agent, such as antibody or fragment thereof, which specifically binds to an IGFR-like receptor epitope as described herein, wherein said binding agent of the IGFR-like receptor includes complimentary determining regions (CDRs): CDR-H1: SYHIS (SEQ ID NO:13 or 19), CDR-H2: AISSGGDTYYNSLLKS (SEQ ID NO:14 or 20), CDR-H3: ESY (SEQ ID NO:15 or 21), CDR-L1: RASENIDTYLH (SEQ ID NO:16 or 22), CDR-L2: FASQSIS (SEQ ID NO:17 or 23), and CDR-L3: QQGNILPYT (SEQ ID NO:18 or 24); or CDR-H1: SYWMD (SEQ ID NO:25), CDR-H2: NIYPSDGETHYNQKFKD (SEQ ID NO:26), CDR-H3: LYSEYGS (SEQ ID NO:27), CDR-L1: KSSQSLLNSGNQKNYLT (SEQ ID NO:28), CDR-L2: WASTRDS (SEQ ID NO:29), and CDR-L3: QNDYSYPLT (SEQ ID NO:30). The binding agent can be an antibody or a fragment thereof that binds to an IGFR-like receptor epitope, and can have a variable heavy chain amino acid sequence SEQ ID NO:31, and a variable light chain amino acid sequence SEQ ID NO:32; a variable heavy chain amino acid sequence SEQ ID NO:33, and a variable light chain amino acid sequence SEQ ID NO:34, a variable heavy chain amino acid sequence SEQ ID NO:35, and a variable light chain amino acid sequence SEQ ID NO:36; a heavy chain amino acid sequence SEQ ID NO: 37, and a light chain amino acid sequence SEQ ID NO: 38; a heavy chain amino acid sequence SEQ ID NO: 39, and a light chain amino acid sequence SEQ ID NO: 40, or a heavy chain amino acid sequence SEQ ID NO: 41, and a light chain amino acid sequence SEQ ID NO: 42. The binding agent can be included in a pharmaceutical composition, optionally with one or more pharmaceutical excipients, which can be administered to increase InsR-mediated signaling in a subject. For example, the binding agent can increase phosphorylation of InsR, IGF1R, Akt, mTOR and/or AMPK. The binding agent can also be included in a diagnostic composition, which can be used in a method of diagnosing diabetes or the risk of developing diabetes.

In the diagnostic and/or therapeutic uses provided herein, diabetes is envisaged to comprise type 1 diabetes, type 2 diabetes, gestational diabetes, prediabetes, insulin resistance, metabolic syndrome, and impaired glucose tolerance.

Treatment with the antagonist or agonist of IGFR-like receptor, antagonists being preferred, may prevent or reverse insulin resistance and/or reverse de-differentiation and/or loss-of-function of pancreatic β-cells.

Further provided herein is a medicament or a pharmaceutical composition comprising an antagonist or agonist of IGFR-like receptor (antagonists being preferred). In a preferred embodiment said IGFR-like receptor comprises or consists of a sequence corresponding to SEQ ID No. 1. Said antagonist or agonist is in a preferred embodiment a monoclonal antibody that specifically binds to said IGFR-like receptor.

Said preferably monoclonal antibody is in particular envisaged to bind to an epitope of said IGFR-like receptor, the epitope comprising or consisting of the sequence (i)
(SEQ ID NO.: 2)
TSKRTPDGFDSVPLKT;
and/or (ii)
(SEQ ID NO.: 3)
CHQCDPDKYSE;
and/or -continued

```
(iii)
                                   (SEQ ID NO.: 4)
MYKWAKPKICSEDLEG;
and/or

(iv)
                                   (SEQ ID NO.: 5)
FQRTTFHEASRKYTN
and/or

(v)
                                   (SEQ ID NO.: 6)
CTFSRNTPTRTFNY
```

Further provided herein is a monoclonal antibody which specifically binds to an IGFR-like receptor epitope of the sequence

```
(i)
                                   (SEQ ID NO.: 2)
TSKRTPDGFDSVPLKT;
and/or

(ii)
                                   (SEQ ID NO.: 3)
CHQCDPDKYSE;
and/or

(iii)
                                   (SEQ ID NO.: 4)
MYKWAKPKICSEDLEG;
and/or

(iv)
                                   (SEQ ID NO.: 5)
FQRTTFHEASRKYTN
and/or

(v)
                                   (SEQ ID NO.: 6)
CTFSRNTPTRTFNY.
```

Further provided herein is an in vitro screening assay for antagonists or agonists of an IGFR-like receptor, said method comprising the steps of:

(a) providing a stable cell line expressing said IGFR-like receptor;

(b) contacting said cell line of (i) with a candidate antagonist or agonist; and (c) measuring or detecting an IGFR-like receptor downstream signaling event, wherein an antagonist is identified by suppressing said IGFR-like receptor downstream signaling event, and an agonist is identified by promoting said IGFR-like receptor downstream signaling event.

Said IGFR-like receptor comprises in a preferred embodiment a sequence corresponding to sequence SEQ ID No. 1.

Also provided herein is an IGFR-like receptor antagonist or agonist obtainable by the in vitro screening assay, said IGFR-like receptor antagonist or agonist being selected from an antibody, a siRNA, a nucleic acid, an aptamer, a peptide, a protein, or a small molecule organic compound.

Further, the invention provides an in vitro diagnostic assay for detection of degeneration of pancreatic islet cells in a subject, comprising the steps of:

i) contacting a sample, e.g. a plasma sample, of said subject with a diagnostic binding agent, e.g. a monoclonal antibody, that specifically binds to IGFR-like receptor;

ii) detecting the binding of the binding agent;

wherein detectable binding of said binding agent is indicative of de-differentiation of pancreatic islet cells in the subject; and wherein the IGFR-like receptor comprises a sequence corresponding to SEQ ID No. 1.

The diagnostic binding agent, which may in particular an antibody of the invention, such as a monoclonal antibody, is envisaged to specifically bind to, e.g., an IGFR-like receptor epitope of the sequence

```
(i)
                                   (SEQ ID NO.: 2)
TSKRTPDGFDSVPLKT;
and/or

(ii)
                                   (SEQ ID NO.: 3)
CHQCDPDKYSE;
and/or

(iii)
                                   (SEQ ID NO.: 4)
MYKWAKPKICSEDLEG;
and/or

(iv)
                                   (SEQ ID NO.: 5)
FQRTTFHEASRKYTN
and/or

(v)
                                   (SEQ ID NO.: 6)
CTFSRNTPTRTFNY.
```

De-differentiation of pancreatic islet cells is envisaged to be indicative of diabetes or the risk of developing diabetes.

The diagnostic binding agent may preferably be in the form of a composition, such as a diagnostic composition. Accordingly, the present invention also provides for a diagnostic composition comprising a diagnostic binding agent as described herein, optionally further comprising means for detecting binding of said diagnostic binding agent to its target, i.e., an IGFR-like receptor as described herein.

The present invention also relates to the use of the binding agents of the invention and in particular of the antibodies of the invention for the in vitro detection of degeneration of pancreatic islet cells. The use of these antibodies for the preparation of a therapeutic or diagnostic composition is also contemplated.

Further provided herein is a method of treating diabetes, comprising administering an IGFR-like receptor antagonist or agonist to a subject, said IGFR-like receptor comprising a sequence corresponding to SEQ ID No. 1.

DESCRIPTION OF THE FIGURES

The invention will be better understood with reference to the detailed description when considered in conjunction with the non-limiting examples and the accompanying drawings. The figures illustrate embodiments of methods of the invention. The patent or application file contains at least one drawing executed in color. Copies of this patent or patent application with color drawing(s) will be provided by the Office upon request and payment of the necessary fee.

FIG. 1: Depiction of the sequences listed throughout the specification. Sequence ID No 1 represent the long transcript of IGFR-like receptor and underlined in red are the predicted growth factor domains, underlined in green is the Mannose-6-phosphate receptor binding domain, underlined in black is the transmembrane region and in blue the cytoplasmic region. Highlighted in underlined bold characters are the 5 epitopes corresponding to sequence ID No: 2-6 for which antibodies were raised against.

FIG. 3: IGFR-like receptor knock-out mice die early after birth with normal body weight. Schematic representation of the EUCOMM allele (A) The EUCOMM allele is a knock-out first, reporter-tagged insertion with conditional potential (promoter-driven cassette) (Skarnes W C et al. 2011; Nature). The L1L2_Bact_P cassette was inserted at position 108489484 of Chromosome 3 upstream of the critical exon(s) (Build GRCm38). The cassette is composed of an FRT site followed by lacZ sequence and a loxP site. This first loxP site is followed by neomycin under the control of the human beta-actin promoter, SV40 polyA, a second FRT site and a second loxP site. A third loxP site is inserted downstream of the targeted exon at position 108488602. The critical exon is flanked by loxP sites. A "conditional ready" (floxed) allele can be created by flp recombinase expression in mice carrying this allele. Subsequent cre expression results in a knockout mouse. If cre expression occurs without flp expression, a reporter knockout mouse will be created. (http://www.informatics.jax.orgiallele/MG1:4436415) IGFR-like receptor knockout mice show normal appearance at birth but do not feed as shown by lack of milk in their stomach (B, stars), they are lethargic and display respiratory distress, signs of metabolic dysfunction. Mendelian ratios at different stages show normal distribution of the three genotypes until birth however the percentage of surviving knockout mice is significantly reduced after birth and until the weaning age. Only few survivors are found at the weaning age probably due to compensatory mechanisms and/or splicing around the inserted cassette leading to incomplete knockout (C). Histogram depicting normal body weight of knockout mice in comparison with the wild type and heterozygous littermates control at P0(D).

FIG. 12: Location of AP-2 binding and sorting signal in IGFR-like receptor. Figure shows the amino acid sequence of SEQ ID NO. 11, SEQ ID NO: 12 and a part of SEQ ID NO: 1.

FIG. 20: Association of KIAA1324 tagging SNPs with insulin sensitivity (A), adipokines and inflammation (B), and proinsulin conversion (C).

DETAILED DESCRIPTION

Figure 2:
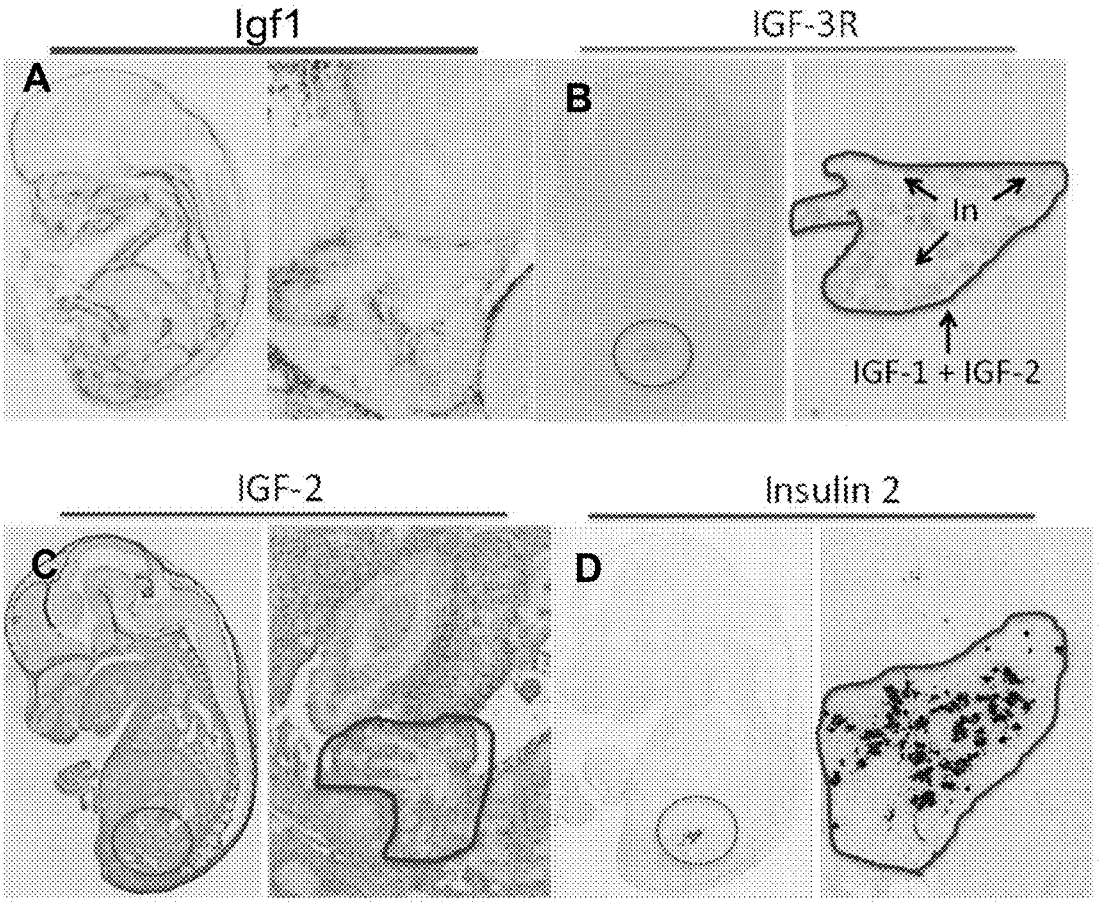
FIG. 2: Expression of IGFR-like receptor adjacent to IGF-1, IGF-2 and Insulin ligands in the pancreas. Genepaint.org in situ hybridization of the E14.5 mouse embryos shows specific expression of the IGFR-like receptor mRNA in the pancreas (B). IGF1 and IGF2 mRNA is expressed in tissues adjacent to the pancreatic epithelium (A,C), whereas Insulin mRNA is present in the endocrine compartment of the pancreas (D).

The present inventors have surprisingly discovered a novel IGFR-like receptor expressed adjacent to IGF-1, IGF-2 and Insulin ligands in the pancreas and have demonstrated that said IGFR-like receptor negatively regulates InsR and/or IGF1R-mediated signaling. Therefore, antagonists and agonists of said receptor open up new and urgently needed possibilities to revert insulin resistance as commonly seen in diabetes pathogenesis, whereas agonists could be used to block insulin signaling. Strikingly, the present inventors could also show that the IGFR-like receptor is associated with β cell de-differentiation in the pancreas, an early event in disease onset that ultimately leads to β cell destruction or loss-of-function. Hence, the IGFR-like receptor is also a promising diagnostic tool enabling early diagnosis and treatment of diabetes before irrevocable loss of β cells.

The present inventors pioneered in elucidating the function of the human KIAA1324 gene in encoding an IGFR-like receptor as described herein. The protein product of KIAA1324 previously referred to as UPF0577 protein KIAA1324 or Estrogen-induced gene 121 (EIG121) protein has commonly been known as a cancer marker, whereas the present inventors for the first time attributed a pivotal role in metabolism to the protein. The terms "IGFR-like receptor", "IGF-like receptor"; "IGF3 receptor" and "IGF3R" are used herein interchangeably herein.

In a first aspect, the invention thus provides an isolated DNA sequence encoding an IGF receptor (IGFR)-like receptor which is capable of reacting with antibodies raised against an IGFR-like receptor of SEQ ID No: 1, wherein said antibodies specifically bind to at least one epitope comprising the sequence

```
(i)
                                  (SEQ ID NO.: 2)
TSKRTPDGFDSVPLKT;
and/or

(ii)
                                  (SEQ ID NO.: 3)
CHQCDPDKYSE;
and/or
```

-continued

```
(iii)
                                  (SEQ ID NO.: 4)
MYKWAKPKICSEDLEG;
and/or

(iv)
                                  (SEQ ID NO.: 5)
FQRTTFHEASRKYTN
and/or

(v)
                                  (SEQ ID NO.: 6)
CTFSRNTPTRTFNY
```

In particular, said isolated DNA sequence is envisaged to encode UPF0577 protein KIAA1324 with Uniprot Acc. No. Q6UXG2, entry version 95 of 22 Jul. 2015 (SEQ ID No.: 1) or a functional variant thereof, said proteins also referred to as "IGFR-like receptor" herein.

Importantly, expression of the "EIG121" gene was in the prior art exclusively known for its role in neoplastic proliferations associated with estrogen excess. It was neither foreseen, nor foreseeable, that the protein product of the gene, i.e. the IGFR-like receptor described herein, regulates IGFR/IR signaling and would be specifically recognized by the antibodies binding to the epitopes comprising the sequence selected from SED ID NO. 1, 2, 3, 4, 5, or 6, or could be targeted with antagonists or agonists for treatment of diabetes.

Functional variants of the IGFR-like receptor disclosed herein, which have a threshold sequence identity or sequence homology to the IGFR-like receptor described herein, are also encompassed by the term "IGFR-like receptor". Said functional variants are envisaged to have at least 50%, 55%, 60%, 65%, 70%, 75%, 80%, 85%, 90%, 95%, 97%, 98%, 99%, 99.5% or 100% sequence identity with UPF0577 protein KIAA1324 with Uniprot Acc. No. Q6UXG2, entry version 95 of 22 Jul. 2015 (SEQ ID No.: 1) and are capable of reacting with antibodies raised against an IGFR-like receptor of SEQ ID No: 1, wherein said antibodies specifically bind to at least one epitope comprising the sequence

```
(i)
                                  (SEQ ID NO.: 2)
TSKRTPDGFDSVPLKT;
and/or

(ii)
                                  (SEQ ID NO.: 3)
CHQCDPDKYSE;
and/or

(iii)
                                  (SEQ ID NO.: 4)
MYKWAKPKICSEDLEG;
and/or

(iv)
                                  (SEQ ID NO.: 5)
FQRTTFHEASRKYTN
and/or

(v)
                                  (SEQ ID NO.: 6)
CTFSRNTPTRTFNY
```

It is further envisioned that said functional variants preferably exhibit the same properties as UPF0577 protein KIAA1324, i.e. inhibit or reduce InsR and/or IGF1R-mediated signaling, in particular (i) Akt phosphorylation and/or (ii) AMPK phosphorylation and/or (iii) mTOR phosphorylation as assessable by routine methods set out in the appended examples. The term "% identity" or "% sequence identity" as used herein refers to the percentage of pair-wise identical residues—following (homologous) alignment of a sequence of a polypeptide of the invention with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of two proteins. Preferably, the amino acid sequence shown in SEQ ID NO:1 is preferred as a "reference sequence". SEQ ID NO:1 shows the human UPF0577 protein KIAA1324, also referred to as IGFR-like receptor herein. The term "reference sequence" and "wild type sequence" (of the IGFR-like receptor) is used interchangeably herein. Alternatively, the amino acid sequence with the SWISS-PROT/UniProt Data Bank Accession Number Q6UXG2 (entry version 95 of 22 Jul. 2015) can be used as reference sequence.

The percentage of sequence homology or sequence identity can, for example, be determined herein using the BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

In the context of the invention, the expression "position corresponding to another position" (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified protein sequence represents, in addition to referral to amino acid positions of the specified protein sequence, referral to a collection of equivalent positions in other recognized protein and structural homologues and families. The same may be applied to the expression "sequence corresponding to sequence", mutatis mutandis. I.e., the referral to a sequence "corresponding to" a specified protein sequence [X], in addition to referral to sequence the specified protein sequence, referral to a collection of equivalent sequences in other recognized protein and structural homologues and families.

The term "InsR" or "IR" refers to the insulin receptor and generally comprises both the IR-A (also known as "isoform short") and IR-B (also known as "isoform long") isoforms. The InsR occurs as a tetramer of 2 $\alpha$ chains carrying the insulin-binding regions and 2 $\beta$ chains carrying the kinase domain, linked by disulfide bonds. The InsR is a receptor tyrosine kinase that is activated by binding of insulin, IGF-1 and IGF-2, ultimately leading to signaling through the MAPK/Ras-Raf-Erk pathway, the phosphatidylinositol-3-kinase/AKT/mTOR (PI3K/AKT) pathway and/or the Janus kinase/signal transducer and activator of transcription (JAK/STAT) pathway. More precisely, ligand binding to the $\alpha$-chains of the InsR ectodomain induces structural changes within the receptor leading to autophosphorylation of various tyrosine residues within the intracellular tyrosine kinase domain of the $\beta$-chain, leading to recruitment and phosphorylation of several intracellular substrates, including, insulin receptor substrates (IRS1, 2, 3, 4), SHC, GAB1, CBL and other signaling intermediates. Each of these phosphorylated proteins serve as docking proteins for other signaling proteins that contain Src-homology-2 domains (SH2 domain), including the p85 regulatory subunit of PI3K and SHP2. Phosphorylation of IRSs proteins leads to the activation of two main signaling pathways: the PI3K-AKT/PKB pathway, which is responsible for most of the metabolic actions of insulin, and the Ras-MAPK pathway, which regulates expression of some genes and cooperates with the PI3K pathway to control cell growth and differentiation. Binding of PI3K to phosphotyrosines on IRS1 leads and subsequent PI3K activation leads to the phosphorylation and activation of AKT, AMPK and mTOR, a signaling pathway which regulates metabolism and integrates signals from insulin. InsR activation upon ligand binding also triggers the Ras/RAF/MAP2K/MAPK pathway via phosphorylation of IRS1 and recruitment of GRB2/SOS, which is mainly involved in mediating cell growth, survival and cellular differentiation of insulin.

An illustrative example of the InsR is the human InsR with Uniprot Acc. No. P06213 (entry version 216 of Jul. 22, 2015) and variants thereof. Insulin receptors in the context of the present invention are preferably capable of inducing (i) Akt phosphorylation, and/or (ii) AMPK phosphorylation and/or (iii) mTOR phosphorylation upon binding of their ligand, in particular insulin.

The term "IGF-receptor 1" or "IGF1R" or "IGFRI" is used herein to refer to the Insulin-like growth factor 1 receptor tyrosine kinase. IGF1R binds to IGF1 with high affinity and IGF2 and insulin (INS) with a lower affinity. Ligand binding activates the receptor kinase, leading to receptor autophosphorylation, and phosphorylation of multiple substrates, including, the insulin-receptor substrates (IRS½), Shc and 14-3-3 proteins, which ultimately leads to the activation of three main signaling pathways: the PI3K-AKT/PKB pathway, the Ras-MAPK pathway., and the JAK/STAT pathway. The activated IGF1R is involved in cell growth and survival control. Thus, although InsR and IGF1R feed into similar signaling pathways, InsR-mediated signaling predominantly regulates metabolism, whereas IGF1R signaling is involved in cell growth and survival.

An illustrative example of the IGF1R is the human IGF1R with Uniprot Acc. No. P08069 (entry version 185 of Jul. 22, 2015) and variants thereof. IGF1R in the context of the present invention is preferably capable of inducing (i) Akt phosphorylation, and/or (ii) AMPK phosphorylation and/or (iii) mTOR phosphorylation upon binding of their ligand, in particular IGF1.

The term "IGF1" or "IGFI" refers to the Insulin-like growth factor I, a protein structurally and functionally related to insulin, but having a higher growth-promoting activity. An illustrative example is the human IGF1 with Uniprot Acc. No. P05019 (entry version 186 of Jul. 22, 2015). "IGF1" in the context of the present invention is preferably capable of binding to the IGF1 receptor and eliciting IGF1R signaling as described elsewhere herein.

The term "IGF2R" or "IGF2R" or "IGFRI I" is used herein to refer to the Insulin-like growth factor 2/mannose-6-phosphate (IGF-2/M6P) receptor. The IGF2R is a single transmembrane protein composed of a large extracytoplasmic (i.e. extracellular) domain, a single transmembrane region and a short cytoplasmic tail that lacks intrinsic catalytic activity. The receptor binds IGF-2 with higher affinity than IGF-1 and does not bind insulin. The IGF2R has been reported to interact, via distinct sites, with lysosomal enzymes and a variety of other M6P-containing ligands, and regulate extracellular IGF-2 concentrations, thereby modulating signaling through the growth-stimulatory IGF-1 receptor pathway.

An illustrative example of the IGF2R is the human IGF2R with Uniprot Acc. No. P11717 (entry version 174 of Jul. 22, 2015) and variants thereof.

The term "IGF2" or "IGFII" refers to the Insulin-like growth factor II. An illustrative example is the human IGF2 with Uniprot Acc. No. P01344 (entry version 199 of Jul. 22, 2015) and variants thereof. "IGF2" in the context of the present invention is preferably capable of binding to the IG2 receptor.

The isolated DNA sequence provided herein may comprise a sequence corresponding to the sequence of the human KIAA1324 gene (NCBI Gene ID 57535, updated on 15 Jul. 2015) as shown in SEQ ID No.: 7, or variants thereof. Variants of the human KIAA1324 gene may include orthologs. An ortholog, or orthologous gene, is a gene with a sequence that has a portion with similarity to a portion of the sequence of a known gene, but found in a different species than the known gene. An ortholog and the known gene originated by vertical descent from a single gene of a common ancestor.

As used herein a variant or ortholog of the human KIAA1324 gene is envisaged to encode an IGFR-like receptor or a functional variant thereof, i.e. preferably being capable of .inhibiting or reducing InsR and/or IGF1R-mediated signaling, in particular (i) Akt phosphorylation and/or (ii) AMPK phosphorylation and/or (iii) mTOR phosphorylation and having at least about 60%, 65%, 70%, 75%, 80%, 90%, 95%, 97%, 98%, 99%, 99.5% or 100% sequence identity with the human KIAA1324 gene (NCBI Gene ID 57535, updated on 15 Jul. 2015), i.e. sequence identity with the human KIAA1324 gene's coding sequence shown in SEQ ID NO: 7. The coding sequence is obtained by joining nucleotides 222..374, 47932..48052, 50537..50729, 57904..58051, 58526..58606, 59512..59617, 59726..59875, 71083..71171, 74215..74392, 75104..75232, 75630..75720, 77404..77509, 77764..77901, 78649..78912, 80459..80632, 83512..83692, 84017..84113, 84611..84712, 85892..86018, 86097..86275, 86773..86938, 88982.. 89050 of said human KIAA1324 gene (NG_032763.1).

As used herein the term "isolated DNA sequence" refers to a DNA molecule purified, or substantially purified, from endogenous material, including other nucleic acid sequences, proteins, peptides, lipids and so on naturally occurring in the cell and/or organism from which the DNA sequence is derived and includes DNA purified by standard purification techniques as well as DNA prepared by recombinant technology and those chemically synthesized.

Vector

The nucleic acid of the invention may also be in the form of, may be present in and/or may be part of a vector.

The term "vector" refers a nucleic acid molecule used as a vehicle to transfer (foreign) genetic material into a host cell and encompasses—without limitation—plasmids, viruses, cosmids and artificial chromosomes such as bacterial artificial chromosomes (BACs) and yeast artificial chromosomes (YACs). In general, engineered vectors comprise an origin of replication, a multicloning site and a selectable marker. The vector itself is generally a nucleotide sequence, commonly a DNA sequence that comprises an insert (transgene) and a larger sequence that serves as the "backbone" of the vector. Vectors may encompass additional elements besides the transgene insert and a backbone including gene regulation elements, genetic markers, antibiotic resistances, reporter genes, targeting sequences, or protein purification tags. Particularly envisaged within the context of the invention are expression vectors (expression constructs) for expression of the transgene in the host cell, which generally comprise—in addition to the transgene—gene regulation sequences.

An expression vector is, in general, a vector that can provide for expression of the IGFR-like receptor in vitro and/or in vivo (i.e. in a suitable host cell, host organism and/or expression system). The person skilled in the art will readily understand that choice of a particular vector include depends, e.g., on the host cell, the intended number of copies of the vector, whether transient or stable expression of the IGFR-like receptor is envisaged, and so on.

"Transient expression" results from the introduction of a nucleic acid (e.g. a linear or non-linear DNA or RNA molecule) or vector that is incapable of autonomous replication into a recipient host cell. Expression of the transgene occurs through the transient expression of the introduced sequence.

However, "stable expression" of the nucleic acid sequence as described herein will often be preferred and may be accomplished by either stably integrating the nucleic acid sequence into the host cell's genome or by introducing a vector comprising the nucleic acid sequence of the invention and being capable of autonomously replicating into the host cell.

The vector provided herein is in particular envisaged to comprise a gene regulation element operably linked to the DNA sequence encoding said IGFR-like receptor.

The term "gene regulation element" refers to DNA sequences necessary for the expression of an operably linked coding sequence in a particular host organism. The term "gene regulation element" includes controllable transcriptional promoters, operators, enhancers, silencers, transcriptional terminators, 5' and 3' untranslated regions which interact with host cellular proteins to carry out transcription and translation and other elements that may control gene expression including initiation and termination codons. The precise nature of the regulatory regions needed for gene expression may vary from organism to organism. Prokaryotic gene regulation elements, for example, include a promoter, optionally an operator sequence, and a ribosome binding site (RBS), whereas gene regulation elements for eukaryotic cells comprise promoters, polyadenylation (poly-A) signals, and enhancers.

The gene regulation element is envisaged to be "operably linked" to the gene to be expressed, i.e. placed in functional relationship with the same. For instance, a promoter or enhancer is "operably linked" to a coding nucleic acid sequence if it affects the transcription of the sequence. The DNA sequences being "operably linked" may or may not be contiguous. Linking is typically accomplished by ligation at convenient restriction sites or synthetic oligonucleotide adaptors or linkers.

Host Cell

Further provided herein is a host cell comprising the vector as described herein.

A variety of host cells can be employed for expressing the nucleic acid sequence encoding the IGFR-like receptor as described herein. Host cells can be prepared using genetic engineering methods known in the art. The process of introducing the vector into a recipient host cell is also termed "transformation" or "transfection" hereinafter. The terms are used interchangeably herein.

Host cell transformation typically involves opening transient pores or "holes" in the cell wall and/or cell membrane to allow the uptake of material. Illustrative examples of transformation protocols involve the use of calcium phosphate, electroporation, cell squeezing, dendrimers, liposomes, cationic polymers such as DEAE-dextran or polyethylenimine, sonoporation, optical transfection, impalefection, nanoparticles (gene gun), magnetofection, particle bombardment, alkali cations (cesium, lithium), enzymatic digestion, agitation with glass beads, viral vectors, or others. The choice of method is generally dependent on the type of cell being transformed, the vector to be introduced into the cell and the conditions under which the transformation is taking place.

As used herein, the term "host cell" refers to any cell or cell culture acting as recipients for the vector or isolated nucleic acid sequence encoding the IGFR-like receptor as described herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

E.g., the IGFR-like receptor can be produced in bacteria. In addition to prokaryotes, eukaryotic microbes such as filamentous fungi or yeast are suitable cloning or expression hosts for the IGFR-like receptor of the invention. Illustrative examples include *Saccharomyces cerevisiae, Schizosaccharomyces pombe, Kluyveromyces* hosts such as *K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus; yarrowia* (EP 402 226); *Pichia pastoris* (EP 183 070); *Candida; Trichoderma reesia* (EP 244 234); *Neurospora crassa; Schwanniomyces* such as *Schwanniomyces occidentalis*; and filamentous fungi such as *Neurospora, Penicillium, Tolypocladium*, and *Aspergillus* hosts such as *A. nidulans* and *A. niger.*

Suitable host cells for the expression of glycosylated antibody construct of the invention may also be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV.

Plant cell cultures of cotton, corn, potato, soybean, *petunia*, tomato, *Arabidopsis* and tobacco can also be used as hosts. Cloning and expression vectors useful in the production of proteins in plant cell culture are known to those of skill in the art.

Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO), mouse sertoli cells (TM4); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCLS 1); TRI cells; MRC 5 cells; FS4 cells; and human hepatoma cells (Hep G2).

Ligands

The present inventors have identified several domains in the IGFR-like receptor described herein which may harbor binding sites for potential ligands, that may inter alia serve as a template for providing the diagnostic binding agents and antagonists or agonists of the present invention. Said domains include two insulin-like growth factor binding domains (domain 1: amino acids 273-413 of SEQ ID NO. 1; domain 2: amino acids 579-659 of SEQ ID No. 1), a mannose-6-phosphate receptor binding domain (M6P domain, amino acids 655-857 of SEQ ID No. 1), a transmembrane domain (amino acids 908-930 of SEQ ID NO: 1) and a cytoplasmic domain (amino acids 932-1013 of SEQ ID No: 1). Said domains are also derivable from FIG. 1. The present invention thus also relates to binding agents, such as e.g., antibodies (monoclonal antibodies being preferred), that specifically bind to at least one of the above mentioned domains.

Proteins comprising an insulin-like growth factor binding domain (InterPro Acc. No. IPR009030) include, without limitation, the insulin-like growth factor-binding proteins (IGFBP1-6), the type-1 insulin-like growth-factor receptor (IGF-1R), the receptor protein-tyrosine kinase Erbb-2, Erbb-3 and Erbb-4 (ErbB2, −3, −4), Ephrin Type A/B receptor, epidermal growth factor receptor (EGFR), EGFR-like binding proteins, CYR61, Matrilin-2, −3 and −4, Delta-like protein 1, Cubilin, Slit homolog 1 and 3 protein, Multiple epidermal growth factor-like domains protein 6, Low-density lipoprotein receptor-related protein 4, WNT1-inducible-signaling pathway protein 2, WNT1-inducible-signaling pathway protein 1, WNT1-inducible-signaling pathway protein 3, EGF-containing fibulin-like extracellular matrix protein 2, Low-density lipoprotein receptor, Pro-epidermal growth factor, Complement component C9, Thrombomodulin, Vitamin K-dependent protein S, Complement component C8 alpha chain, Uromodulin, Furin, Bone morphogenetic protein 1, Nidogen-1, Insulin receptor-related protein, Fibulin-1 and -2, Proprotein convertase subtilisin/kexin type 6, Connective tissue growth factor, Fibrillin-1, -2 and -3, Neurogenic locus notch homolog protein 1, Protein NOV homolog, CD97 antigen, Cartilage oligomeric matrix protein, Keratin, type II cuticular Hb3, Protein jagged-1, Protein crumbs homolog 1, Serine protease HTRA4, Serine protease HTRA3, Low-density lipoprotein receptor-related protein 2, Neurogenic locus notch homolog protein 2, Tumor necrosis factor receptor superfamily member 9, Prolow-density lipoprotein receptor-related protein 1, EGF-containing fibulin-like extracellular matrix protein 1, Nidogen-2, Scavenger receptor class F member 1, Adhesion G protein-coupled receptor E1, Growth arrest-specific protein 6, Keratin, type I cuticular Ha2, Latent-transforming growth factor beta-binding protein 1, Latent-transforming growth factor beta-binding protein 2, R-spondin-1, -2 and -4, Sushi, von Willebrand factor type A, EGF and pentraxin domain-containing protein 1, Uromodulin-like 1, Meckelin, Protein eyes shut homolog, Proprotein convertase subtilisin/kexin type 4, Sushi domain-containing protein 1, Cysteine-rich with EGF-like domain protein 2, Nephronectin, Protocadherin Fat 4, BMP/retinoic acid-inducible neural-specific protein 3, Extracellular matrix protein FRAS1, Epidermal growth factor-like protein 6, Signal peptide, CUB and EGF-like domain-containing protein 1, Signal peptide, CUB and EGF-like domain-containing protein 3, Latent-transforming growth factor beta-binding protein 4, Hemicentin-2, Delta and Notch-like epidermal growth factor-related receptor, Insulin-like growth factor-binding protein-like 1, Serine protease HTRA1, Proprotein convertase subtilisin/kexin type 5, Protein kinase C-binding protein NELL1, von Willebrand factor C and EGF domain-containing protein, Scavenger receptor class F member 2, Cysteine-rich with EGF-like domain protein 1, Kazal-type serine protease inhibitor domain-containing protein 1, Hemicentin-1, Protein kinase C-binding protein NELL2, Neurogenic locus notch homolog protein 4, R-spondin-3, Adhesion G protein-coupled receptor E3, Mucin-13, Endosialin, Cadherin EGF LAG seven-pass G-type receptor 2, Complement component C1q receptor, Endothelial cell-specific molecule 1, Signal peptide, CUB and EGF-like domain-containing protein 2, Delta-like protein 4, Latent-transforming growth factor beta-binding protein 3, Dela-like protein 3, Cadherin EGF LAG seven-pass G-type receptor 1, Low-density lipoprotein receptor-related protein 1B, Cysteine-rich motor neuron 1 protein, Fibulin-5, Epidermal growth factor-like protein 7, Adhesion G protein-coupled receptor E2, Neurogenic locus notch homolog protein 3, Protein jagged-2 and others.

Potential ligands of the IGFR-like receptor described herein thus include ligands of the aforementioned proteins, such as IR, IGF1R, insulin, IGF1, IGF2, ephrin-B1, ephrin-B2, EGF, EGFR, TGFA/TGF-alpha, amphiregulin, epigen/EPGN, BTC/betacellulin, epiregulin/EREG, HBEGF/heparin-binding EGF, GP30, ALB, MB, Kappa and lambda-light chains, TF, hemoglobin, GC, SCGB1A1, APOA1, high density lipoprotein, the GIF-cobalamin complex, LRP2, LGALS3, AGRIN, IL-1, IL-2, TNF, collagen I and IV, perlecan, laminin, heparin, integrin, fibronectin, protein C, EFNAS, EFNB1, EFNB2, EFNB3, Jagged1, Jagged2 and Delta1, neuregulins, NTAK, CSPG5, TNFSF9/4-1BBL, Ac-LDL, AXL, TYRO3 MER, NRG1, NRG2, NRG3, NRG4, BTC, EREG, HBEGF, GR4, LGR5, LGR6, C1q, mannose-binding lectin (MBL2), pulmonary surfactant protein A (SPA), TGFBR2, and fragments and variants thereof.

Proteins comprising Mannose-6-phosphate receptor binding domain (InterPro Acc. No. IPR009011) include, without limitation, the cation-independent mannose-6-phosphate receptor, glucosidase 2 subunit β, the cation-dependent mannose-6-phosphate receptor, Protein OS-9, Endoplasmic reticulum lectin 1, and N-acetylglucosamine-1-phosphotransferase subunit gamma.

Potential ligands of the IGFR-like receptor provided herein therefore include ligands of the aforementioned proteins, such as IGF2, DPP4, phosphomannosyl, TRPV4, IGF2, lysosomal enzymes, TGF β, Leukemia inhibitory factor (LIF), Proliferin, Thyroglobulin, Prorenin, Granzyme B, and Retonic Acid.

The present inventors found that knockdown of the IGFR-like receptor resulted in increased phosphorylation of IGF1R and IR, and of downstream signaling proteins Akt-, mTOR-, and AMPK. It is thus supposed that the IGFR-like receptor may inhibit or dampen IGF1R- and/or IR activation and/or downstream signaling. Without wishing to be bound by specific theory, it is thought that the IGFR-like receptor may for instance function as an "insulin scavenger" receptor depleting insulin from the blood and transferring it to the endo- and lysosomal compartments where it may be degraded. It is also speculated that the IGFR-like receptor may associate with the insulin receptor (InsR), resulting in removal of the InsR from the cell surface. Either way, both scenarios may explain decreased InsR activation and InsR and/or IGF1R-mediated signaling, including phosphorylation of InsR, Akt, mTOR and/or AMPK in the presence of functional IGFR-like receptors. Therefore, insulin, InsR and/or the insulin-IR complex are particularly envisaged as ligands for the IGFR-like receptor provided herein.

Antagonists and Agonists

Further, agonists and antagonists of the IGFR-like receptor described herein are provided. As described herein and demonstrated in the appended examples, the IGFR-like receptor has been found to negatively regulate, i.e., inhibit or reduce InsR- and/or IGF1R-mediated signaling, and in particular (i) Akt phosphorylation, (ii) AMPK phosphorylation and (iii) mTOR phosphorylation.

The term "antagonist" refers to receptor ligand that inhibits or reduces agonist-mediated biological responses rather than provoking a biological response itself upon binding to the receptor. Antagonists have affinity but essentially no efficacy for their receptors. The term also comprises antagonists binding to the active (orthosteric) or to allosteric sites of their receptors, and/or to other binding sites not normally involved in receptor function. The term "antagonist" in general comprises full and partial antagonists, reversible and irreversible antagonists. In accordance with the invention, the antagonist preferably specifically binds to the IGFR-like receptor. Now that the novel function of the UPF0577 protein KIAA1324 has been elucidated, the skilled person will readily be able to identify IGFR-like receptor antagonists, e.g. by applying the screening assay as described herein. In accordance with the foregoing, IGFR-like receptor antagonists are envisaged to abolish the receptors capability of interfering with, i.e. inhibiting or reducing InsR- and/or IGFR signaling, and may for instance be particularly useful in reverting insulin resistance. Specifically, it is envisioned that IGFR-like receptor antagonists are capable of increasing InsR and/or IGF1R-mediated signaling, and in particular phosphorylation of IGF1R, InsR, Akt, mTOR and/or AMPK, as ascertainable using routine methods known in the art and described in the appended examples.

The term "agonist" as used herein generally refers to a receptor ligand that activates the receptor upon binding to produce a biological response. In contrast to antagonists, agonists have both affinity and efficacy for their receptors. The term "agonist" in general comprises full and partial agonists, reversible and irreversible agonists. In accordance with the invention, the agonist preferably specifically binds to the IGFR-like receptor. In accordance with the foregoing, it is envisaged that IGFR-like receptor agonists evoke or increase biological responses of the IGFR-like receptor, i.e., reduce and/or inhibit InsR activation and downstream signaling. It is thus envisaged that IGFR-like agonists are capable of decreasing InsR and/or IGF1R-mediated signaling, and in particular phosphorylation of InsR, IGF1R, Akt, mTOR and/or AMPK as ascertainable using routine methods known in the art and described in the appended examples.

The "antagonist" or "agonist" of the present invention may in general be any molecule, such as an antibody, a siRNA, a nucleic acid, an aptamer, a peptide, a protein, or a small molecule organic compound, that binds or specifically binds to an IGFR-like receptor as specified herein, or a variant or a fragment thereof, and either blocks or reduces the biological responses mediated by the IGFR-like receptor (i.e. acts as an antagonist) or induces or increases the biological responses mediated by the IGFR-like receptor (i.e. acts as an agonist).

Agonists and antagonists of the IGFR-like receptor can be easily found e.g. using the screening assay as provided herein. The skilled person will readily acknowledge that ligands of proteins comprising e.g. an insulin-like growth factor binding domain and/or a mannose-6-phosphate receptor binding domain (exemplary proteins and ligands have been described in the "Ligands" section above) may be used as a template for preparing agents capable of binding to the IGFR-like receptor and exhibiting an agonistic or antagonistic effect. E.g., in case of protein or peptide ligands, variants and fragments thereof can be easily prepared using routine methods of genetic engineering. The agonists and antagonists of the invention are envisaged to specifically bind to the IGFR-like receptor described herein (i.e. preferably do not exhibit cross-reactivity towards targets other than the IGFR-like receptor), as can easily be tested e.g. by evaluating antibody binding in IGFR-like receptor knockdown host cells (see appended examples).

Antibody

The antagonist or agonist provided herein may be an antibody. The antibodies provided herein preferably exhibit the desired biological activity, i.e. specifically bind to the IGFR-like receptor described herein. Specifically, it is envisaged that the antagonistic antibodies of the invention are capable of increasing InsR and/or IGF1R-mediated signaling, and in particular phosphorylation of IGF1R, InsR, Akt, mTOR and/or AMPK, as ascertainable using routine methods known in the art and described in the appended examples. It is also envisaged that the antagonistic antibodies of the invention bind to the epitopes (SEQ ID Nos 2-6). The present invention thus also relates to an antibody that (a) specifically binds to at least one of the epitopes depicted in SEQ ID Nos 2-6 and (b) increases phosphorylation of IGF1R, InsR, Akt, mTOR and/or AMPK. "Increase" thereby denotes an increase in the respective signal in the presence of the antibody when compared to the absence of the antibody in the respective detection method which is used for the detection and/or quantification of said increase. The present invention further relates to an antibody that binds to (a) one of the aforementioned growth factor binding domains and/or Manose-6-phosphate receptor binding domain (depicted in FIG. 1) and (b) increases phosphorylation of IGF1R, InsR, Akt, mTOR and/or AMPK. "Increase" thereby denotes an increase in the respective signal in the presence of the antibody when compared to the absence of the antibody in the respective detection method which is used for the detection and/or quantification of said increase. Strikingly, IGFR-I contains an extracellular domain that shows great similarity to the HER2 dimerization region, which is targeted by the antibody trastuzumab (Herceptin®). HER2 is constitutively active being able to dimerize with other HER family members acting in a ligand-independent manner and targeting HER2 by trastuzumab blocks its activity and inhibits cancer growth. Moreover, IGFR-I contains a GxxxG dimerization motif in its transmembrane domain that is found in members of the EGFR family. This suggests that IGFR-I homo- and heterodimerizes with EGFR and IR family members to regulate cell signaling outcome, metabolic vs mitogenic. It is thus also envisaged that the antibodies of the invention targeting IGFR-like receptor interfere with receptor homo- and heterodimerization and/or ligand binding.

Methods to provide such antibodies are well known to the skilled person (e.g. WO/2014/124020) and exemplified hereinafter. One may purify the IGFR-I ectodomain as well as the full-length receptor to high purity using a mammalian expression system to generate fully N-glycosylated, properly folded receptor with native conformation. Receptor reconstitution in synthetic membranes not only allows for dimerization of the receptor within a lipid bilayer, but also presents the receptor as an antigen in the membrane context and thus is highly suitable for the generation of the antibodies of the present invention and in particular f the therapeutic antibodies of the invention. Thus IGFR-I proteoliposomes are a synthetic mimic of the cellular membranes and thus ideal to produce e.g. monoclonal. These antibodies are directed against the extracellular domain of the receptor only and may interfere with receptor homo- and heterodimerization and/or ligand binding. It is thus also envisaged that the antibodies of the invention are capable of binding to the glycosylated IGFR-like receptor, preferably to its glycosylated ectodomain.

As is well known in the art, an antibody is an immunoglobulin molecule capable of specific binding to a target (epitope) through at least one epitope recognition site, located in the variable region of the immunoglobulin molecule. The term "antibody" as used herein comprises monoclonal and polyclonal antibodies, as well as (naturally occurring or synthetic) fragments or variants thereof, including fusion proteins comprising an antibody portion with an antigen-binding fragment of the required specificity and any other modified configuration of the antibody that comprises an antigen-binding site or fragment (epitope recognition site) of the required specificity. Illustrative examples include dAb, nanobody, affibody, Fab, Fab', $F(ab')_2$, Fv, single chain Fvs (scFv), diabodies, and minibodies comprising a scFv joined to a CH3 domain. It will be understood that other antibody frameworks or scaffolds comprising "antigen-binding sites" can be employed in line with the present invention. The term "antibody" thus also comprises these scaffolds. The mentioned scaffolds include e.g. non-immunoglobulin based antibodies and scaffolds onto which CDRs of the antibodies can be grafted. Such scaffolds include for example anticalins, avimers, affilins etc.

The antibody may be a chimeric antibody (or antigen-binding variant or fragment thereof). The term "chimeric antibody" refers to an antibody in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies.

The antibody may be a humanized antibody (or antigen-binding variant or fragment thereof). The term "humanized antibody" refers to an antibody containing a minimal sequence derived from a non-human antibody. In general, humanized antibodies are human immunoglobulins comprising residues from a hypervariable region of an immunoglobulin derived from non-human species such as mouse, rat, rabbit or non-human primate ("donor antibody") grafted onto the human immunoglobulin ("recipient antibody"). In some instances, framework region (FR) residues of the human immunoglobulin are replaced by corresponding non-human residues. Furthermore, humanized antibodies may comprise residues that are neither found in the recipient antibody nor in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

The antibody may be a human antibody. A "human antibody" is one that possesses an amino-acid sequence corresponding to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, J. Mol Biol, 227:381 (1991); Marks et al, J. Mol Biol, 222:581 (1991)). Also available for the preparation of human monoclonal antibodies are methods described in Cole et al, Monoclonal Antibodies and Cancer Therapy, Alan R. Liss, p. 77 (1985) and Boerner et al., J. Immunol, 147W: 86-95 (1991). See also van Dijk and van de Winkel, Curr. Opin. Pharmacol, 5: 368-374 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, Proc. Natl. Acad. Sci. USA, 103:3557-3562 (2006) regarding human antibodies generated via a human B-cell hybridoma technology.

Chemical Modifications

The antibodies or antigen-binding variants or fragments thereof used in accordance with of the invention may be modified. Typical modifications conceivable in the context of the invention include, e.g., chemical modifications as described in the following.

Generally, all kind of modifications are conceivable as long as they do not abolish the capability of the antibodies or antigen-binding variants or fragments thereof to specifically bind to the IGFR-like receptor and act as antagonists or agonists of the IGFR-like receptor as described elsewhere herein.

Possible chemical modifications of the antibody or antigen-binding variants or fragments thereof include acylation or acetylation of the amino-terminal end or amidation or esterification of the carboxy-terminal end or, alternatively, on both. The modifications may also affect the amino group in the side chain of lysine or the hydroxyl group of threonine. Other suitable modifications include, e.g., extension of an amino group with polypeptide chains of varying length (e.g., XTEN technology or PASylation®), N-glycosylation, O-glycosylation, and chemical conjugation of carbohydrates, such as hydroxyethyl starch (e.g., HESylation®) or polysialic acid (e.g., PolyXen® technology). Chemical modifications such as alkylation (e.g., methylation, propylation, butylation), arylation, and etherification may be possible and are also envisaged.

As described elsewhere herein, several domains have been identified in the IGFR-like receptor of the invention. Antibodies acting as antagonists or agonists of the IGFR-like receptor are in principle envisaged to bind anywhere in, or in between, the preferably extracellular domains of the IGFR-like receptor (e.g., the insulin-like growth factor binding domain, the mannose-6-phosphate receptor binding domain). As such, known antibodies binding to proteins comprising one or more of said domains (exemplary proteins have been listed in the "ligands" section above), and in particular binding to an epitope in the insulin-like growth factor binding domain or the mannose-6-phosphate receptor binding domain of said proteins, are generally also envisaged as antagonists or agonists and can be easily monitored for their antagonistic or agonistic behavior in the screening assay provided herein.

Further, antibodies against the IGFR-like receptor can be prepared as described in the appended examples and tested for their agonistic or antagonistic activity in the screening assay provided herein.

The antibodies provided as antagonists or agonists in accordance with the present invention are in particular envisaged to be capable of binding to an IGFR-like receptor epitope comprising the sequence

```
(i)
                                  (SEQ ID NO.: 2)
TSKRTPDGFDSVPLKT;
and/or

(ii)
                                  (SEQ ID NO.: 3)
CHQCDPDKYSE;
and/or

(iii)
                                  (SEQ ID NO.: 4)
MYKWAKPKICSEDLEG;
and/or

(iv)
                                  (SEQ ID NO.: 5)
FQRTTFHEASRKYTN
and/or

(v)
                                  (SEQ ID NO.: 6)
CTFSRNTPTRTFNY
```

The antibodies preferably bind to the IGFR-like receptor described herein specifically, i.e. not to exhibit cross-reactivity towards non-target molecules such as InsR, the IGF1R and IGF2R. Specific binding of the antibodies recognizing the epitopes comprising SEQ ID NO: 2, 3, 4, 5 and 6 has been demonstrated in the appended examples. E.g., it could be demonstrated that antibody binding is abolished upon knockdown of the IGFR-like receptor, indicating that no unspecific binding took place.

The term "epitope" in general refers to a site on an antigen to which a binding domain, such as an antibody or immunoglobulin or derivative or fragment of an antibody or of an immunoglobulin, specifically binds. An "epitope" is antigenic and thus the term epitope is sometimes also referred to herein as "antigenic structure" or "antigenic determinant". Thus, the binding domain is an "antigen interaction site". Said binding/interaction is also understood to define a "specific recognition". The term "epitope" encompasses linear epitopes and conformational epitopes. Linear epitopes are contiguous epitopes comprised in the amino acid primary sequence and typically include at least 3 or at least 4, and more usually, at least 5 or at least 6 or at least 7, for example, about 8 to about 10 amino acids in a unique sequence. Conformational epitopes are formed by non-contiguous amino acids juxtaposed by folding of the protein. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

Other molecules are also envisaged herein as antagonists or agonists of the IGFR-like receptor.

siRNAs and nucleic acids are particularly useful as IGFR-like receptor antagonists that reduce or inhibit expression of the human KIAA1324 gene (or variants or orthologs thereof). The term "siRNA" is used interchangeably with "small interfering RNA" or "silencing RNA". siRNAs are double-stranded "antisense" RNA molecules, typically including a sequence of at least 20 consecutive nucleotides having at least 95% sequence identity to the complement of the sequence of the target nucleic acid, such as the coding sequence of the human KIAA1324 gene, but may as well be directed to regulatory sequences of said gene, including the promoter sequences and transcription termination and poly-adenylation signals.

Other nucleic acids capable of reducing and/or inhibiting IGFR-like receptor expression include aptamers, Spiegelmers®, nc-RNAs (including anti-sense-RNAs, L-RNA Spiegelmer®, silencer RNAs, micro-RNAs (miRNAs), short hairpin RNAs (shRNAs), small interfering RNAs (siRNAs), repeat-associated small interfering RNA (rasiRNA), and molecules or an RNAs that interact with Piwi proteins (piRNA). Such non-coding nucleic acid molecules can for instance be employed to direct IGFR-like receptor mRNA degradation or disrupt IGFR-like receptor mRNA translation. A respective reactant, in particular siRNA molecule, may in principle be directly synthesized within the host cell, or may be introduced into the host cell.

Peptides and proteins can in general be employed as IGFR-receptor antagonists or agonists, depending on whether they suppress (antagonists) or evoke (agonists) the biological responses mediated by IGFR-like receptor signaling. The term "polypeptide" and "protein" are used interchangeably herein. It is envisaged that proteins and peptides bind specifically to the IGFR-like receptor. As set out previously herein, the skilled person will readily be able to find peptide and protein antagonists or agonists capable of specifically binding to the IGFR-like receptor e.g. using known ligands of proteins comprising an insulin-like growth factor binding domain and/or a mannose-6-phosphate receptor binding domain (exemplary proteins have been listed in the "ligands" section above). Said ligands may be used as a template for preparing variants or fragments thereof using known methods of genetic engineering. Said proteins and peptides can subsequently be tested for their agonistic or antagonistic activity using e.g. the screening assay provided herein. Small organic molecules are, too, capable of either acting as IGFR-like receptor antagonists or agonists. It is envisaged that small organic molecules specifically bind to the IGFR-like receptor. High-throughput screening assays for small organic molecules are readily available in the art and can be employed to find ligands of the IGFR-like receptor provided herein that may exhibit agonistic or antagonistic activity.

Specific Binding

As set out herein, specific binding of the binding agents, in particular antagonists and agonists provided herein, e.g. antibodies, to the IGFR-like receptor is preferred. The terms "binding to" and "recognizing" in all grammatical forms are used interchangeably herein.

The term "specifically binds" generally indicates that a binding agent, in particular an antagonist or agonist, such as an antibody, binds with higher affinity to its intended target (i.e. the IGFR-like receptor described herein) than to its non-target molecule. Non-target molecules include the IGF receptors, in particular the human IGF1R with Uniprot Acc. No. P08069 (entry version 185 of 22 Jul. 2015), the human IGF2R with Uniprot Acc. No. P11717 (entry version 174 of 22 Jul. 2015), and the human InsR with Uniprot Acc. No. P06213 (entry version 216 of 22 Jul. 2015); and functional variants thereof. Preferably the affinity of the agonist or antagonist will be at least about 5-fold, preferably 10 fold, more preferably 25-fold, even more preferably 50-fold, and most preferably 100-fold or more, greater for a target molecule than its affinity for a non-target molecule. Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Preferably, the term "specifically binds" thus indicates that an antagonist or agonist, such as an antibody, exclusively binds to its intended target (i.e., the IGFR-like receptor).

Treatment

It is envisaged that the IGFR-like receptor antagonists and agonists are particularly useful in treatment and diagnostic of diabetes. As used herein, "diabetes" refers to the broad class of disorders characterized by impaired insulin production and glucose tolerance and in general includes type 1 and type 2 diabetes (also called juvenile and adult-onset, respectively), gestational diabetes, prediabetes, insulin resistance, metabolic syndrome, and impaired glucose tolerance. Diabetes results from a deficiency or functional impairment of insulin-producing β cells, alone or in combination with insulin resistance.

The term "metabolic syndrome" comprises abdominal (central) obesity, elevated blood pressure, elevated fasting plasma glucose, high serum triglycerides, low high-density lipoprotein (HDL) and/or high low-density lipoprotein (LDL) levels. Further it is associated with the risk of developing type 2 diabetes and/or cardiovascular disease including coronary heart diseases.

The term "β cell(s)", "beta cell(s)" and "islet cell(s)" are used interchangeably herein to refer to the pancreatic β cells located in the islet of Langerhans. Their primary function is to store and release insulin.

Defective insulin secretion underlies all forms of diabetes mellitus. Whereas the destruction of β-cells is responsible for type 1 diabetes (T1D), both lowered β-cell mass and loss of secretory function are implicated in type 2 diabetes (T2D). Emerging results suggest that a functional deficiency, involving de-differentiation of the mature β-cell towards a more progenitor-like state, may be an important driver for impaired secretion in T2D.

It is contemplated that the antagonists and agonists of the present invention can advantageously be employed in preventing β cell de-differentiation and/or reverting β cell loss-of-function. The antagonist and agonists described herein are therefore envisaged for use as a medicament. Particularly, said antagonists and agonists are intended for use in a method of prophylactic and/or therapeutic treatment of diabetes.

Type 1 diabetes is also known as Insulin Dependent Diabetes Mellitus (IDDM), and juvenile diabetes. The terms are used interchangeably herein. This form accounts for 5-10% of diabetes and is thought to be due to cellular-mediated autoimmune destruction of the pancreatic β-cells, resulting in little or no insulin secretion. Antagonists and agonists of the IGFR-like receptor provided herein may be capable of preventing or even reverting β cell de-differentiation and/or loss-of-function. Thus, the present invention is envisaged to open up new possibilities for a preventive or regenerative therapy of T1D.

Type 2 diabetes is also referred to as adult-onset diabetes and accounts for ~90-95% of all diabetes. Insulin resistance in target tissues and a relative deficiency of insulin secretion from pancreatic β-cells are the major features of type 2 diabetes (T2D). Insulin resistance is used herein to denote a condition characterized by the failure of target cells to respond to insulin, leading to hyperglycemia. Pancreatic β cells in the pancreas subsequently increase their production of insulin, leading to hyperinsulinemia. Without wishing to be bound by specific theory, it is contemplated the IGFR-like receptor described herein acts as a scavenger for either insulin or the insulin receptor. E.g., the IGFR-like receptor may bind to the insulin receptor, leading to internalization of the same (insulin receptor scavenger). The IGFR-like receptor may also bind to insulin, leading to its internalization and potentially lysosomal degradation (insulin scavenger). By inhibiting these IGFR-like receptor functions with the help of antagonists as described herein, InsR- and/or IGF1R-mediated signaling may increase, thereby restoring insulin sensitivity.

As further shown in the appended examples, the present inventors demonstrated that the IGFR-like receptor described herein negatively regulates insulin downstream signaling. IGFR-like receptor antagonists are therefore envisaged to promote or restore InsR downstream signaling, whereas IGFR-like receptor agonists are thought to inhibit or dampen InsR signaling.

IGFR-like receptor antagonists are therefore preferably capable of (i) increasing InsR and/or IGF1R-mediated Akt phosphorylation, (ii) increasing InsR and/or IGF1R-mediated AMPK phosphorylation and/or (iii) mTOR phosphorylation, thereby advantageously increasing insulin sensitivity in insulin-resistant cells.

Diagnostics

The present inventors have surprisingly discovered that the expression of the IGFR-like receptor specified herein is associated with de-differentiation of pancreatic β cells. β-cell de-differentiation is a term used to describe a change in β-cell phenotype that reverts back toward the multipotent progenitor cell from which it originated or a separate reversible dedifferentiated state. Pancreatic β cell de-differentiation is thought to lead to loss of key functions including insulin secretion. The dysregulated insulin secretion as a result of loss of critical β-cell functions is seen a fundamental part of the pathogenesis of diabetes (including T1D and T2D). Hyperglycemia is thought to be a major cause of pancreatic β cell de-differentiation leading to dysfunctional insulin secretion; a process also called glucose toxicity.

By the filing of this application, no reliable biomarkers for disease onset and progression were available. The present inventors have discovered that the IGFR-like receptor described herein is not only a potential and powerful target useful for diabetes treatment, but also accompanies pathogenesis at very early stages. Therefore, monitoring expression of the IGFR-like receptor provided herein allows for early diagnosis of diabetes and may even enable (prophylactic) treatment before β cells are lost or severely impaired in their function.

The present invention therefore provides a binding molecule capable of specifically binding to an IGFR-like receptor as described herein for use as a diagnostic marker for diabetes or the risk of developing diabetes. Preferably, said IGFR-like receptor comprises a sequence corresponding to sequence SEQ ID No 1, however, variants of said IGFR-like receptor are also envisaged.

In view of the foregoing, an in vitro diagnostic assay (i.e. diagnostic method) for detection of de-differentiation of pancreatic islet cells in a subject is also provided herein, said assay comprising the steps of:

i) contacting a sample obtained from said subject with a diagnostic binding agent that specifically binds to soluble IGFR-like receptor;

ii) detecting the binding of the diagnostic binding agent;

wherein detectable binding of said diagnostic binding agent is indicative of de-differentiation of pancreatic islet cells in the subject; and wherein the IGFR-like receptor comprises a sequence corresponding to SEQ ID No. 1.

As set out elsewhere herein, de-differentiation of pancreatic β cells is thought to be indicative of diabetes or the risk of developing diabetes. The sample can in general be any sample, in particular a plasma sample.

In general, in order to provide a diagnostic binding agent, the skilled person may follow the same principles as set out in the context of providing antagonists and agonists of the IGFR-like receptor. Likewise, diagnostic binding agents provided herein are envisaged to specifically bind to the IGFR-like receptor provided herein. Diagnostic binding agents may exhibit antagonistic or agonistic activities (thereby e.g. enabling simultaneous diagnosis and (preventive) treatment, or may not have an effect on IGFR-like receptor signaling at all. When preparing diagnostic binding agents, the skilled person may, as described elsewhere herein, for example use ligands and proteins comprising insulin-like growth factor binding domains and/or mannose-6-phosphate receptor binding domains and use their ligands as "templates" for generating diagnostic binding agents capable of specifically binding to the IGFR-like receptor. Exemplary proteins and ligands have been described in the "ligands" section herein. The approach has been described in the context of preparing antagonists and agonists of the IGFR-like receptor and is fully applicable to the diagnostic binding agents as well, with the exception that such binding agents do not necessarily have to exhibit agonistic and/or antagonistic properties.

Particularly useful binding agents for use within the in vitro diagnostic binding assay comprise monoclonal antibodies, e.g. antibodies specifically recognizing an IGFR-like receptor epitope comprising the sequence

```
(i)
                                  (SEQ ID NO.: 2)
TSKRTPDGFDSVPLKT;
and/or

(ii)
                                  (SEQ ID NO.: 3)
CHQCDPDKYSE;
and/or

(iii)
                                  (SEQ ID NO.: 4)
MYKWAKPKICSEDLEG;
and/or

(iv)
                                  (SEQ ID NO.: 5)
FQRTTFHEASRKYTN
and/or

(v)
                                  (SEQ ID NO.: 6)
CTFSRNTPTRTFNY
```

The diagnostic binding agents employed in the methods of the invention may further comprise a detectable label attached to the diagnostic binding agent. The detectable label may be (preferably covalently) attached to the diagnostic binding agents either directly or via spacers of various lengths to reduce potential steric hindrance. Various methods for labelling proteins are known in the art and can be used in performing the present invention. The term "label" or "labelling group" refers to any detectable label. Suitable labels for use in with the diagnostic binding agent include, without limitation, (i) isotopic labels, which may be radioactive or heavy isotopes, such as radioisotopes or radionuclides (e.g., $^{3}H$, $^{14}C$, $^{15}N$, $^{35}S$, $^{89}Zr$, $^{90}Y$, $^{99}Tc$, $^{111}In$, $^{125}I$, $^{131}I$), (ii) magnetic labels (e.g., magnetic particles), (iii) redox active moieties, (iv) optical dyes (including, but not limited to, chromophores, phosphors and fluorophores) such as fluorescent labels (e.g., FITC, rhodamine, lanthanide phosphors), chemiluminescent labels, and fluorophores which can be either "small molecule" fluorophores or proteinaceous fluorophores, (v) enzymatic groups (e.g. horseradish peroxidase, p galactosidase, luciferase, alkaline phosphatase), (vi) biotinylated groups, (vii) predetermined polypeptide epitopes recognized by a secondary reporter (e.g., leucine zipper pair sequences, binding sites for secondary antibodies, metal binding domains, epitope tags, etc.).

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, OR), FITC, Rhodamine, and Texas Red (Pierce, Rockford, IL), Cy5, Cy5.5, Cy7 (Amersham Life Science, Pittsburgh, PA). Suitable optical dyes, including fluorophores, are described in Molecular Probes Handbook by Richard P. Haugland. Exemplary proteinaceous fluorescent labels also include, but are not limited to, green fluorescent protein, including a *Renilla, Ptilosarcus*, or *Aequorea* species of GFP, EGFP, blue fluorescent protein (BFP), enhanced yellow fluorescent protein (EYFP), luciferase, and β galactosidase.

It is within the knowledge of the skilled person to choose a suitable label depending on the type of diagnostic binding agent, its chemical properties and intended detection method. Particularly suitable diagnostic binding agents for use in the methods of the invention are monoclonal antibodies, preferably specifically recognizing the IGFR-like receptor described herein.

Advantageously, de-differentiation of pancreatic β cells can be visualized by employing diagnostic binding agents capable of specifically recognizing the IGFR-like receptor described herein. It is contemplated that de-differentiation of said β cells is indicative of diabetes, or the risk of developing diabetes, and precedes β cell dysfunction. The present invention therefore, for the first time, provides a diagnostic assay that allows diagnosis of diabetes (including type 1, type 2 gestational diabetes, metabolic syndrome and prediabetes) at a very early stage of disease onset, thus opening new possibilities for early interference with destructive mechanisms leading to β cell dysfunction and loss or impairment of insulin production.

Having found that the gene product of the human KIAA1324 gene plays a role in diabetes, the present invention allows assigning to any of the known SNPs in the KIAA1324 gene whether one or more SNPs may indeed be associated with a predisposition for developing or being at a risk of developing diabetes, in particular diabetes mellitus type II.

The present invention also allows making use of SNPs known in the human KIAA1324 gene (including exons, introns, 5'- and 3'-untranslated regions) for determining whether a subject may have a predisposition for developing or being at a risk of developing diabetes, in particular diabetes mellitus type II. Preferred SNPs for such determination are listed in the following Table.

| KIAA1324 gene on Chr. 1: SNPs positions |
|---|
| 109 660 032 |
| 109 666 403 |
| 109 672 215 |
| 109 673 020 |
| 109 678 443 |
| 109 679 027 |
| 109 680 501 |
| 109 681 567 |
| 109 683 485 |
| 109 685 870 |
| 109 686 206 |
| 109 686 758 |
| 109 687 741 |
| 109 688 390 |
| 109 688 810 |
| 109 689 620 |
| 109 692 058 |
| 109 692 601 |
| 109 697 510 |

If a subject may have at a position as listed in the above Table have another nucleotide as compared to the wild-type human KIAA1324 gene, said subject may have a predisposition for developing or being at a risk of developing diabetes, in particular diabetes mellitus type II, i.e., a SNP at a position as listed in the above Table may be indicative for a predisposition for developing or being at a risk of developing diabetes, in particular diabetes mellitus type II. The wild-type human KIAA1324 gene is the one of NCBI Gene ID 57535, updated on 15 Jul. 2015, shown as nucleotide sequence under GenBank accession number NG_032763.1.

The positions referred to in the above Table are taken from Gene ID 57535 for KIAA1324 (updated on Aug. 27, 2016), Annotation release 108, Assembly GRCh37.p13 (GCF_000001405.25), Chromosome 1, Location NC_000001.10 (109656585..109749403).

Patients

The term "patient" or "subject" as used herein refers to a human or non-human animal, generally a mammal. Particularly envisaged is a mammal, such as a rabbit, a mouse, a rat, a Guinea pig, a hamster, a dog, a cat, a pig, a cow, a goat, a sheep, a horse, a monkey, an ape or preferably a human. Thus, the methods, uses and compounds described in this document are in general applicable to both human and veterinary disease.

Treatment

The term "treatment" in all its grammatical forms includes therapeutic or prophylactic treatment. A "therapeutic or prophylactic treatment" comprises prophylactic treatments aimed at the complete prevention of clinical and/or pathological manifestations or therapeutic treatment aimed at amelioration or remission of clinical and/or pathological manifestations of the diseases. The term "treatment" thus also includes the amelioration or prevention of diabetes.

In the context with the present invention the term "therapeutic effect" in general refers to the desirable or beneficial impact of a treatment, e.g. amelioration or remission of the disease manifestations. The term "manifestation" of a disease is used herein to describe its perceptible expression, and includes both clinical manifestations, hereinafter defined as indications of the disease that may be detected during a physical examination and/or that are perceptible by the patient (i.e., symptoms), and pathological manifestations, meaning expressions of the disease on the cellular and molecular level. The therapeutic effect of treatment with the IGFR-like antagonists and agonists can be assessed using routine methods in the art, e.g., measuring insulin levels and/or glucose levels in blood samples of the patient. Additionally or alternatively, it is also possible to evaluate the general appearance of the respective patient (e.g., fitness, well-being) which will also aid the skilled practitioner to evaluate whether a therapeutic effect has been elicited. The skilled person is aware of numerous other ways which are suitable to observe a therapeutic effect of the compounds of the present invention.

Dose

Preferably, a therapeutically effective amount of the compound as described herein is administered. By "therapeutically effective amount" is meant an amount of the compound as described herein that elicits a therapeutic effect. The exact dose of IGFR-like receptor antagonists or agonists will depend on the purpose of the treatment (e.g. remission maintenance vs. treatment of acute flare of the disease), and will be ascertainable by one skilled in the art using known techniques. Adjustments for route of administration, age, body weight, general health, sex, diet, time of administration, drug interaction and the severity of the condition may be necessary, and will be ascertainable with routine experimentation by those skilled in the art.

Administration

A variety of routes are applicable for administration of the compound according to the present invention, including, but not limited to, orally, topically, transdermally, subcutaneously, intravenously, intraperitoneally, intramuscularly or intraocularly. However, any other route may readily be chosen by the person skilled in the art if desired.

Composition

It is envisaged to administer the IGFR-like antagonists or agonists in the form of a pharmaceutical composition. Preferably, said antagonists or agonists are present in the pharmaceutical composition in a therapeutically effective amount. Particularly preferred antagonists or agonists for use in the pharmaceutical composition provided herein are monoclonal antibodies specifically binding to the IGFR-like receptor described herein. Said antibodies are envisaged to specifically bind to an IGFR-like receptor epitope comprising the sequence

```
(i)
                              (SEQ ID NO.: 2)
TSKRTPDGFDSVPLKT;
and/or

(ii)
                              (SEQ ID NO.: 3)
CHQCDPDKYSE;
and/or

(iii)
                              (SEQ ID NO.: 4)
MYKWAKPKICSEDLEG;
```

-continued

```
and/or

(iv)
                              (SEQ ID NO.: 5)
FQRTTFHEASRKYTN
and/or

(v)
                              (SEQ ID NO.: 6)
CTFSRNTPTRTFNY
```

The term "pharmaceutical composition" particularly refers to a composition suitable for administering to a human, i.e., a composition that is preferably sterile and/or contains components which are pharmaceutically acceptable. However, compositions suitable for administration to non-human animals are also envisaged herein. Preferably, a pharmaceutical composition comprises an IGFR-like antagonist or agonist together with one or more pharmaceutical excipients. The term "excipient" includes fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers or tonicity modifiers. Pharmaceutical compositions of the invention can be formulated in various forms, e.g., in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for the desired method of administration.

The pharmaceutical composition of the present invention may further comprise one or more additional agents. Preferably, said agents are therapeutically effective for treatment the diseases described herein and present in the composition in a therapeutically effective amount. Examples include, without limitation, metformin, sulfonylureas, meglitinides, thiazolidinediones, DPP-4 inhibitors, GLP-1 receptor agonists, SGLT2 inhibitors, insulin and insulin derivatives (insulin glulisine, insulin lispro, insulin aspart, insulin glargine, insulin detemir, insulin isophane), and combinations thereof.

In view of the above, the present invention hence also provides a pharmaceutical composition comprising an IGFR-like antagonist or agonist. Said pharmaceutical composition is particularly intended for use in a method of therapeutic and/or prophylactic treatment of diabetes.

Kit

A kit is also provided herein. The kit may be a kit of two or more parts, and comprises the IGFR-like receptor antagonist or agonist, preferably in a therapeutically effective amount and in a pharmaceutically acceptable form. The components of the kit may be contained in a container or vials. The kit is envisaged to comprise additional agents useful in treating diabetes, as described elsewhere herein. Exemplary additional agents include, without limitation, metformin, sulfonylureas, meglitinides, thiazolidinediones, DPP-4 inhibitors, GLP-1 receptor agonists, SGLT2 inhibitors, insulin and insulin derivatives (insulin glulisine, insulin lispro, insulin aspart, insulin glargine, insulin detemir, insulin isophane), and combinations thereof.

The IGFR-like antagonist or agonist and the additional agents can be administered simultaneously or sequentially to the patient.

Screening Assay

When used herein the term "screening assay" is equivalently used with the term "screening method". Such assay or method is preferably performed "in vitro". However, it can also be performed "in vivo".

Antagonists and agonists of the IGFR-like receptor can be identified using an in vitro screening assay as provided herein, said assay comprises the following steps: (a) providing a stable cell line expressing said IGFR-like receptor; (b) contacting said cell line of (a) with a candidate antagonist or agonist; and (c) measuring an IGFR-like receptor downstream signaling event, wherein an antagonist is identified by increasing said IGFR-like receptor downstream signaling event, and an agonist is identified by decreasing said IGFR-like receptor downstream signaling event; wherein said IGFR-like receptor comprises a sequence corresponding to sequence SEQ ID No. 1.

A preferred downstream signaling event is InsR phosphorylation, AMPK phosphorylation, mTOR phosphorylation, AKT phosphorylation, ERK phosphorylation, and/or S6K phosphorylation.

Optionally, in the herein described screening methods, a cell line, preferably the same cell line as is applied in the screening methods of the present invention, expressing said IGFR-like receptor is not contacted with a candidate antagonist or agonist, respectively. Such cell line serves as control. In such a control cell line also an IGFR-like receptor downstream signaling event is measured and compared to the IGFR-like receptor downstream signaling event measured in a cell line that is (or was) contacted with a candidate antagonist or agonist.

Preferred examples of cell lines expressing said IGFR-like receptor are Min6 or PDX1+/NKX6.1+iPSC.

As described herein, IGFR-like receptor downstream signaling events are thought to result in a negative regulation of InsR- and/or IGF1R-mediated signaling, and in particular in inhibited or reduced (i) Akt phosphorylation, (ii) AMPK phosphorylation and/or (iii) mTOR phosphorylation. As such, a binding agent promoting or increasing (i) Akt phosphorylation, (ii) AMPK phosphorylation and/or (iii) mTOR phosphorylation in the screening assay provided herein is likely as an antagonist of the IGFR-like receptor. A binding agent not having any effect on or even reducing (i) Akt phosphorylation, (ii) AMPK phosphorylation and/or (iii) mTOR phosphorylation in the screening assay provided herein is likely an agonist of the IGFR-like receptor.

The stable cell line may be any cell line suitable for expressing a functional IGFR-like receptor, wherein a "functional IGFR-like receptor" is particularly envisaged to negatively regulate InsR- and/or IGF1R-mediated signaling, as ascertainable by a reduced or inhibited (i) Akt phosphorylation, (ii) AMPK phosphorylation and/or (iii) mTOR phosphorylation.

The invention also relates to an antagonist or agonist obtainable by the screening method.

The present invention also contemplates a method for detecting whether IGFR-like receptor homo- or heterodimerizes with IGFR-1, IGFR-2 and/or InsR. Said method comprises detecting whether a tagged IGFR-like receptor homodimerizes or heterodimerizes. Heterodimers may include the IGFR-like receptor and InsR, IGFR-1 and/or IGF-R2.

Preferred tags are fluorescent proteins, such as GFP or Venus, a genetic mutant of green fluorescent protein (GFP) with an emission peak of 527 nm.

Tagging the IGFR-like receptor is preferably achieved by fusing a tag in frame to said IGFR-like receptor. This may be achieved by techniques known in the art, e.g. by knocking-in the nucleotide sequence encoding said IGFR-like receptor a nucleotide sequence encoding a tag, e.g. by genome editing, such as using the CRIPSR/Cas system.

The present invention is also characterized by the following items:

1. An isolated DNA sequence encoding an IGF receptor (IGFR)-like receptor which is capable of reacting with antibodies raised against an IGFR-like receptor of SEQ ID No: 1, wherein said antibodies specifically bind to at least one epitope comprising the sequence

```
(i)
                                    (SEQ ID NO.: 2)
TSKRTPDGFDSVPLKT;
and/or

(ii)
                                    (SEQ ID NO.: 3)
CHQCDPDKYSE;
and/or

(iii)
                                    (SEQ ID NO.: 4)
MYKWAKPKICSEDLEG;
and/or

(iv)
                                    (SEQ ID NO.: 5)
FQRTTFHEASRKYTN
and/or

(v)
                                    (SEQ ID NO.: 6)
CTFSRNTPTRTFNY.
```

2. An isolated DNA sequence encoding an IGFR-like receptor comprising a sequence corresponding to SEQ ID No. 1.
3. A vector comprising the DNA sequence of any one of the preceding items.
4. The vector of item 3, further comprising a gene regulation element located upstream of the DNA sequence encoding said IGFR-like receptor.
5. A host cell comprising the vector of item 3 or 4.
6. A diagnostic binding agent capable of specifically binding to an IGFR-like receptor, said IGFR-like receptor comprising a sequence corresponding to sequence SEQ ID No 1, for use in a method of diagnosing diabetes or the risk of developing diabetes.
7. An antagonist or agonist of IGFR-like receptor, said IGFR-like receptor comprising a sequence corresponding to SEQ ID No. 1, for use as a medicament.
8. An antagonist or agonist of IGFR-like receptor, said IGFR-like receptor comprising a sequence corresponding to SEQ ID No. 1, for use in a method of prophylactic and/or therapeutic treatment of diabetes.
9. The antagonist or agonist of any one of items 7 to 8, wherein the antagonist specifically binds to said IGFR-like receptor.
10. The antagonist or agonist of any one of items 7 to 9, wherein the antagonist or agonist is selected from an antibody, a siRNA, a nucleic acid, an aptamer, a peptide, a protein, or a small molecule organic compound.
11. The antagonist or agonist of item 10, wherein the antibody comprises antibodies, antibody variants and antibody fragments.
12. The antagonist or agonist of item 10 or 11, wherein said antibody is a monoclonal or polyclonal antibody.

13. The antagonist or agonist of item 12, wherein said antibody is a monoclonal antibody which specifically binds to an epitope of said IGFR-like receptor, the epitope comprising the sequence:

```
(i)
                              (SEQ ID NO.: 2)
TSKRTPDGFDSVPLKT;
and/or

(ii)
                              (SEQ ID NO.: 3)
CHQCDPDKYSE;
and/or

(iii)
                              (SEQ ID NO.: 4)
MYKWAKPKICSEDLEG;
and/or

(iv)
                              (SEQ ID NO.: 5)
FQRTTFHEASRKYTN
and/or

(v)
                              (SEQ ID NO.: 6)
CTFSRNTPTRTFNY.
```

14. The antagonist or agonist of any one of the preceding items, wherein diabetes comprises type 1 diabetes, type 2 diabetes, gestational diabetes, prediabetes, insulin resistance, metabolic syndrome, and impaired glucose tolerance.
15. The antagonist or agonist of any one of items 8 to 15, wherein treatment prevents or reverses insulin resistance.
16. The antagonist or agonist of any one items 8 to 16, wherein treatment prevents or reverses de-differentiation of pancreatic islet cells.
17. A pharmaceutical composition comprising an antagonist or agonist of an IGFR-like receptor comprising a sequence corresponding to SEQ ID No. 1, wherein said antagonist is a monoclonal antibody that specifically binds to said IGFR-like receptor.
18. The pharmaceutical composition of item 17, wherein said antibody specifically binds to an epitope of said IGFR-like receptor, the epitope comprising sequence:

```
(i)
                              (SEQ ID NO.: 2)
TSKRTPDGFDSVPLKT;
and/or

(ii)
                              (SEQ ID NO.: 3)
CHQCDPDKYSE;
and/or

(iii)
                              (SEQ ID NO.: 4)
MYKWAKPKICSEDLEG;
and/or

(iv)
                              (SEQ ID NO.: 5)
FQRTTFHEASRKYTN
and/or

(v)
                              (SEQ ID NO.: 6)
CTFSRNTPTRTFNY.
```

19. A monoclonal antibody which specifically binds to an IGFR-like receptor epitope comprising the sequence

```
(i)
                              (SEQ ID NO.: 2)
TSKRTPDGFDSVPLKT;
and/or

(ii)
                              (SEQ ID NO.: 3)
CHQCDPDKYSE;
and/or

(iii)
                              (SEQ ID NO.: 4)
MYKWAKPKICSEDLEG;
and/or

(iv)
                              (SEQ ID NO.: 5)
FQRTTFHEASRKYTN
and/or

(v)
                              (SEQ ID NO.: 6)
CTFSRNTPTRTFNY.
```

20. An in vitro screening assay for antagonists or agonists of an IGFR-like receptor, said method comprising the steps of:
   (a) providing a stable cell line expressing said IGFR-like receptor;
   (b) contacting said cell line of (i) a candidate antagonist or agonist; and
   (c) measuring an IGFR-like receptor downstream signaling event, wherein an antagonist is identified by suppressing said IGFR-like receptor downstream signaling event, and an agonist is identified by promoting said IGFR-like receptor downstream signaling event;
   wherein said IGFR-like receptor comprises a sequence corresponding to sequence SEQ ID No. 1.
21. An IGFR-like receptor antagonist or agonist obtainable by the method of item 20, said IGFR antagonist being selected from an antibody, a siRNA, a nucleic acid, an aptamer, a peptide, a protein, or a small molecule organic compound.
22. An in vitro diagnostic assay for detection of degeneration of pancreatic islet cells in a subject, comprising the steps of:
   i) contacting a sample obtained from said subject with a diagnostic binding agent that specifically binds to IGFR-like receptor;
   ii) detecting the binding of the binding agent;
   wherein detectable binding of said diagnostic binding agent is indicative of de-differentiation of pancreatic islet cells in the subject;
   wherein the IGFR-like receptor comprises a sequence corresponding to SEQ ID No. 1.
23. The in vitro diagnostic assay of item 22, wherein de-differentiation of pancreatic islet cells is indicative of diabetes or the risk of developing diabetes.
24. The in vitro diagnostic assay of any one of item 22 or 23, wherein the sample is a plasma sample.
25. The in vitro diagnostic assay of any one of items 22 to 24, wherein the diagnostic binding agent is a monoclonal antibody.
26. A method of treating diabetes, comprising administering an IGFR antagonist to a subject, said IGFR-like receptor comprising a sequence corresponding to SEQ ID No. 1.
27. Use of an IGFR-like receptor antagonist or agonist in a method of treating diabetes, said IGFR-like receptor comprising a sequence corresponding to SEQ ID No. 1.

28. A method of generating an antibody against an epitope of an IGFR-like receptor. The antibody can be prepared by a method including the following steps: (a) administering to a mammal an antibody-generating peptide from an IGFR-like receptor as set forth in SEQ ID NO: 1, wherein the peptide comprises a sequence selected from the group consisting of SEQ ID NO: 4 and 6; and (b) purifying the antibody.
29. A binding agent which specifically binds to an IGFR-like receptor epitope as described herein, wherein said binding agent of the IGFR-like receptor includes complimentary determining regions (CDRs): CDR-H1: SYHIS (SEQ ID NO:13 or 19), CDR-H2: AISSGGDTYYNSLLKS (SEQ ID NO:14 or 20), CDR-H3: ESY (SEQ ID NO:15 or 21), CDR-L1: RASENIDTYLH (SEQ ID NO:16 or 22), CDR-L2: FASQSIS (SEQ ID NO:17 or 23), and CDR-L3: QQGNILPYT (SEQ ID NO:18 or 24); or CDR-H1: SYWMD (SEQ ID NO:25), CDR-H2: NIYPSDGETHYNQKFKD (SEQ ID NO:26), CDR-H3: LYSEYGS (SEQ ID NO:27), CDR-L1: KSSQSLLNSGNQKNYLT (SEQ ID NO:28), CDR-L2: WASTRDS (SEQ ID NO:29), and CDR-L3: QNDYSYPLT (SEQ ID NO:30).
30. A binding agent that is an antibody or a fragment thereof that binds to an IGFR-like receptor epitope, having: a variable heavy chain amino acid sequence SEQ ID NO:31, and a variable light chain amino acid sequence SEQ ID NO:32; a variable heavy chain amino acid sequence SEQ ID NO:33, and a variable light chain amino acid sequence SEQ ID NO:34, a variable heavy chain amino acid sequence SEQ ID NO:35, and a variable light chain amino acid sequence SEQ ID NO:36; a heavy chain amino acid sequence SEQ ID NO: 37, and a light chain amino acid sequence SEQ ID NO: 38; a heavy chain amino acid sequence SEQ ID NO: 39, and a light chain amino acid sequence SEQ ID NO: 40, or a heavy chain amino acid sequence SEQ ID NO: 41, and a light chain amino acid sequence SEQ ID NO: 42.

It is noted that as used herein, the singular forms “a”, “an”, and “the”, include plural references unless the context clearly indicates otherwise. Thus, for example, reference to “a reagent” includes one or more of such different reagents and reference to “the method” includes reference to equivalent steps and methods known to those of ordinary skill in the art that could be modified or substituted for the methods described herein.

Unless otherwise indicated, the term “at least” preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term “and/or” wherever used herein includes the meaning of “and”, “or” and “all or any other combination of the elements connected by said term”.

The term “about” or “approximately” as used herein means within 20%, preferably within 10%, and more preferably within 5% of a given value or range. It includes, however, also the concrete number, e.g., “about 20” includes 20.

The term “less than” or “greater than” includes the concrete number. For example, less than 20 means less than or equal to. Similarly, more than or greater than means more than or equal to, or greater than or equal to, respectively.

Throughout this specification and the claims which follow, unless the context requires otherwise, the word “comprise”, and variations such as “comprises” and “comprising”, will be understood to imply the inclusion of a stated integer or step or group of integers or steps but not the exclusion of any other integer or step or group of integer or step. When used herein the term “comprising” can be substituted with the term “containing” or “including” or sometimes when used herein with the term “having”.

When used herein “consisting of” excludes any element, step, or ingredient not specified in the claim element. When used herein, “consisting essentially of” does not exclude materials or steps that do not materially affect the basic and novel characteristics of the claim.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be had from the following examples, offered for illustrative purposes only. The examples are not intended to limit the scope of the present invention in any way.

EXAMPLES

Example 1: Material and Methods

Generation of the IGFR-Like Receptor Knockout Mice

All mice were housed in the central facilities at HMGU in accordance with the German animal welfare legislation and acknowledged guidelines of the Society of Laboratory Animals (GV-SOLAS) and of the Federation of Laboratory Animal Science Associations (FELASA). Sacrifice of mice at embryonic stages was not subject to regulatory authorization.

Targeted ES cell clones derived from C57BL/6N parental cell line JM8.N4 were obtained from the EUCOMM cell repository (EuMMCR) (Helmholtz Zentrum Muenchen GmbH, Alleles produced for the EUCOMM and EUCOMMTools projects by the Helmholtz Zentrum Muenchen GmbH (Hmgu). MGI Direct Data Submission. 2010-2015) and were injected into CD1 blastocysts for chimera generation. The resulting chimeras were mated to CD1 or C57BL/6J mice, and the progeny were screened by PCR to confirm germline transmission. Heterozygous mice carrying the targeted mutation were intercrossed to generate homozygous mutant mice either in CD1 or C57BL/6J background.

Genotyping was confirmed by PCR using genomic DNA extracted from the tails of control and knockout mice. Primers used for PCR were as follow: forward primer: 5'TGGGTAGCCTTTCTGTATGG-3' (SEQ ID NO: 8) and reverse primer: 5' GACATAGGGCAGATTTGTGG-3' (SEQ ID NO: 9).

Proliferation Assay

To assess cell proliferation in mutant embryos the pregnant females were injected subcutaneously with 0.1 mg EdU/gram body weight. After two hours, the animals were sacrificed and pancreata from E14.5, E16.5 and E18.5 embryos were dissected and fixed in 4% PFA in PBS pH7.4 overnight at 4° C. Next day the organs were subjected to a 7.5%, 15%, 30% sucrose gradient embedded in Tissue Freezing Medium (Leica, Germany) and stored at −80° C. 20 micrometer cryosections were stained using Click-iT® EdU Imaging Kit (Life Technology) according to the manufacturer's instructions including antibodies against Insulin (1:250 guinea pig Thermo Scientific; PA1-26938). Images were acquired using a Leica SP5 Confocal microscope with a 20× objective and data analysis was performed using IMARIS software (Bitplane, Switzerland).

Rt-q PCR

For gene expression analysis, by real time quantitative PCR, mRNA was isolated from pancreata of knockout and control embryos using miRNeasy™ mini kit (Qiagen, Germany). The cDNA was synthesized using GoScript™ Reverse Transcription System (Promega) and subsequently used for qPCR using TaqMan® Low Density Arrays and run on a ViiA 7 system (Applied Biosystems). The probes used are listed in table 1:

TABLE 1

| Gene symbol | Probe |
|---|---|
| Slc2a2 | Mm00446229_m1 |
| Slc30a8 | Mm00555793_m1 |
| Ucn3 | Mm00453206_s1 |
| Gjd3 | Mm00731344_s1 |
| Kcnj11 | Mm00440050_s1 |
| Abcc8 | Mm00803450_m1 |
| Smarca1 | Mm00474150_m1 |
| Mafa | Mm00845206_s1 |
| Mafb | Mm00627481_s1 |
| Foxa2 | Mm01976556_s1 |
| 18S | Hs99999901_s1 |
| Nkx2-2 | Mm00839794_m1 |
| Nkx6-1 | Mm00454962_m1 |
| Pax6 | Mm00443081_m1 |
| Pdx1 | Mm00435565_m1 |
| Neurod1 | Mm01946604_s1 |
| Glp1r | Mm00445292_m1 |
| Gcgr | Mm00433546_m1 |
| Gipr | Mm01316344_m1 |
| Prlr- | Mm00599957_m1 |
| Insr | Mm01211875_m1 |
| Insrr | Mm00442243_m1 |
| B9d1 | Mm00840045_m1 |
| Il6ra | Mm00439653_m1 |
| Cntfr | Mm00516693_m1 |
| Ffar1 | Mm00809442_s1 |
| Lgals3bp | Mm00478303_m1 |
| Sstr3 | Mm00436695_s1 |
| 1700009P17Rik | Mm00512620_m1 |
| Pard6a | Mm01247370_g1 |
| Atf2 | Mm00833804_g1 |
| Dvl3 | Mm00432914_m1 |
| Fzd3 | Mm00445423_m1 |
| Rhoa | Mm00834507_g1 |
| Rock1 | Mm00485745_m1 |
| Rock2 | Mm01270843_m1 |
| Wnt5b | Mm01183986_m1 |
| Gck | Mm00439129_m1 |
| Pcsk1 | Mm00479023_m1 |
| Pcsk2 | Mm00500981_m1 |
| Ccnd1 | Mm00432359_m1 |
| Ccnd2 | Mm00438070_m1 |
| Cdk4 | Mm00726334_s1 |
| Cdkn1a | Mm04205640_g1 |
| Cdkn1b | Mm00438168_m1 |

TABLE 1-continued

| Gene symbol | Probe |
|---|---|
| Actb | Mm00607939_s1 |
| Rplp0 | Mm00725448_s1 |

Generation of Monoclonal Antibody Against Estrogen-Induced Gene 121 Protein (EIG).

Peptides from human EIG protein were synthesized and coupled to OVA (Peps4LS, Heidelberg, Germany). Lou/c rats or C57BL/6 mice were immunized subcutaneously and intraperitoneally with a mixture of 50 μg peptide-OVA, 5 nmol CPG oligonucleotide (Tib Molbiol, Berlin), 500 μl (mouse 100 μl) PBS and 500 μl (mouse 100 μl) incomplete Freund's adjuvant. A boost without adjuvant was given six weeks after the primary injection. Fusion was performed using standard procedures. Supernatants were tested in a differential ELISA with the biotinylated EIG peptides and an irrelevant biotinylated peptide on avidin coated ELISA plates. MAbs that reacted specifically with the EIG peptide were further analyzed in Western blot.

The rabbit polyclonal antibodies were purchased from Pineda Antikörper Service, Berlin, Germany.

Cell Culture

Min6 is a pancreatic β-cell line which is well characterized for their ability to secret insulin upon glucose stimulation. This cell line was from Susumu Seino's Lab.

Min6 cells were maintained in high glucose Dulbecco's modified Eagle medium of Gibco (41966-052) supplemented with 10% fetal bovine serum (FBS), 1% Penicillin/Streptomycin and 2-mercaptoethanol.

HEK293 cells were purchased from the global biosource center ATCC.

IGFR-Like Receptor Knock-Down

Min6 cells were seeded at a cell density of $5\times10^4$ cells/$cm^2$ and cultured in high glucose DMEM medium. After one transfection of IGFR-like receptor siRNA at day two and day three, cells were lysed in RIPA buffer on ice at day 4 at a cell density of 50-60%. The lipofectamin (Lipofectamine™ 2000, Life Technologies, #11668019) based transfection was performed according to the protocol of Life Technologies and 200 pmol of following siRNA from Dharmacon GE Healthcare were used: On-Target plus mouse 5330417C22Rik (229722) siRNA-SMARTpool L-048745-01-0020 and control siRNA On-target plus non-targeting siRNA #1 D-001810-01-20.

IGFR-Like Receptor Knock-Out

Figure 23:
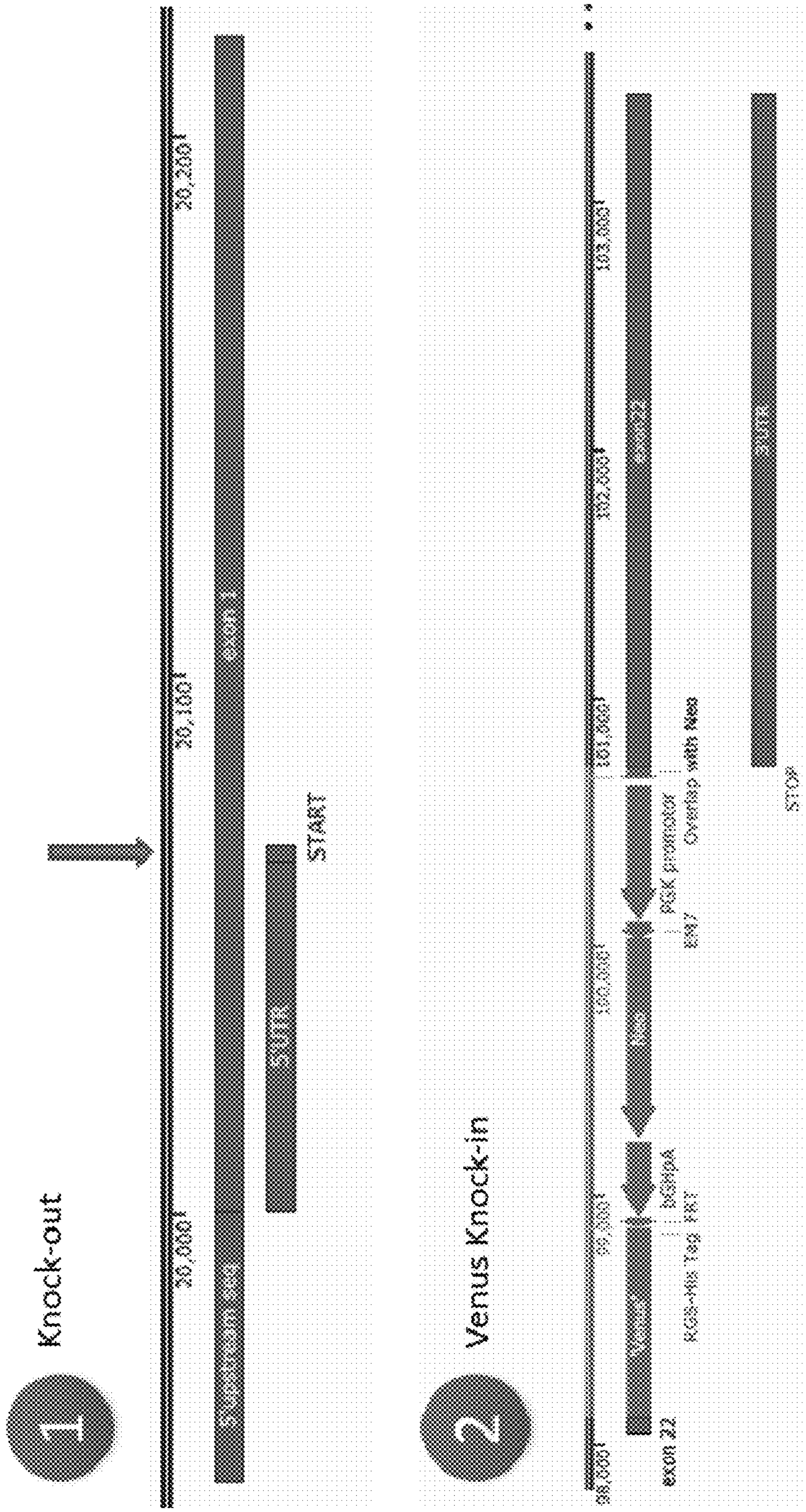
FIG. 23: IGFR-like receptor knock-out and knock-in strategy to study receptor function in cell culture and mice. (1) Schematic representation of the CRISPR/Cas9-mediated knock-out strategy that targets the core promoter and transcriptional start side. (2) Schematic representation of the CRISPR/Cas9-mediated knock-in fusion of Venus fluorescent reporter by removing the translational stop sequence and fusing Venus in-frame to IGFR-I open-reading frame. The IGFR-I gene lies on mouse Chromosome 3 108455694-108536536.

CRISPR/Cas9-mediated IGFR-I knock-out strategy in Min6 cells that targets the core promoter and transcriptional start side (FIG. 23).

IGFR-Like Receptor Knock-In Venus Fusion

CRISPR/Cas9-mediated knock-in fusion of Venus fluorescent reporter by removing the translational stop sequence and fusing Venus in-frame to IGFR-I open-reading frame (FIG. 23): A Cas9 fused in frame to the Venus fluorescent reporter was co-transfected in Min6 cells with guidance RNAs (gRNAs) flanking the transcriptional start side of IGFR-I. After 2 days fluorescent cells are flow sorted and limited dilutions are plated on 10 cm dishes. After 10-14 days single clones were picked on 96-well plates and analyzed for IGFR-I expression (staining and WB) and internal deletion by genomic PCR.

Starvation Assay Min6

Min6 cells were seeded at a cell density of $5\times10^4$ cells/$cm^2$ and cultured in high glucose DMEM medium. After performing a IGFR-like receptor knock-down Min6 cells were washed six times with 1×PBS and HBSS buffer containing 0.2% BSA was added for 15 min, 30 min, 60 min and 120 min to starve the cells. Subsequently, cells were lysed in RIPA buffer on ice.

Western Blot (Semi-Dry Immunoblotting)

Cells and tissues were lysed in RIPA buffer (50 mM Tris pH7.5, 150 mM NaCl, 1 mM EDTA, 1% IGEPAL, 0.1% SDS, 0.1% Na deoxycholate) containing a cocktail of proteinase inhibitor (1:100, Sigma, P8340) and phosphatases inhibitors (1:100, Sigma Aldrich, #2 P0044 and #3 P5726) and the cell or tissue lysates were cleared by centrifugation at 13000 r.p.m. for 10-30 min. The proteins (10-20 μg) were resolved in 6.5-15% SDS-PAGE according to the protein size to be detected and transferred to a PVDF membrane. Primary antibodies were added to the membrane in 5% milk and incubated at 4° C. overnight. Protein bands were visualized on Hyperfilms™ (GE healthcare, 28906837) or Blaufilme™ CEA-RP (Ernst Christiansen GmbH, EC84A) by chemiluminescent detection (ECL, Millipore, WBKLS0500).

The following antibodies were used with corresponding dilutions:

IGFR-like receptor SEQ ID No. 2 (1:5000 rabbit Pineda, Berlin, Germany), IGFR-like receptor SEQ ID No. 2 (1:100 rat and mouse), IGFR-like receptor SEQ ID No. 4 and 6 (1:10 rat and mouse), Akt (1:5000 Cell Signaling, 4691), P-Akt (1:5000 Cell Signaling, 4060), Erk (1:5000 Cell Signaling, 4695), P-Erk (1:5000 Cell Signaling, 4370), m-Tor (1:1000 Cell Signaling, 2972), P-mTor (1:1000 Cell Signaling, 5536), Ampk (1:1000 Cell Signaling, 2532), P-Ampk (1:2500 Cell Signaling, 2535), IRS-2 (1:1000 Cell Signaling, 4502), IRβ (1:1000 Cell Signaling, 3025), S6rp (1:5000 Cell Signaling, 2217S), P-S6RP (1:5000 Cell Signaling, 2211S), P-IR/IGFR (1:1000, Millipore, 07-841), α-Tubulin (1:5000, Sigma, T7451), mouse Adaptin beta clone 74 (1:5000, BD Bioscience 610382). For the detection of autophagy related proteins the Autophagy Antibody Sampler Kit (#4445, 1:1000) of Cell Signaling was used.

Immunofluorescence and Imaging

For immunocytochemistry, Min6 cells were plated in Ibidi (Munich, Germany) 8-well chamber dishes (treated) at a cell density of $5\times10^4$ cells/well. Three days after seeding cells were directly fixed with 4% PFA for 10 min followed by a 10 min incubation in permeabilization solution (0.1 M Glycine, 0.2% Triton-X100 in 1×PBS). After blocking (10% donkey serum, 1% BSA and 5% FCS, 0.5% Tween-20 in 1×PBS) for 1 h, cells were incubated in blocking solution containing primary antibodies overnight at 4° C.: IGFR-like receptor Seq ID No. 2 (rat and mouse 1:10), GM130 (1:300, BD, 610822), IGF2R (1:100 ThermoScientific, PA3-850). The following secondary antibodies were applied for 2 h at room temperature in blocking solution: donkey anti-rabbit IgG-555 (1:800, Invitrogen, A31572), donkey anti-mouse IgG-488 (1:800, Invitrogen, A21202), and donkey anti-rat IgG 647 (1:400, Dianova, 712-605-150). After DAPI staining (50 ng/ml), the samples were mounted with Elvanol™ and images were acquired on a Leica laser-scanning SP5 confocal microscope with 63× objective.

For immunohistochemistry in mouse tissue, pancreata were dissected and fixed in 4% PFA in PBS for 2 h at 4° C., cryoprotected in a gradient series of sucrose solutions (7.5, 15 and 30% sucrose in PBS) for at least 2 h in each solution and finally the organs were embedded in Tissue Freezing medium (Leica 14020108926) and stored at −80° C. 20 μm sections were used for immunostaining. Briefly the sections were washed in PBS, permeabilized in 0.1% Triton X-100, 0.1M Glycine in PBS for 15 minutes and then blocked in blocking solution (10% FCS, 3% Donkey serum, 0.1% BSA and 0.1% Tween-20 in PBS) for 1 h at room temperature. Primary antibodies were diluted in blocking solution and incubated over night at 4° C. Next day the sections were washed three times for 5 minutes each in PBST (0.1% Tween-20 in PBS) incubated in secondary antibodies diluted in blocking solution for 3-5 h at room temperature, stained with DAPI (4', 6-diamidin-2-phenylindol) and mounted in embedding medium (ProLong™ Gold antifade embedding medium, Life Technologies).

For whole-mount staining of the human islets, the islets were fixed in 4% PFA in PBS for 15 min at RT and directly incubated overnight at 4° C. with primary antibodies diluted in blocking solution followed by three washes in PBST and then incubated with secondary antibodies for 3-5 hours at RT as above.

For staining of human tissue sections snap frozen pancreata pieces from human donors were embedded in Tissue Freezing medium (Leica 14020108926) and stored at −80° C. 10 μm thick section sections were fixed in in 4% PFA in PBS for 20 min at RT, washed 2 times with PBS and permeabilized for 5 min on ice. Antibodies staining procedure was performed as described above.

Primary antibodies used were anti-IGFR-like receptor rabbit SEQ ID No 2 1:100, anti-IGFR-like receptor SEQ ID No:2 and SEQ ID No. 4 rat 1:10, IGFR-like receptor SEQ ID No:2 and SEQ ID No. 6 mouse 1:10, anti-Insulin (Rabbit 1:250; Cell Signaling; 3014), anti-Insulin (Guinea pig 1:250; Thermo Scientific; PA1-26938), anti-E-Cadherin (Rat 1:500; DECMA Kremmer;) anti-Mannose 6P receptor (Rabbit 1:200; Thermo Scientific; PA3-850) and anti-Urocortin 3 (Rabbit 1:300; Phoenix Pharmaceuticals; H-019-29). Secondary antibodies used were Anti-Rabbit Alexa-555 (1:800; Invitrogen; A31572), Anti-Rabbit Alexa-488 (1:800; Invitrogen; A21206), Anti-Rat Alexa-488 (1:800; life technologies, A-21208), Anti-Rat Alexa-647 (1:800; Dianova, 712-605-150) and Anti-Guinea Pig Alexa647 (1:800; Dianova; 706-495-148) Anti-mouse Alexa-555 (1:800; Invitrogen; A31570). Pictures were taken on a Leica DMI 6000 microscope.

Immunoprecipitation Assay

For immunoprecipitation assay Min6 cells were starved for 15, 30, 60 and 120 minutes in HBSS with 0.2% BSA fatty acids free and lysed in immunoprecipitation buffer (2% CHAPS, 50 mM HEPES pH 7.5, 200 mM NaCl, 2 mM EDTA) containing a cocktail of proteinase inhibitor (1:100, Sigma, P8340) for 20 minutes on ice. The lysates were cleared by centrifugation for 30 min at 14000 rpm and 4° C. Approximately 500 μg whole cell lysates was incubated with an IGFR-like receptor SEQ ID No 2 antibody generated in rat and diluted 1:10 for 1 h at 4° C. followed by an incubation with protein G Sepharose 4 Fast Flow (GE Healthcare) for 16 h at 4° C. The precipitates were washed 5 times with immunoprecipitation buffer, denatured at 95° C. for 5 min in 2×SDS sample buffer (100 mM Tris-HCL, 4% SDS, 20% glycerol, 0.2% bromphenol blue) containing 100mMDTT and 5% 2-mercaptoethanol and subjected to Western blot analysis.

Surface Biotinylation Assay

Min6 cells were incubated with 2 mM EZ-Link® Sulfo-NHS-LC-Biotin (Thermo Scientific) in PBS pH 8.0 for 10 min at room temperature after which the biotinylation reaction was stopped with 100 mM glycine in PBS. The cells were then washed in ice cold PBS and lysed in RIPA buffer containing a cocktail of proteinase inhibitor. After clearing by centrifugation at 14000 rpm and 4° C. for 30 minutes the supernatants were incubated overnight at 4° C. with NeutrAvidin™ beads (Thermo Scientific/Pierce). The next day, after washing 5 times in RIPA buffer, the biotin labeled proteins were eluted from the beads by boiling in 2×SDS sample buffer containing 100 mM DTT and 5% 2-mercaptoethanol and subjected to Western blot analysis.

Example 2: Expression of IGFR-Like Receptor Adjacent to IGF-1, IGF-2 and Insulin Ligands in the Pancreas Briefly, E14.5 mouse embryos were obtained and subjected to in situ hybridization (ISH) using GenePaint™ (Tecan).

Gene paint in situ hybridization of the E14.5 mouse embryos shows specific expression of the IGFR-like receptor mRNA in the pancreas (FIG. 2B). IGF1 and IGF2 mRNA is expressed in tissues adjacent to the pancreatic epithelium (FIG. 2A,C) whereas Insulin mRNA is present in the endocrine compartment of the pancreas (FIG. 2D).

Example 3: IGFR-Like Receptor Knockout Mice

IGFR-like receptor knockout mice were generated as described in Example 1.

IGFR-like receptor KO Mice show normal appearance at birth but do not feed as shown by lack of milk in their stomach (FIG. 3B, stars), they are lethargic and display respiratory distress. Mendelian ratios at different stages show normal distribution of the three genotypes until birth however the percentage of surviving knockout mice is significantly reduced after birth and until the weaning age. Only few survivors are found at the weaning age probably due to compensatory mechanisms and/or splicing around the inserted cassette leading to incomplete knockout (FIG. 3C). Histogram depicting normal body weight of knock-out mice in comparison with the wild type and heterozygous littermates control at P0 (FIG. 3D).

Example 4: Growth, Proliferation and Endocrine Differentiation in the Pancreas of IGFR-Like Receptor KO Mice Briefly, IGFR-like receptor knockout mice were generated and pancreata were dissected and subjected to immunohistochemistry using antibodies against insulin. Cell proliferation was determined using EdU. A detailed description of the materials and methods used is provided in Example 1.

Figure 4:
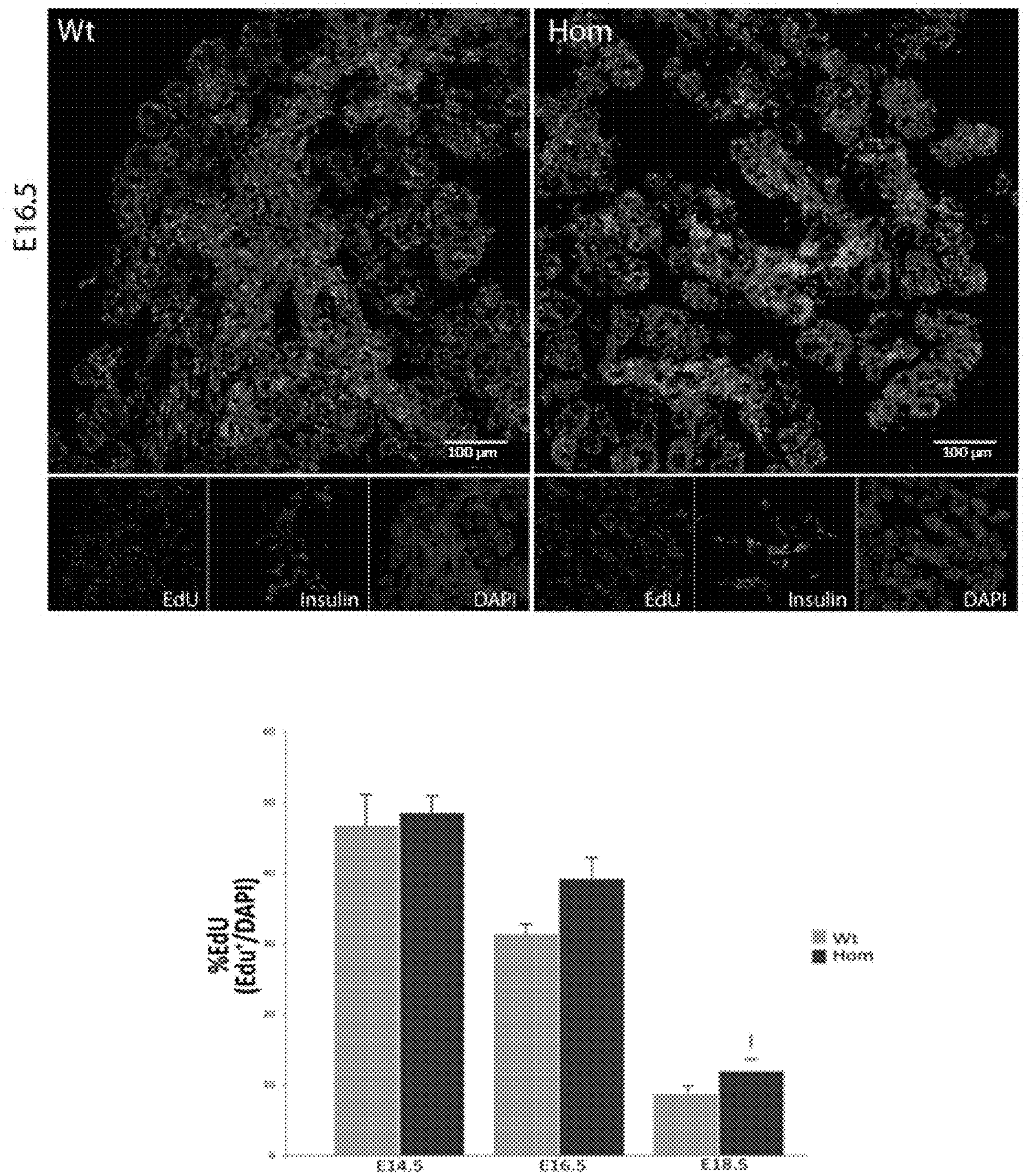
FIG. 4: Growth, proliferation and endocrine differentiation in the pancreas of IGFR-like receptor KO mice. Confocal images of pancreas sections shows normal endocrine differentiation at E16.5 as shown by immunofluorescence labeled β-cells using insulin antibodies (green) (similar results were obtained at E14.5 and E18.5 not shown). Normal proliferation of pancreatic epithelium as shown by incorporation of EdU (red). Quantification of EdU positive cells relative to total cell number (stained by DAPI) at E14.5, E16.5 and E18.5 shows no significant differences in proliferation between knockout and wild type pancreata (at least three sections from different regions of one pancreas/stage were counted, error bars represent standard error of the mean (SEM)).

Confocal images of pancreas sections show normal endocrine differentiation at E16.5 as shown by immunofluorescently labeled β-cells using insulin antibodies (green) (Similar results were obtained at E14.5 and E18.5 not shown). Normal proliferation of pancreatic epithelium as shown by incorporation of EdU(red). Quantification of EdU positive cells relative to total cell number (stained by DAPI) at E14.5, E16.5 and E18.5 shows no significant differences in proliferation between knockout and wild type pancreata. (At least three sections from different regions of one pancreas/stage were counted, error bars represent standard error of the mean) (FIG. 4).

Example 5: Pancreatic Gene Expression in IGFR-Like Receptor KO Mice Before Birth Briefly, IGFR-like receptor knockout mice were generated as described previously. Pancreata of KO mice and wild-type controls before and after birth were dissected, mRNA was isolated and real time quantitative PCR was performed. A detailed description of the materials and methods used is provided in Example 1.

Figure 5:
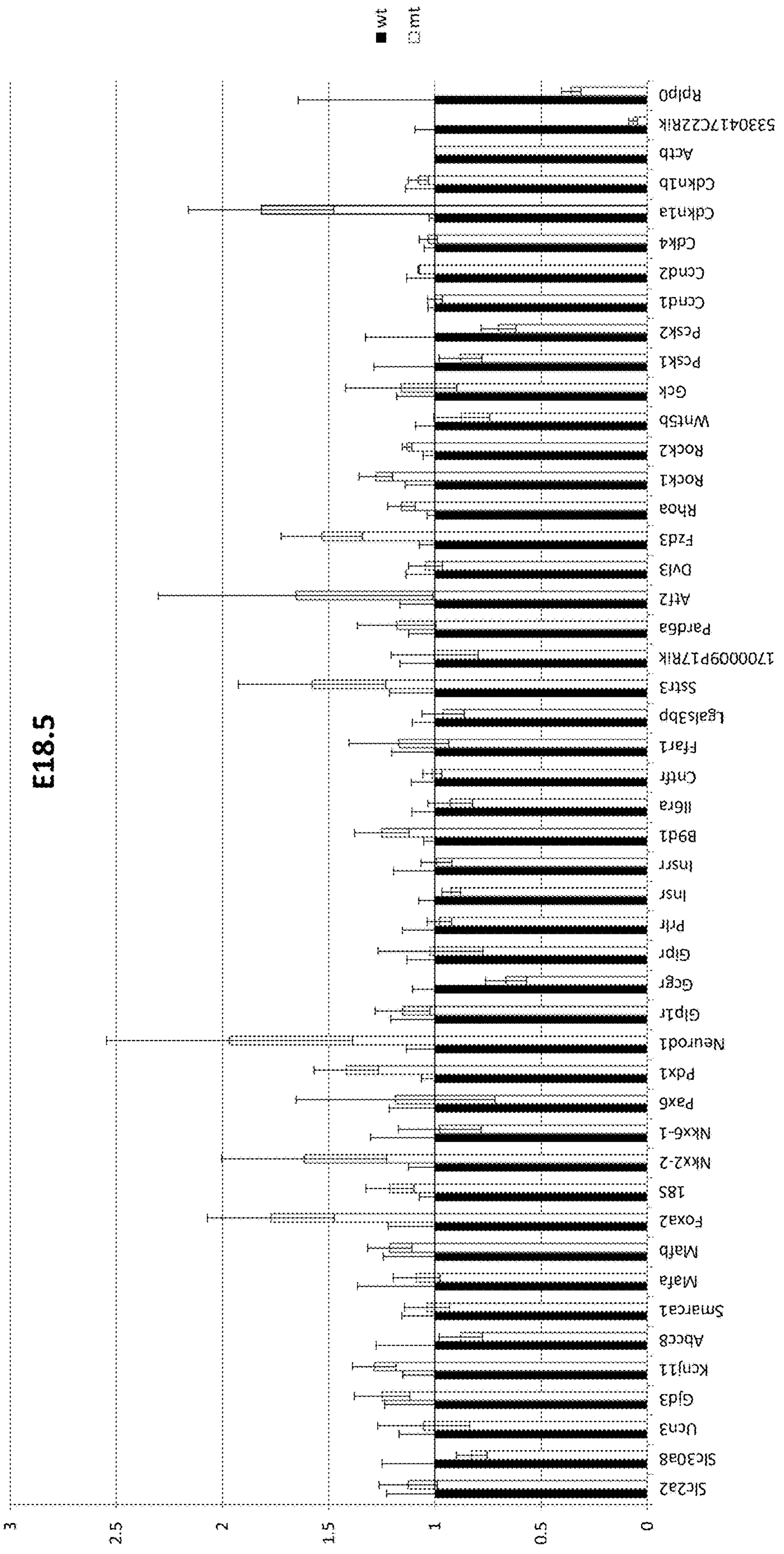
FIG. 5: Pancreatic gene expression in IGFR-like receptor KO mice before birth. Real time qPCR shows moderate changes in relative mRNA expression of selected genes important for endocrine β-cell differentiation, maturation, proliferation and function in the knockout pancreas when compared with the wild type control at E18.5. At this stage embryos still rely on maternal nutrition. (N=4, error bars represent SEM). Actin was used as a housekeeping gene for normalization.
Figure 6:
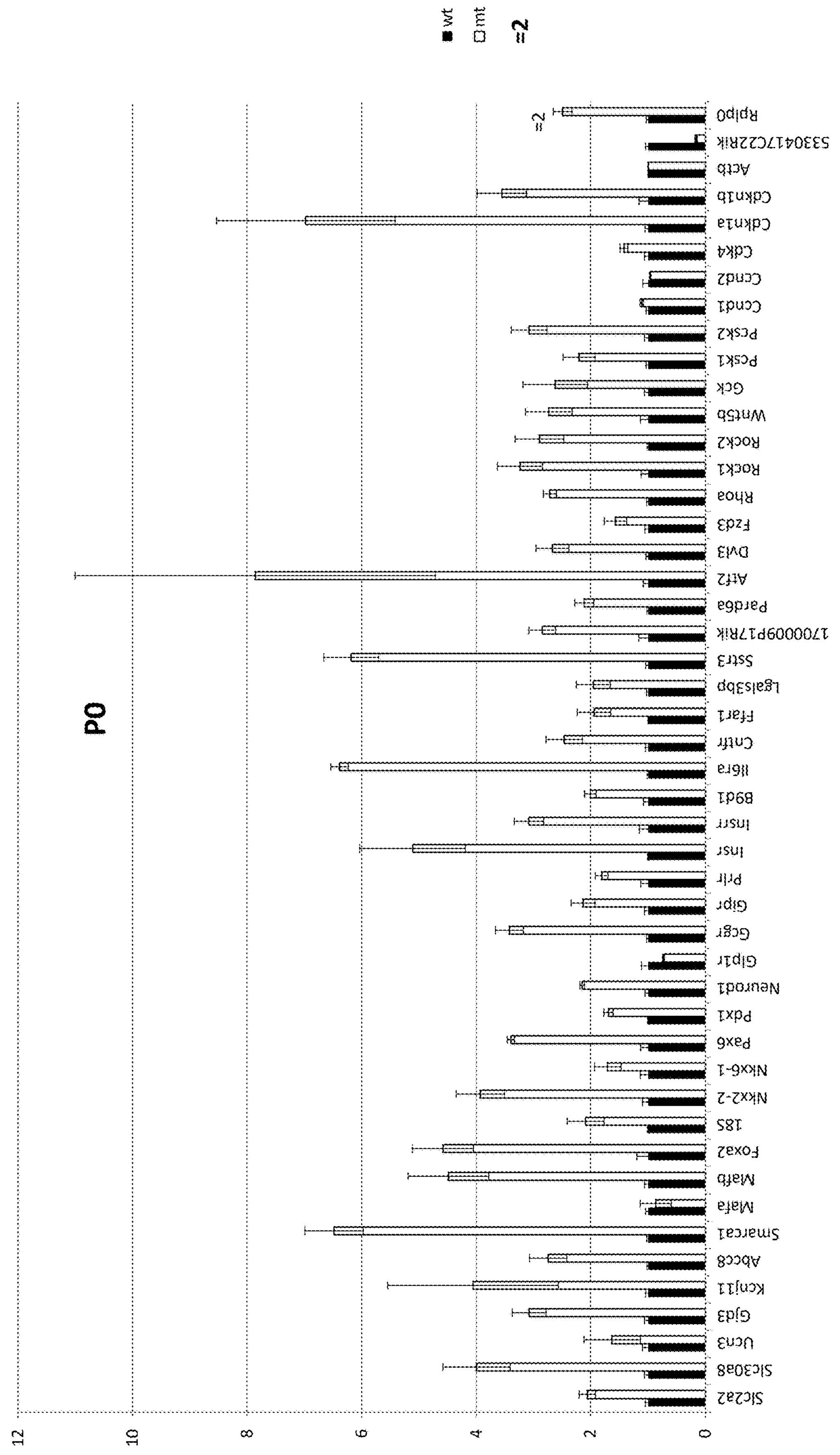
FIG. 6: Changes in pancreatic gene expression in IGFR-like receptor KO mice after birth when placental nutrient supply is interrupted and InsR-A switches to InsR-B. Relative mRNA expression of selected genes important for endocrine β-cell differentiation (Foxa2, Pdx1, Pax6, Neurod1, Nkx2-2, Nkx6-1), maturation (MafA, MafB, Ucn3), proliferation (Ccnd1, Ccnd2, Cdk4, Cdkn1a, Cdkn1b) and function (Slc2a2, Slc30a8, Gjd3, Kcnj11, Smarca1, Abcc8) are significantly changed in the knockout pancreas when compared with the wildtype control immediately after birth as shown by real time qPCR. (N=2 error bars represent SEM)

Real time qPCR shows moderate changes in relative mRNA expression of selected genes important for endocrine β-cell differentiation, maturation, proliferation and function in the knockout pancreas when compared with the wild type control at E18.5. At this stage embryos still rely on maternal nutrition (FIG. 5). Actin was used as a housekeeping gene for normalization. Relative mRNA expression of selected genes important for endocrine β-cell differentiation (Foxa2, Pdx1, Pax6, Neurod1, Nkx2-2, Nkx6-1), maturation (MafA, MafB, Ucn3), proliferation(Ccnd1, Ccnd2, Cdk4, Cdkn1a, Cdkn1b) and function(S1c2a2, Slc30a8, Gjd3, Kcnj11, Smarca1, Abcc8) are significantly changed in the knockout pancreas when compared with the wildtype control immediately after birth as shown by real time qPCR (FIG. 6).

Example 7: IGFR-Like Receptor Mediated Akt and AMPK Signaling in the Pancreas and Min6

Briefly, IGFR-like receptor knockout mice were generated and pancreata were dissected. Min6 cells were cultured and harvested as described previously. IGFR-like receptor knockdown in Min6 cells was accomplished by transfection with siRNA targeting IGFR-like receptor mRNA or scrambled siRNA as a control. Cells and tissues were subjected to by Western blotting using phospho-specific antibodies against Akt and AMPK. A detailed description of the materials and methods used is provided in Example 1.

Figure 7:
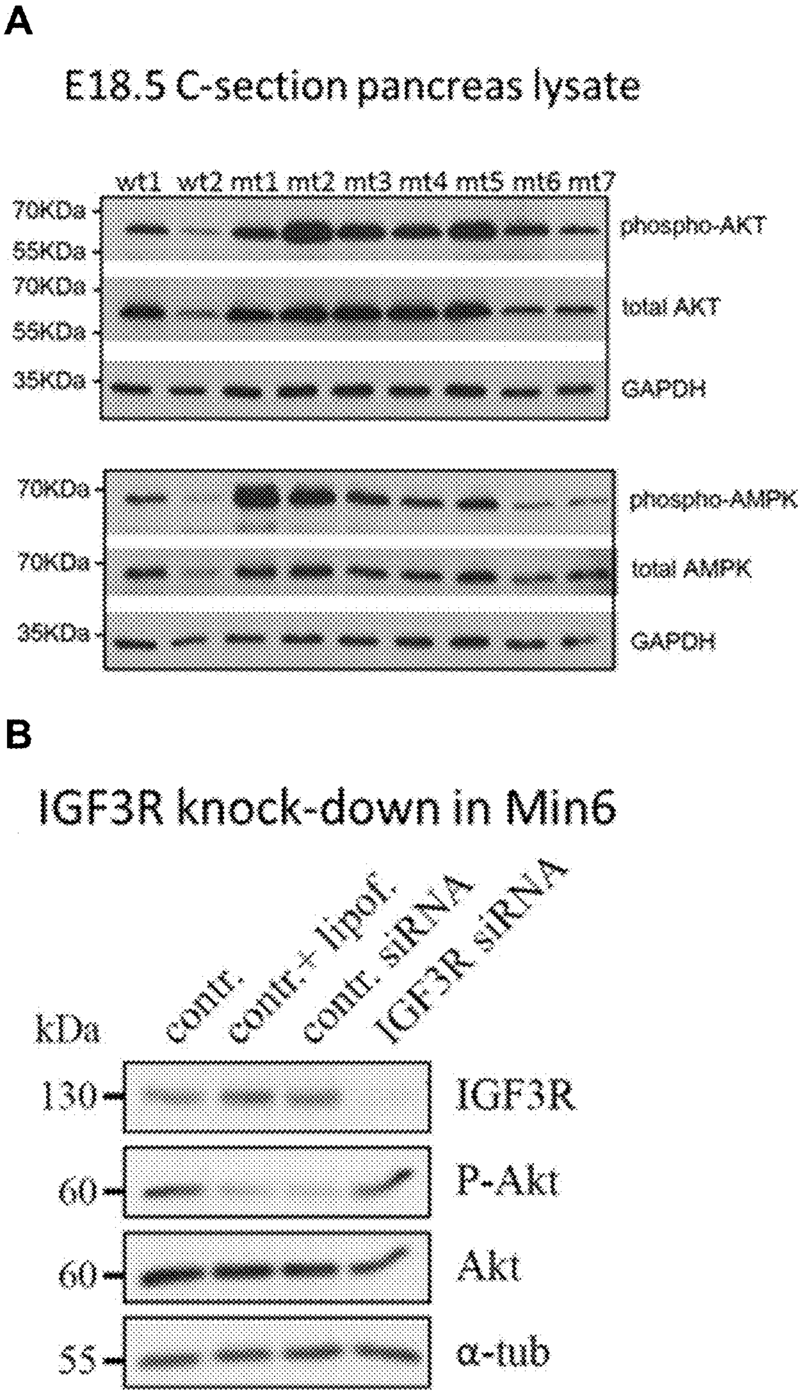
FIG. 7: IGFR-like receptor mediated Akt and AMPK signaling in the pancreas and Min6 mouse insulinoma cells. Western blotting of whole pancreas tissue lysates shows Akt and AMPK phosphorylation using phospho-specific antibodies (A). Significant number of mutant embryos show increase in Akt (mt 2, 3, 5, 6) and in AMPK phosphorylation (mt 1, 2, 3) (A). Similarly in (B) knockdown of IGFR-like receptor in Min6 cells leads to increased Akt phosphorylation as shown by Western blotting. Min6 cells were transfected with siRNA targeting IGFR-like receptor mRNA or scrambled siRNA as a control.

Western blotting of whole pancreas tissue lysates shows Akt and AMPK phosphorylation using phospho-specific antibodies (FIG. 7A). Significant number of mutant embryos show increase in Akt (mt2, 3, 5, 6) and in AMPK phosphorylation (mt1, 2, 3) (FIG. 7A). Similarly in (FIG. 7B) knockdown of IGFR-like receptor in Min6 cells leads to increased Akt phosphorylation.

Example 8: Influence of Knockdown of IGFR-Like Receptor on Insulin/IGF Signaling in Min6

Briefly, Min6 cells were cultured and transfected with siRNA targeting of IGFR-like receptor siRNA and investigated by Western blotting using phospho-specific antibodies against IR/IGF1R as well as phospho-specific antibodies against downstream signaling molecules AKT, mTOR, ERK and S6RP. A detailed description of materials and methods used is provided in Example 1.

Figure 8:
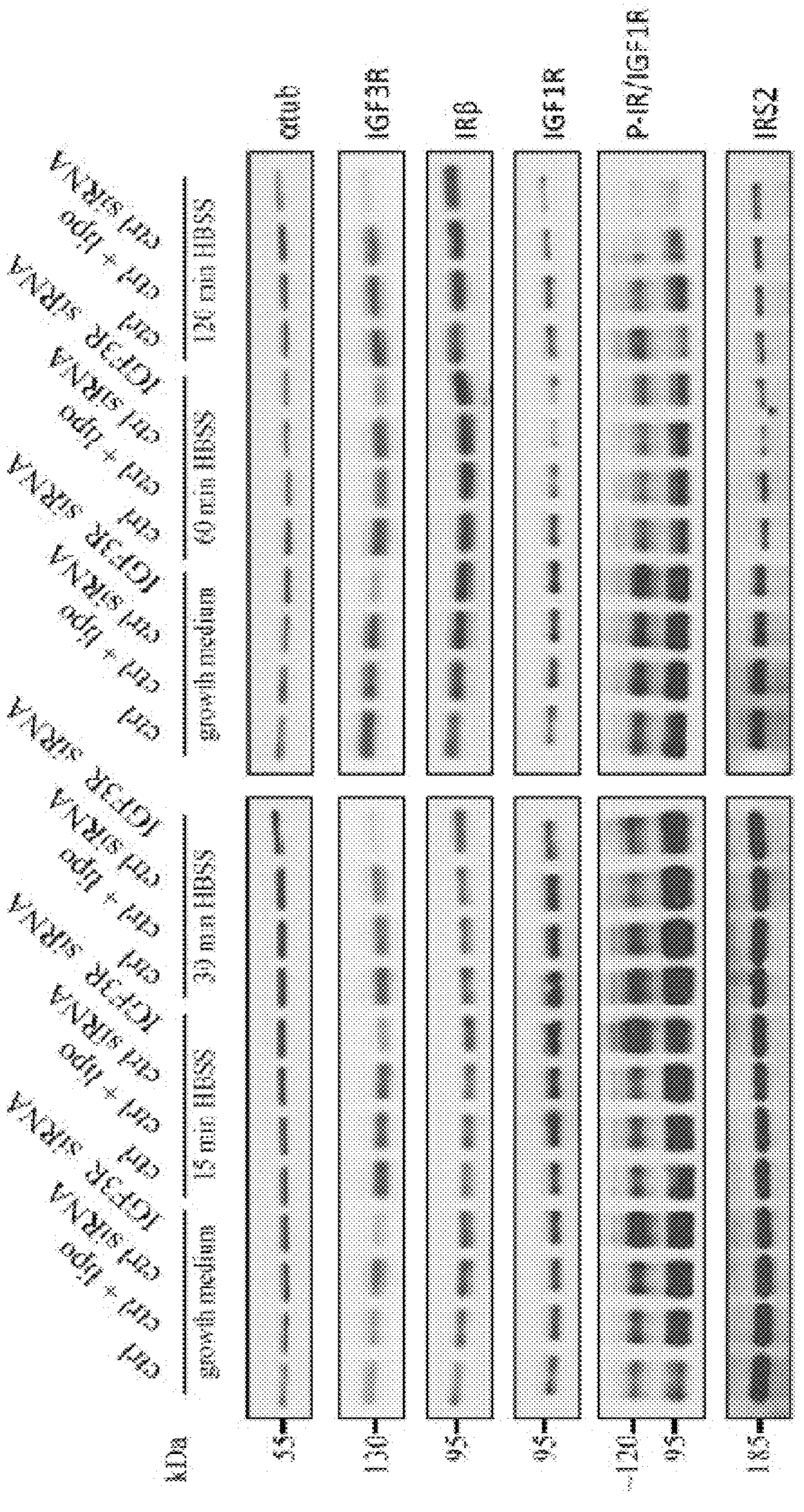
FIG. 8: Influence of knockdown of IGFR-like receptor on insulin/IGF signaling in Min6 cells. Knock down of IGFR-like receptor in Min6 insulinoma cells results in increased phosphorylation of IR/IGF1R under normal growth condition and seems to be independent of starvation conditions as shown by Western blotting using phospho-specific antibodies against IR/IGF1R. Total levels of IR and IGF1R as well as IRS-2 (an adaptor molecule downstream of IR signaling) are unchanged whereas IGFR-like receptor is strongly reduced in the knock-down samples confirming the efficiency of siRNA knockdown (A). Western blotting analysis of downstream signaling molecules such as AKT and mTOR, which are important molecules commonly phosphorylated as a consequence of IR activation. IGFR-like receptor knock-down in Min6 cells leads to increased phosphorylation of Akt and mTOR but not of ERK and S6RP. Starvation conditions, as shown by time dependent reduction of phospho-S6RP, seem to not have an impact on Akt, mTOR and ERK phosphorylation in IGFR-like receptor knock-down samples when compared with their time matched controls (B).
Figure 8:
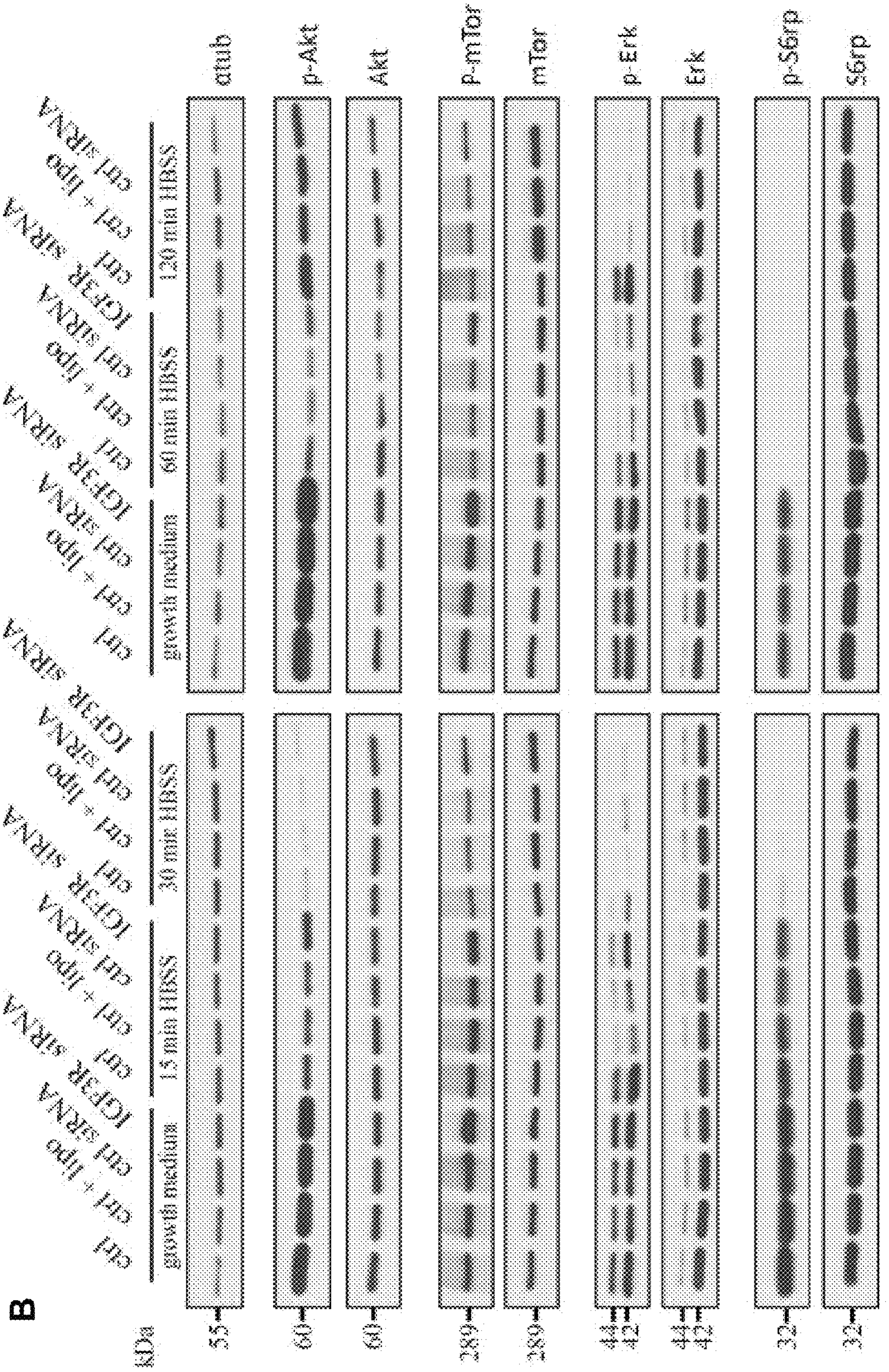

Knock down of IGFR-like receptor in Min 6 cells results in increased phosphorylation of IR/IGF1R under normal growth condition and seems to be independent of starvation conditions. Total levels of IR and IGF1R as well as IRS-2 (an adaptor molecule down stream of IR signaling) are unchanged whereas IGFR-like receptor is strongly reduced in the knockdown samples confirming the efficiency of siRNA knockdown (FIG. 8A). Western blotting analysis of downstream signaling molecules such as AKT and mTOR which are important molecules commonly phosphorylated as a consequence of IR activation indicated that IGFR-like receptor knockdown in Min6 cells leads to increased phosphorylation of Akt and mTOR but not of ERK and S6RP. Starvation conditions, as shown by time dependent reduction of phospho-S6RP, seem to not have an impact on Akt, mTOR and ERK phosphorylation in IGFR-like receptor knockdown samples when compared with their time matched controls (FIG. 8B).

Example 9: IGFR-Like Receptor Localization in Endocrine, Ductal and Exocrine Cells in the Pancreas Briefly, E18.5 pancreata were dissected and subjected to immunohistochemistry using antibodies against IGFR-like receptor, insulin and E-Cadherin. A detailed description of materials and methods used is provided in Example 1.

Figure 9:
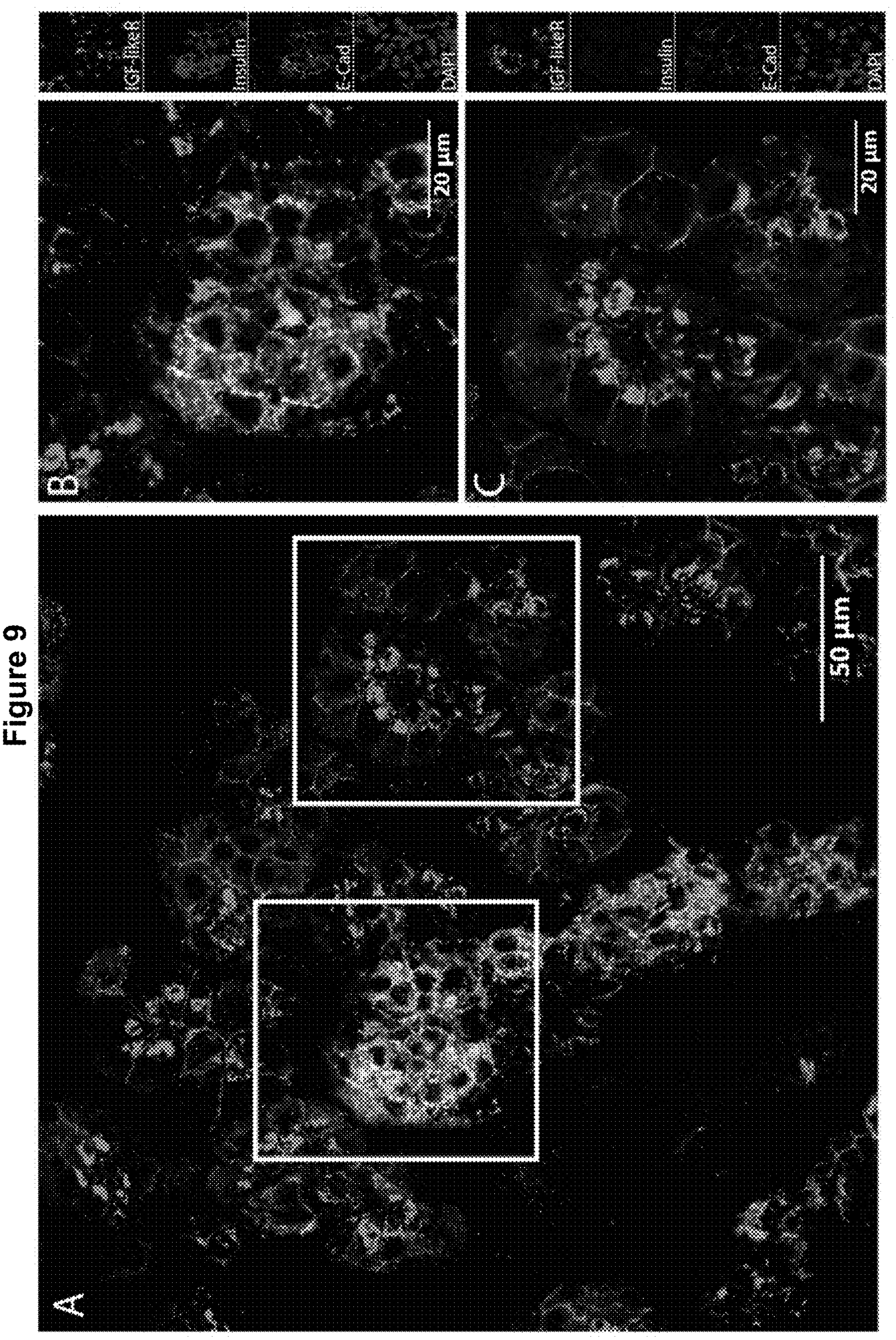
FIG. 9: IGFR-like receptor localization in endocrine, ductal and exocrine cells in the pancreas. Confocal images of E18.5 pancreas sections stained with antibodies against IGFR-like receptor (green), insulin antibodies (red) and E-Cadherin (cyan) show immunolocalization of IGFR-like receptor in both exocrine and endocrine compartment where it partially co-localizes with insulin. Nuclei where stained with DAPI.

Confocal images of E18.5 pancreas sections stained with antibodies against IGFR-like receptor (green), insulin antibodies (red) and Ecadherin(cyan) show immunolocalization of IGFR-like receptor in both exocrine and endocrine compartment where it partially co-localizes with insulin (FIG. 9). Nuclei where stained with DAPI.

Example 10: Subcellular Localization of IGFR-Like Receptor

Briefly, Min6 cells were cultured as described previously and subjected to immunocytochemistry using antibodies against IGFR-like receptor and GM130. A detailed description of materials and methods used is provided in Example 1.

Example 11: Subcellular Localization of the IGFR-Like Receptor

Briefly, immunofluorescence staining and imaging was performed as described in Example 1.

Figure 10:
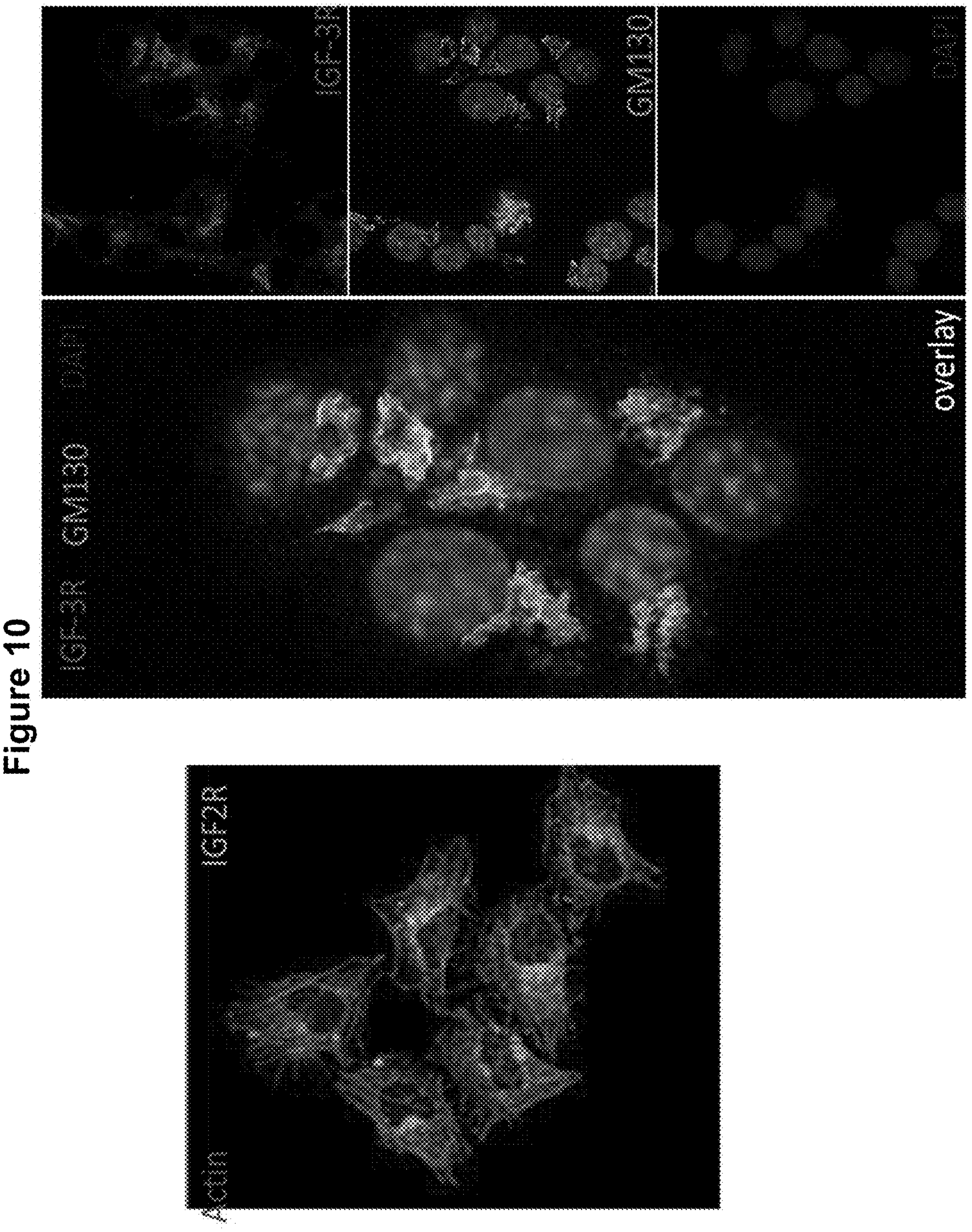
FIG. 10: IGFR-like receptor subcellular localization in Min6 cells. Immunofluorescence images of Min6 cells stained with antibodies against IGFR-like receptor and GM130, a Golgi marker, shows partial localization of the IGFR-like receptor in the Golgi complex similarly to IGF2R.
Figure 11:
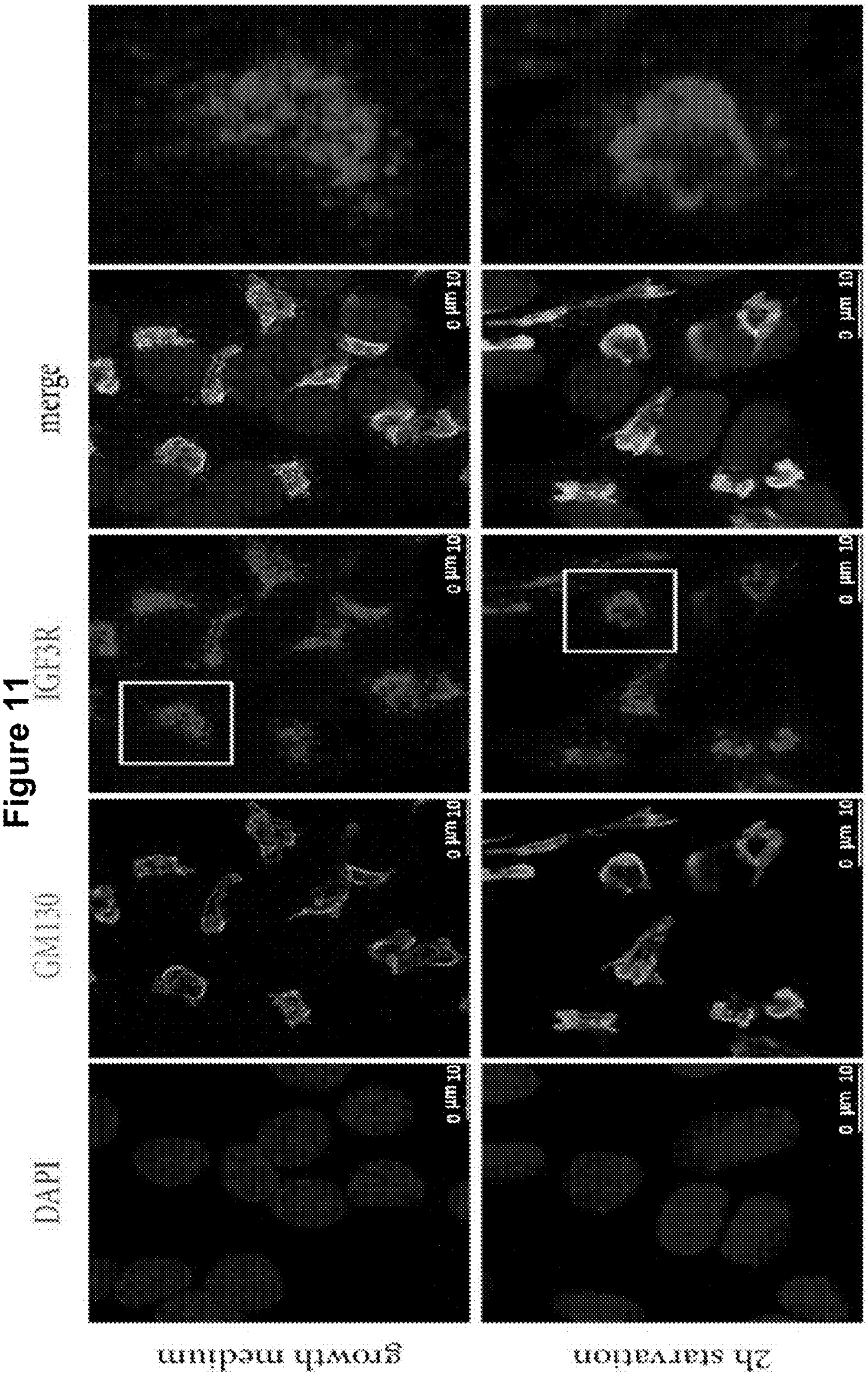
FIG. 11: IGFR-like receptor localization upon starvation. Confocal images of Min6 cells immunofluorescence labeled with IGFR-like receptor (red) and GM130 (green) show a redistribution of IGFR-like receptor concentrated in the cis-Golgi area after 2 h of starvation when compared with normal growth conditions.

Immunofluorescence images of Min6 cells stained with immunofluorescently labeled antibodies against IGFR-like receptor and GM130, a Golgi marker, shows partial localization of the IGFR-like receptor in the Golgi complex similarly to IGF2R(FIG. 10, FIG. 11).

After 2 h of starvation, a redistribution of IGFR-like receptor concentrated in the cis-Golgi area compared to normal growth conditions can be observed (FIG. 11).

Example 11: Interaction of IGFR-Like Receptor with AP-2 Under Starvation Conditions Briefly, Min6 cells were cultured as described previously and subjected to immune precipitation and western blotting using antibodies against IGFR-like receptor and Adaptin β (a subunit of the AP2 complex). A detailed description of materials and methods used is provided in Example 1.

Figure 13:
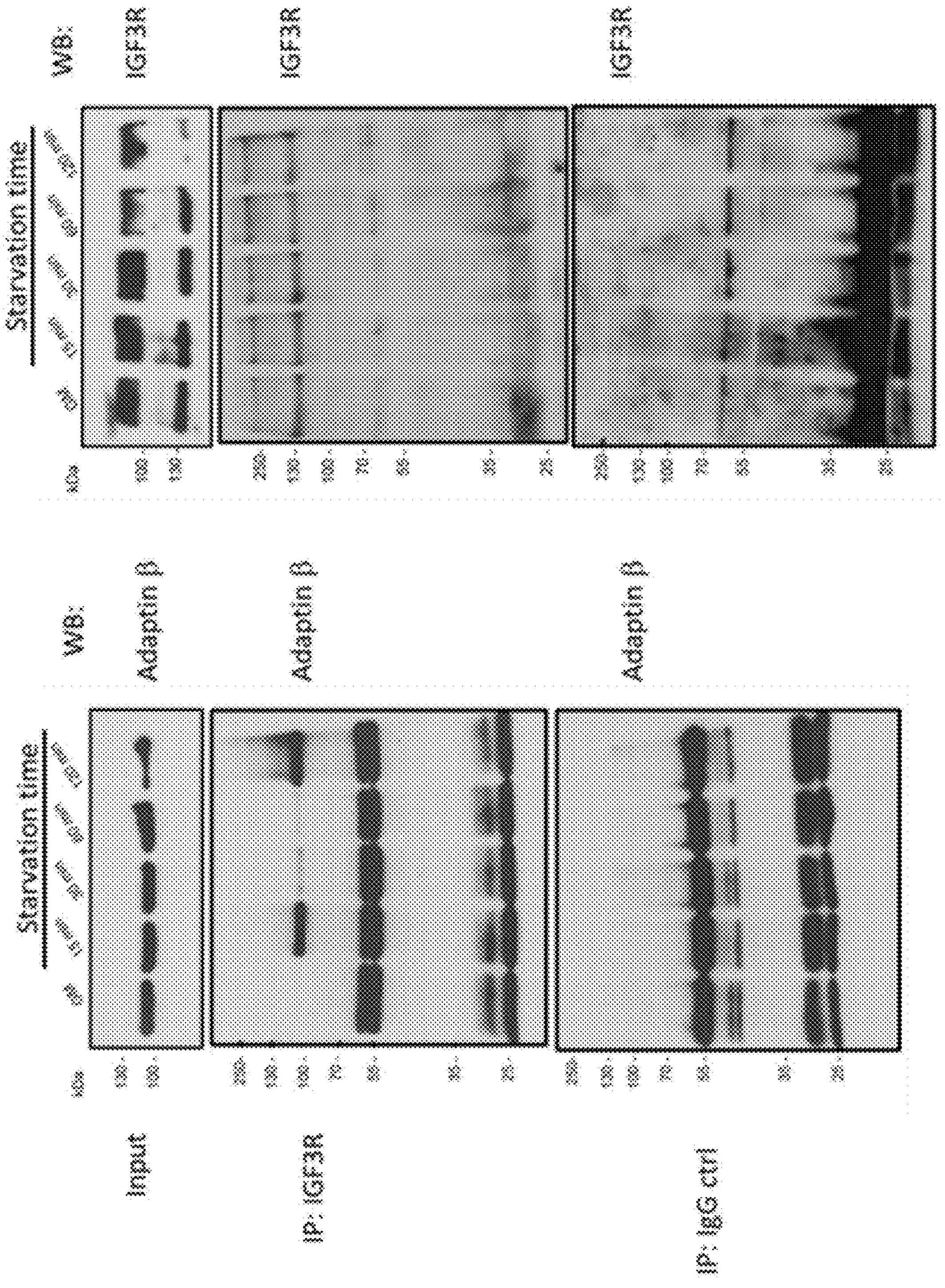
FIG. 13: Interaction of IGFR-like receptor with AP-2 under starvation conditions. Western blot analysis shows co-immunoprecipitation of the Adaptin b subunit (part of the AP2 complex) together with IGFR-like receptor in Min6 cells upon starvation as demonstrated by immunoprecipitation using an antibody against IGFR-like receptor and Adaptin b. Virtually no Adaptin b was co-precipitated under normal starving conditions.

Western blot analysis shows co-immunoprecipitation of Adaptin β subunit (part of the AP2 complex) together with IGFR-like receptor in Min6 cells upon starvation as demonstrated by immunoprecipitation using an antibody against IGFR-like receptor and Adaptin β. Virtually no Adaptin β was co-precipitated under normal starving conditions (FIG. 13).

Example 12: IGF3R but not InsR is Transported into the Cell Upon Nutrient Deprivation Briefly, Min6 cells were cultured as described previously and subjected to surface biotinylation and western blotting using antibodies against IGFR-like receptor and Adaptin β (a subunit of the AP2 complex). A detailed description of materials and methods used is provided in Example 1.

Figure 14:
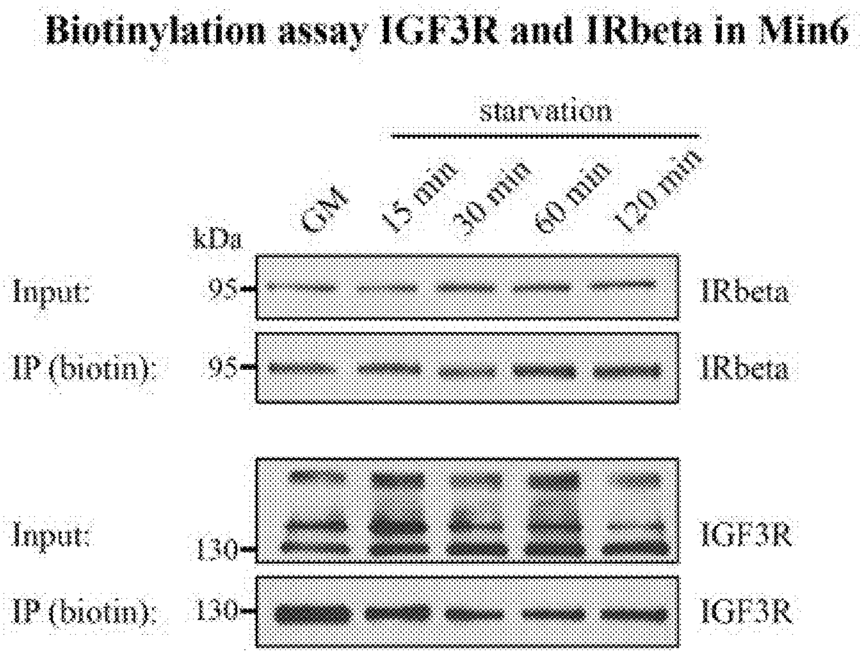
FIG. 14: IGFR-like receptor but not InsR is transported into the cell upon nutrient deprivation. Surface biotinylation followed by neutravidin pulldown and Western blotting demonstrates a time dependent reduction in surface expression of IGFR-like receptor reduction but no reduction of IR in Min6 cells under starvation conditions.

Surface biotinylation followed by neutravidin pulldown and Western blotting demonstrates a time dependent reduction in surface expression of IGFR-like receptor reduction but no reduction of IR in Min6 cells under starvation conditions (FIG. 14).

Example 14: Effect of IGFR-Like Receptor Knockdown on Expression of Autophagy Related Proteins Briefly, Min6 cells were cultured and transfected as described previously and subjected to western blotting using antibodies against ATG16L1, ATG7, ATG3, Beclin-1, LC3A/B and ATG5 (i.e. autophagy related proteins). A detailed description of materials and methods used is provided in Example 1.

Figure 15:
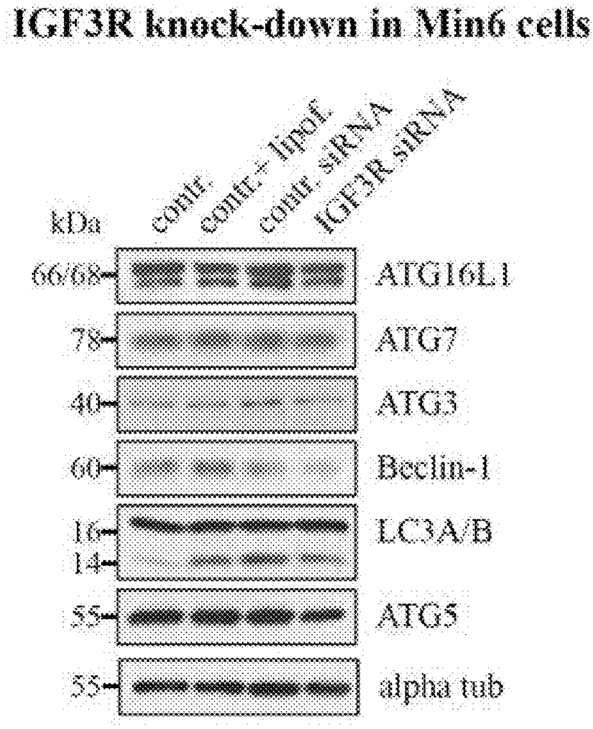
FIG. 15: IGFR-like receptor knockdown most likely does not change protein expression of autophagy related proteins in basal condition. Western blotting analysis of autophagy related molecules show no apparent changes in expression upon IGFR-like receptor knockdown in Min6 cells under normal growth conditions.

IGFR-like receptor knockdown most likely does not change protein expression of autophagy related proteins in basal condition. Western blotting analysis of autophagy related molecules show no apparent changes in expression upon IGFR-like receptor knockdown in Min6 cells under normal growth conditions (FIG. 15).

Example 15: Expression of IGFR-Like Receptor in Mouse Diabetic Islets and Exocrine Tissue Briefly, pancreata of wt and diabetic mice were dissected and subjected to immunocytochemistry using antibodies against IGFR-like receptor, insulin and E-cadherin. A detailed description of materials and methods used is provided in Example 1.

Figure 16:
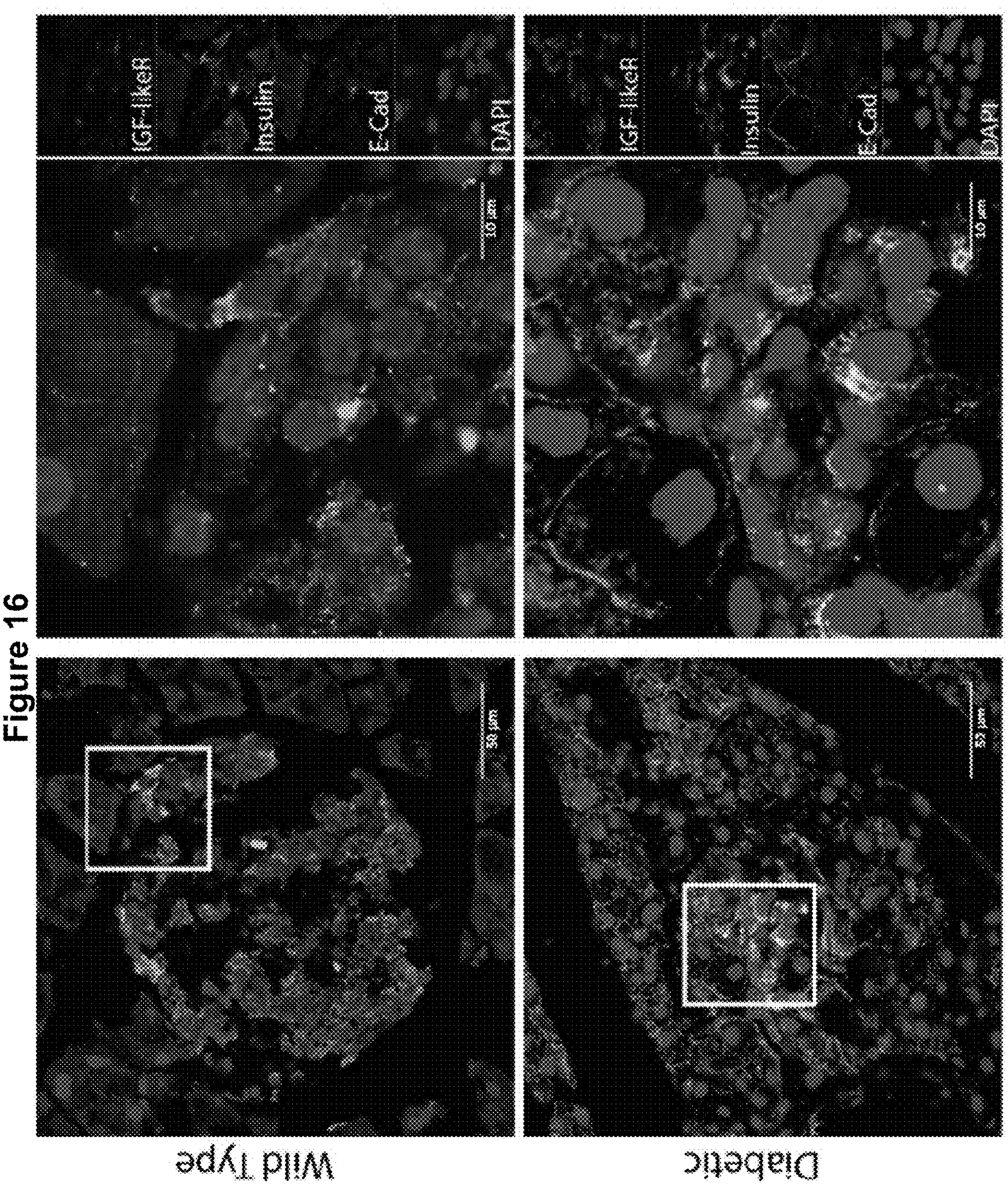
FIG. 16: Expression of IGFR-like receptor in mouse diabetic islets and exocrine tissue. LSM images of wild type (<120 mg/dL glucose) and diabetic (>500 mg/dL glucose) adult pancreata, stained with antibodies against IGFR-like receptor (red), insulin (cyan) and E-Cadherin (green) (A) and IGFR-like receptor (red), glucagon (cyan) and Urocortin3 (green) (B), show increased immunoreactivity of IGFR-like receptor antibodies in diabetic pancreas in both endocrine and exocrine compartments. Diabetic status was demonstrated by reduced insulin and Urocortin3 staining in diabetic pancreas. Right images represent higher magnification of regions marked with the white squares.
Figure 16:
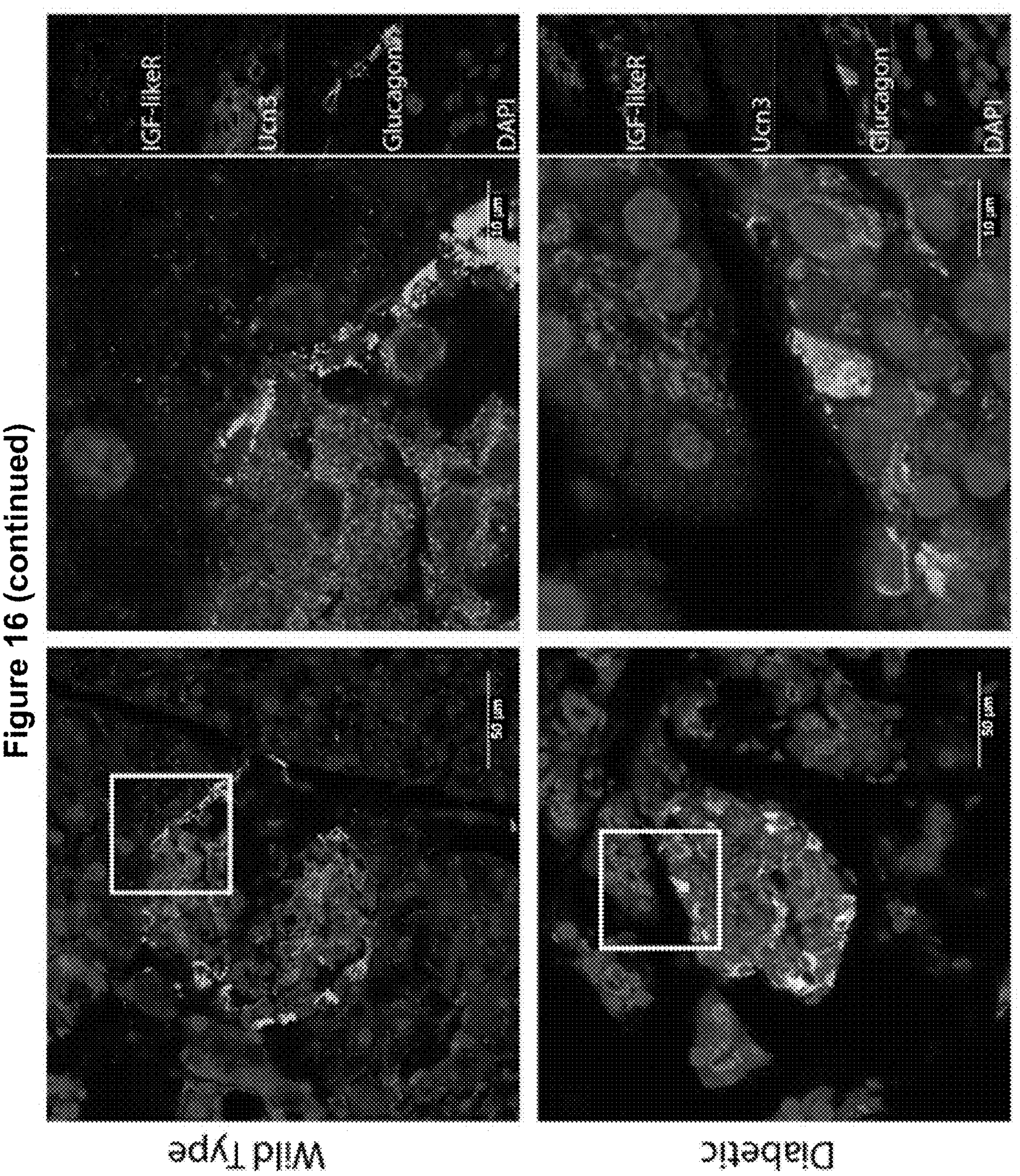

LSM images of wild type(<120 mg/dL glucose) and diabetic (>500 mg/dL glucose) adult pancreata, stained with antibodies against IGFR-like receptor (red), insulin (cyan) and E-cadherin (green) (A) and IGFR-like receptor (red), glucagon (cyan) and urocortin (green) (B), show increased immunoreactivity of IGFR-like receptor antibodies in diabetic pancreas in both endocrine and exocrine compartments. Diabetic status was demonstrated by reduced insulin and urocortin3 staining in diabetic pancreas (FIG. 16).

Example 16: Detection of IGFR-Like Receptor in Islet Cells Using Antibody Against Extracellular Domain of IGFR-Like Receptor Briefly, HEK293 cells were cultured and human islet cells were obtained as described previously. Pancreata from wt, heterozygous and mutant (IGFR-like receptor knockout) mice were dissected. Cells and tissue were subjected to Western blotting using anti IGFR-like receptor antibodies recognizing SEQ ID NO: 2, 4 and 6.

Figure 17:
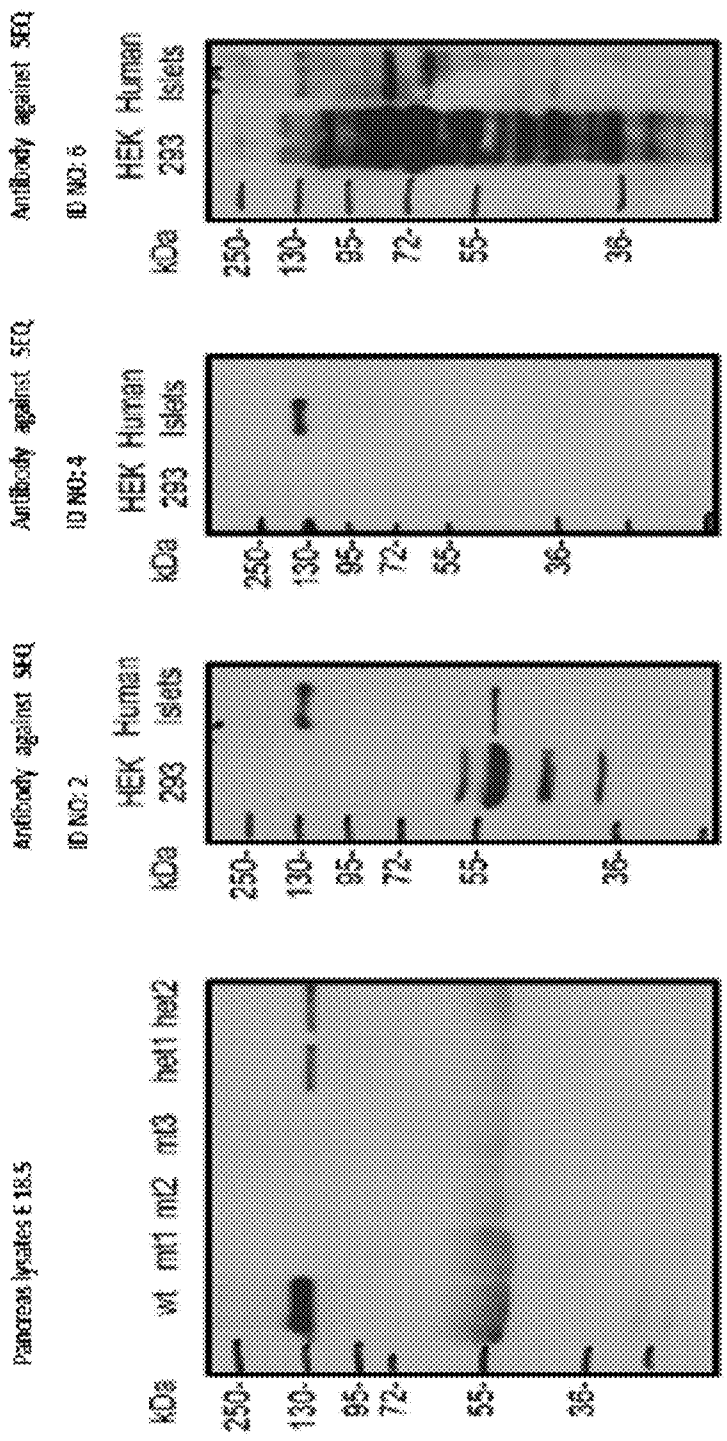
FIG. 17: Detection of IGFR-like receptor in islet cells using antibody against intracellular and extracellular domain of IGFR-like receptor. Western blotting experiments shows specific recognition of a protein band of ~130 kDa in islet cell lysates which is absent in HEK cells lysates by an antibody against the extracellular domain SEQ ID NO4 and NO 6. By comparison the same band is recognized specifically by the antibody against the intracellular domain SEQ ID NO 2 in total pancreas lysates of wild type and heterozygous but not in mutant embryos as well as in islet cells but not in HEK cells.

Western blotting experiments shows specific recognition of a protein band of ~130 kDa in islet cell lysates which is absent in HEK293 cells lysates by an antibody against SEQ ID NO: 4 and NO: 6. By comparison the same band is recognized specifically by the antibody against SEQ ID NO 2 in total pancreas lysates of wild type and heterozygous but not in mutant embryos as well as in islet cells but not in HEK cells (FIG. 17).

Example 17: IGFR-Like Receptor Distribution in Human Islets of Langerhans

Briefly, human islets were obtained and subjected to immunocytochemistry using antibodies against IGFR-like receptor, IGF2R and Insulin. A detailed description of materials and methods used is provided in Example 1.

Figure 18:
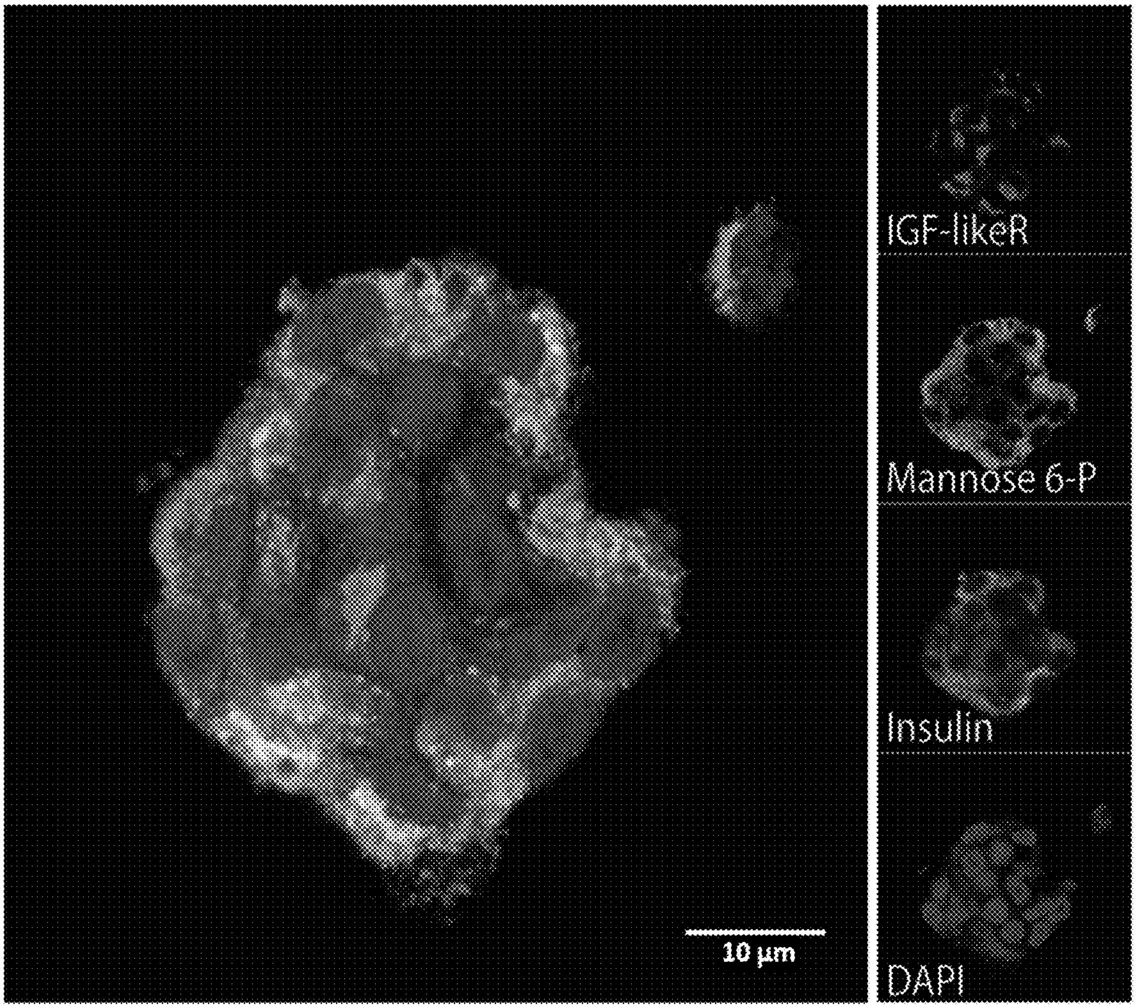
FIG. 18: IGF3R expression in human islets of Langerhans. Confocal images of Islets of Langerhans from human donor immunofluorescently labeled with antibodies against IGFR-like receptor (red), IGF2R (M6PR) (green) and Insulin (cyan) show typical IGFR-like receptor distribution in the Golgi compartment and partial co-localization with IGF2R and insulin.
Figure 19:
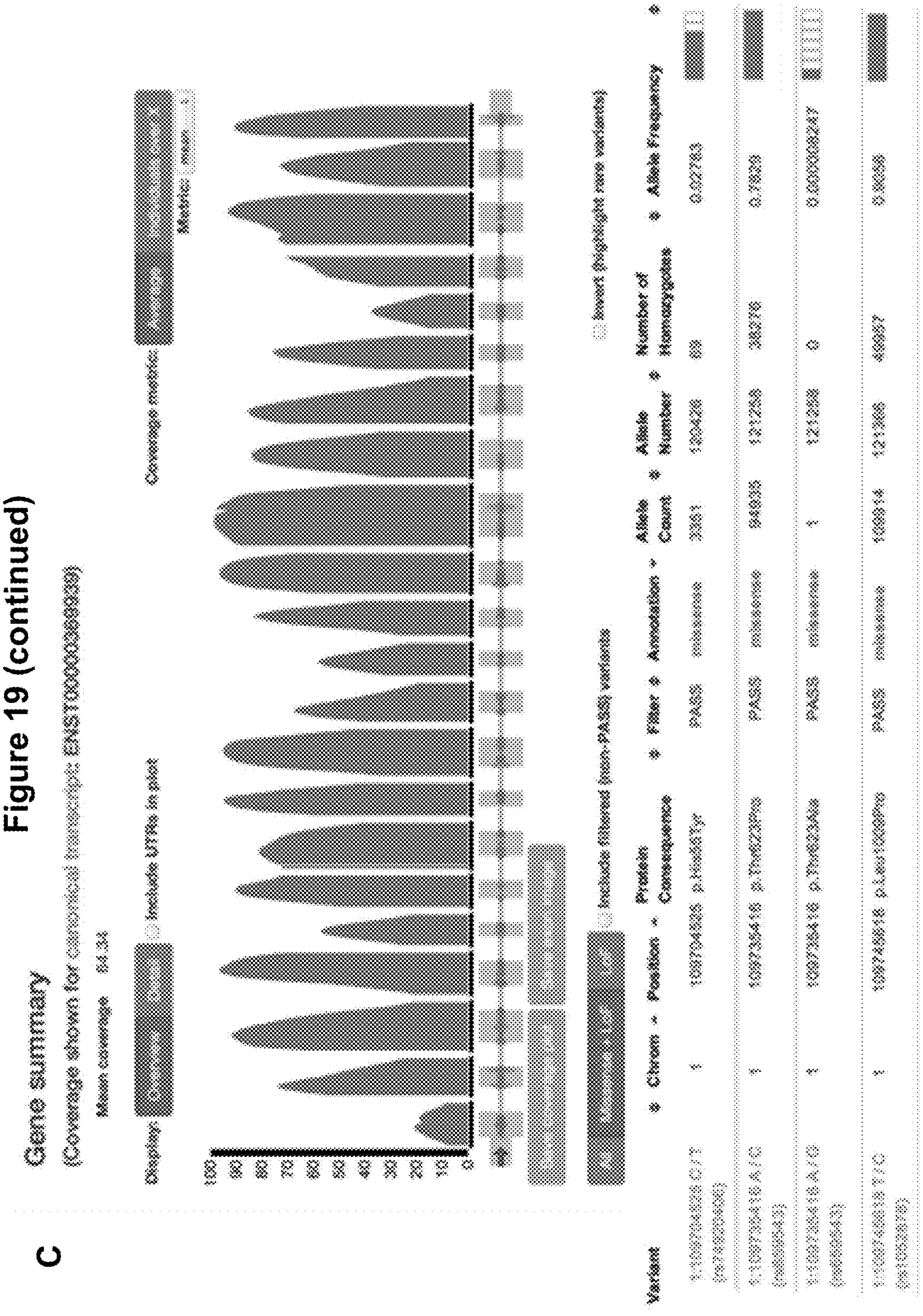
FIG. 19: KIAA1324/IGFR-like coding SNPs in extracellular domain, CRD, and CTD.
Figure 21:
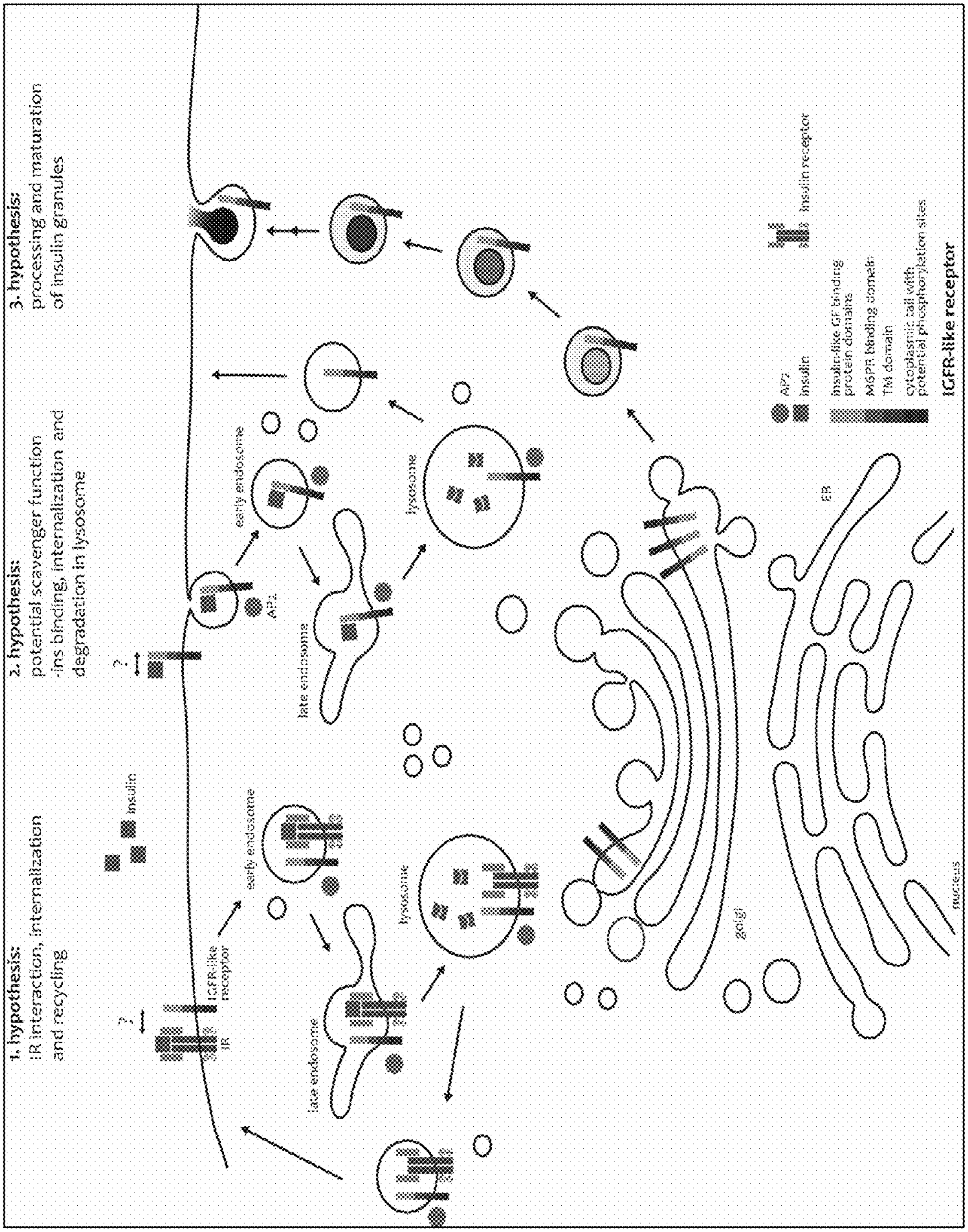
FIG. 21: Hypothetical model of IGFR-like receptor function in the insulin pathway. Schematic drawing of proposed mechanisms through which IGFR-like receptor may execute its functions. In one hypothesis IGFR-like receptor might act as a modulator of IR signaling and recycling. Upon insulin binding to the IR the association of the complex triggers recruitment of the IGFR-like receptor, in a time and dose dependent manner which, in turn, will target this complex to an early endosome/lysosome compartment were the ligand will be degraded and the IR together with the IGFR-like receptor re-routed to the plasma membrane. Another hypothesis is direct binding of the insulin ligand to the IGFR-like receptor might trigger internalization of the complex and degradation of the insulin in the lysosome thus IGFR-like receptor acting as a scavenger molecule depleting excessive pericellular amounts of insulin released under certain circumstances. Finally, IGFR-like receptor might be involved in biogenesis and maturation of insulin granules through correct guiding and trafficking of secretory vesicles.

IGFR-like receptor expression in human islets of Langerhans. Confocal images of Islets of Langerhans from human donor immunofluorescently labeled with antibodies against IGFR-like receptor (red), IGF2R (green) and Insulin (cyan)

show typical IGFR-like receptor distribution in the Golgi compartment and partial co-localization with IGF2R and insulin (FIG. 18).

Example 18: IGFR-Like Receptor is Indicative of Pancreatic β Cell Dysfunction in Human Briefly, human islets were obtained from healthy and diabetic donors and subjected to immunocytochemistry using antibodies against IGFR-like receptor, and Insulin. A detailed description of materials and methods used is provided in Example 1.

Figure 22:
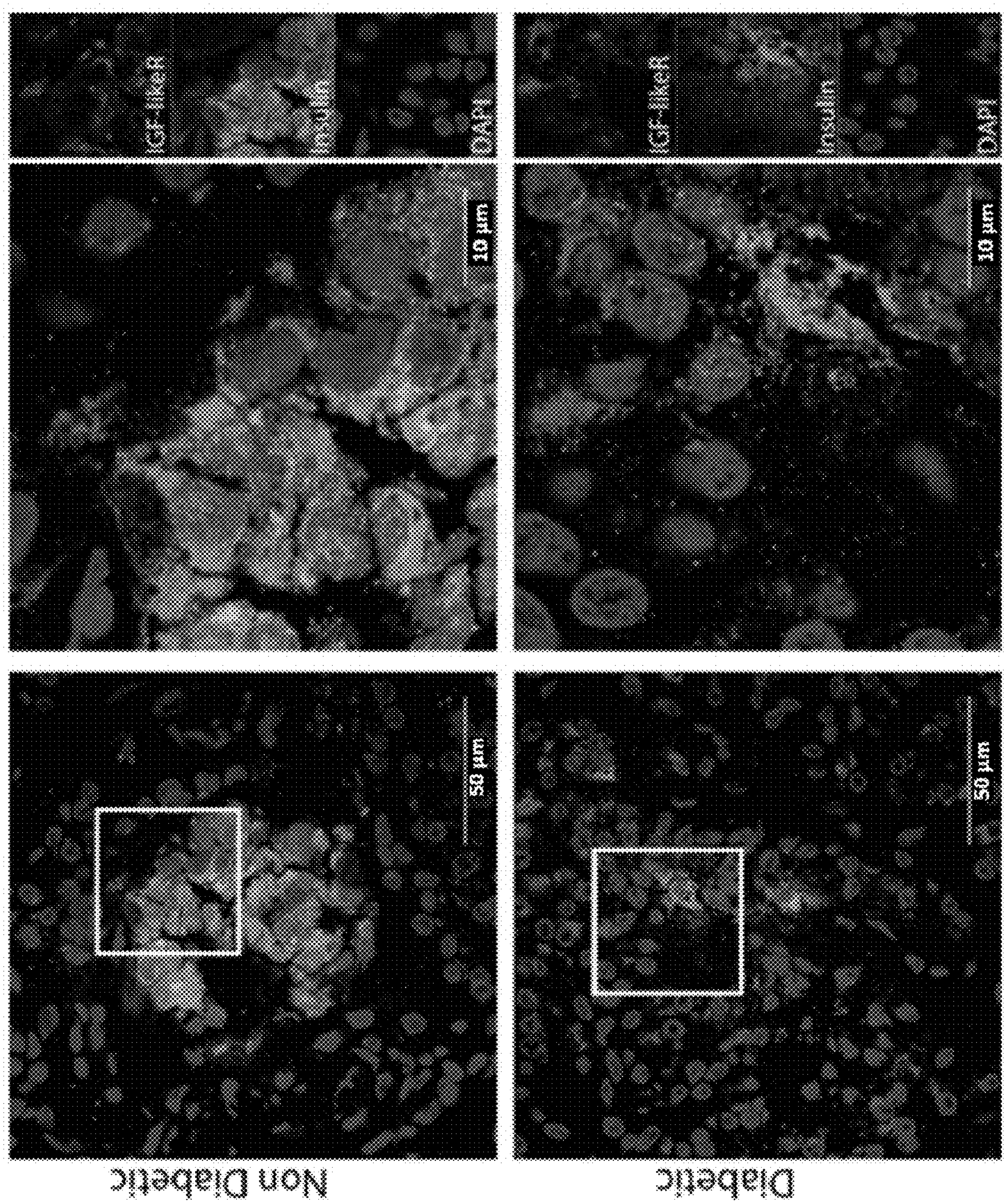
FIG. 22: IGFR-like receptor is indicative of pancreatic β cell dysfunction in human. LSM images of human pancreas sections stained with antibodies against IGFR-like receptor (red) and insulin (green). Nuclei are stained by DAPI (blue) show reduced insulin and increase IGFR-like receptor expression in a diabetic (6.9% HbA1c value) patient when compared to a non-diabetic (4.6% HbA1c value) patient. (HbA1c-used as an indication of diabetic status defined as the percentage of glycated hemoglobin HbA1c in the plasma; normal range: <5.9%).

LSM images of human pancreas sections stained with antibodies against IGFR-like receptor (red) and insulin (green). Nuclei are stained by DAPI (blue) show reduced insulin and increase IGFR-like receptor expression in a diabetic (6.9% HbA1c value) patient when compared to a non-diabetic (4.6% HbA1c value) patient. (HbA1c-used as an indicator of diabetic status defined as the percentage of glycated hemoglobin HbA1c in the plasma; normal range: <5.9%) (FIG. 22).

Figure 24:
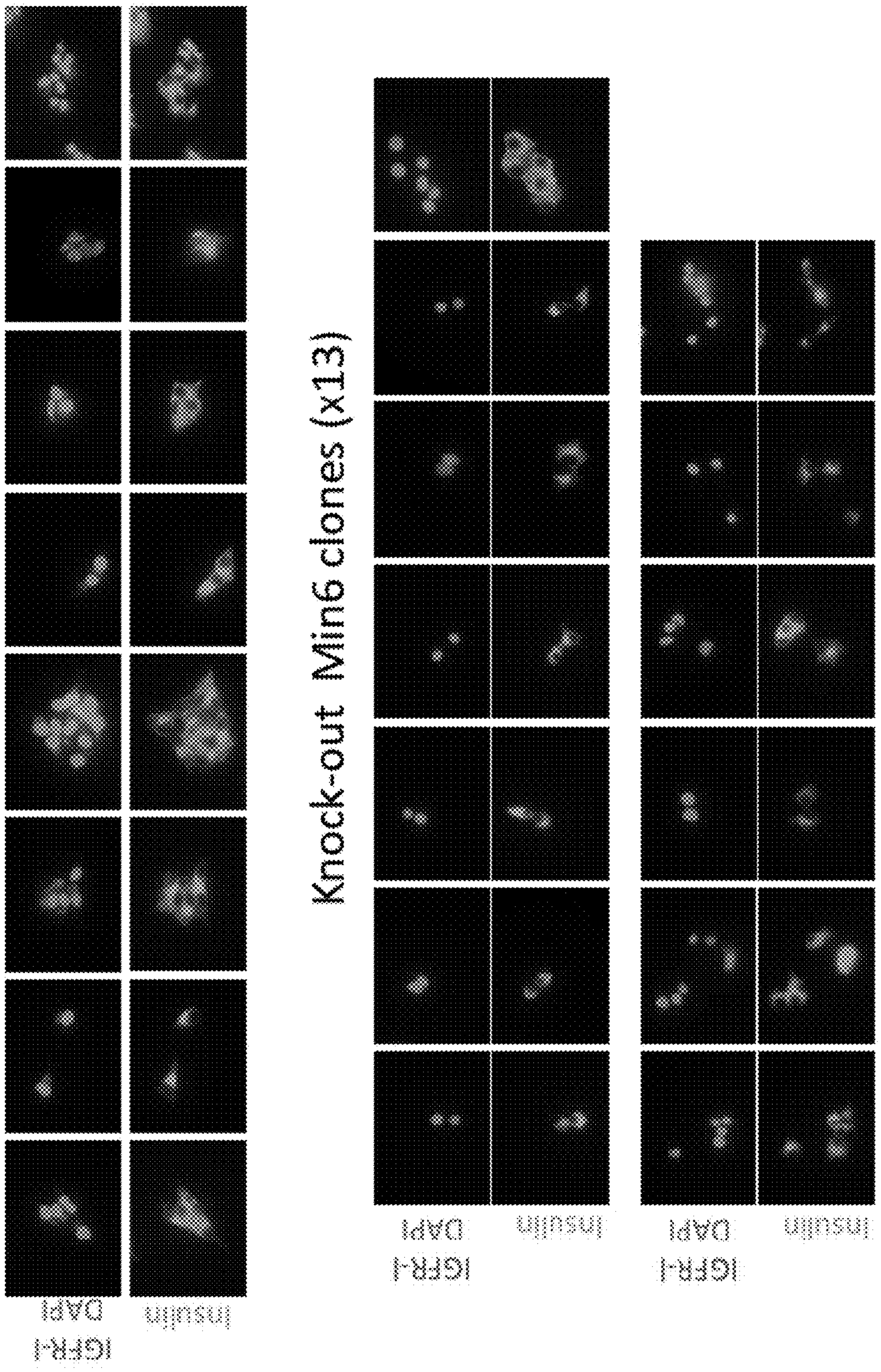
FIG. 24: IGFR-like receptor subcellular localization in wild-type and knock-out Min6 cells. Immunofluorescence images of Min6 cells stained with antibodies against IGFR-like receptor (red) and insulin (green). Nuclei were stained with DAPI (blue).
Figure 25:
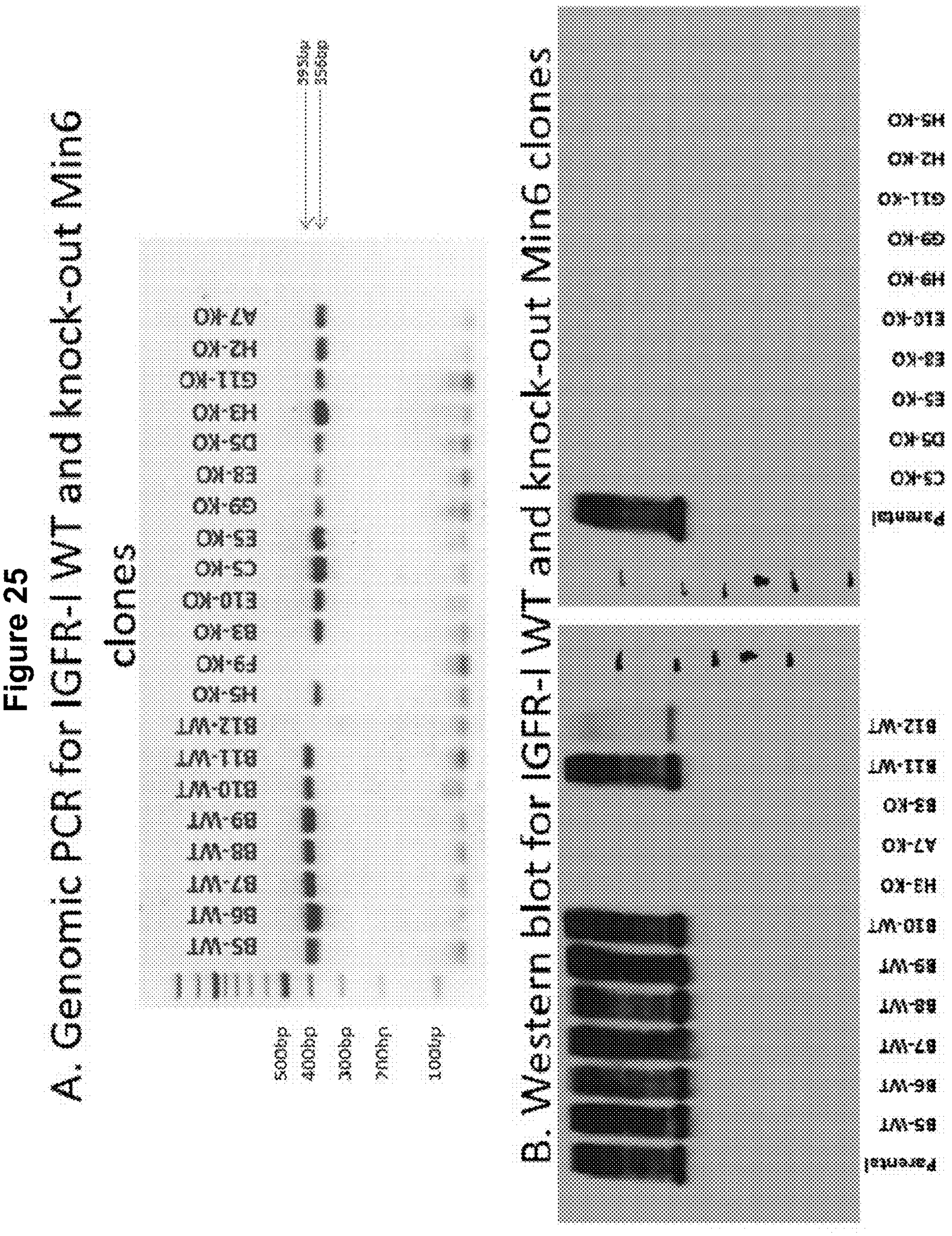
FIG. 25: IGFR-like receptor knock-out confirmation in Min6 cells. (A) Genomic PCR around the transcriptional start side of IGFR-I shows homozygous internal deletion of a large fragment. (B) Western blot confirms the IGFR-I null mutation and shows that the IGFR-I protein is completely absent in knock-out Min6 clones, confirming the immunocytochemistry results.

Example 19: IGFR-Like Receptor Subcellular Localization in Wild-Type and Knock-Out Min6 Cells. Immunofluorescence Images of Min6 Cells Stained with Antibodies Against IGFR-Like Receptor and Insulin Briefly, wild-type Min6 clones and knock-out Min6 clones were obtained and tested by genomic PCR and Western blot wherein it is shown that the IGFR-I protein is completely absent in knock-out Min6 clones (FIGS. 25A and B). Then WT and KO were subjected to immunocytochemistry using antibodies against IGFR-like receptor (red), and Insulin (green). Nuclei were stained with DAPI (blue) (FIG. 24). Immunocytochemistry confirm genomic PCR and Western blot results. A detailed description of materials and methods used is provided in Example 1.

Example 20: Influence of Knockout of IGFR-Like Receptor on Insulin/IGF Signaling in Min6 (C22RIK)

Briefly, Min6 knock-out cells were generated by CRISPR/Cas9-mediated knock-out strategy as described in Example 1 and investigated by Western blotting analysis using phosphor-specific antibodies against IR/IGF1R as well as phospho-specific antibodies against downstream signaling molecules Ampk, AKT and mTOR.

Figure 26:
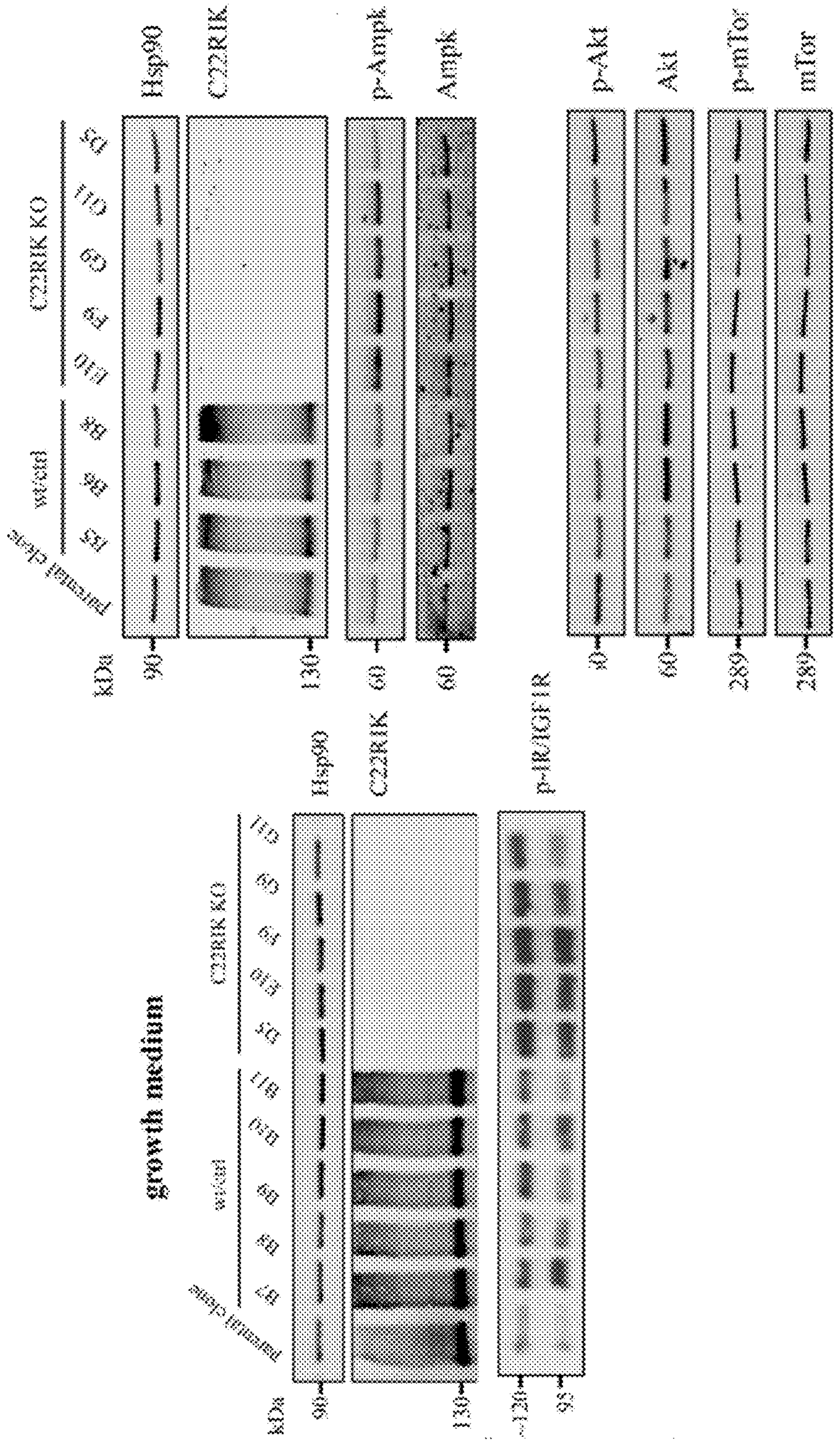
FIG. 26: IGFR-like receptor knock-out in Min6 cells. Western blotting analysis of phosphorylated Insulin receptor (IR) and downstream signaling molecules such as AMPK, AKT and mTOR, which are important molecules commonly phosphorylated as a consequence of IR activation. IGFR-like receptor knock-out in Min6 cells leads to increased phosphorylation of IR and as a consequence to increased AMPK, but not of Akt or mTor phosphorylation. Min6 control and knock-out clones were cultured under growth conditions (10% FCS and high glucose).

IGFR-like receptor knock-out in Min6 cells leads to increased phosphorylation of IR and as a consequence to increased AMPK, but not of Akt or mTor phosphorylation (FIG. 26). Min6 control and knock-out clones were cultured under growth conditions (10% FCS and high glucose).

Example 21: IGFR-Like Venus Fusion Knock-In Min6 Cell Line

Briefly, IGFR-I Venus fusion knock-in Min6 cell line was generated as described in Example 1 and subjected to immunohistochemistry using antibodies against IGFR-like receptor and Venus fluorescent reporter.

Figure 27:
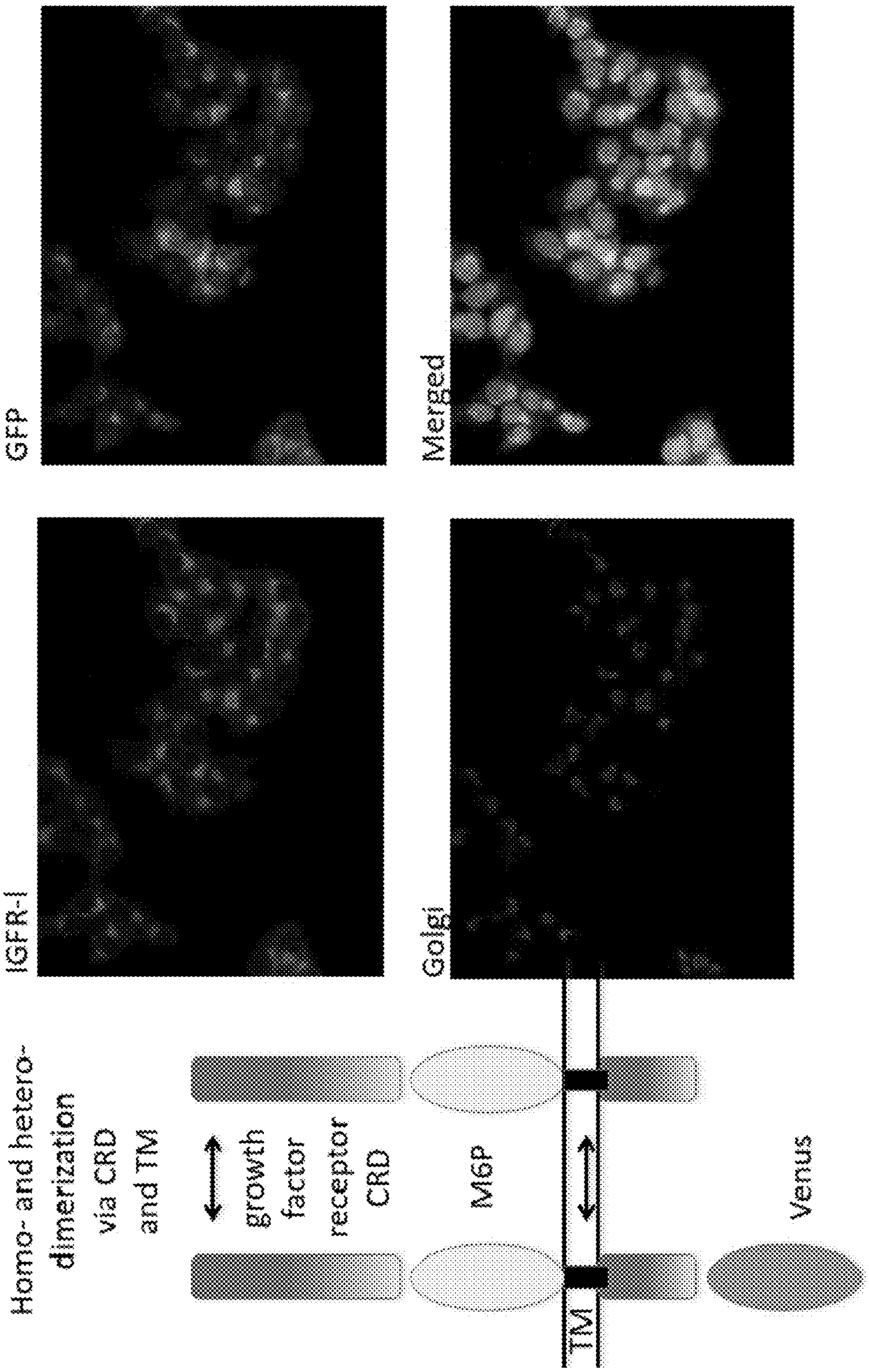
FIG. 27: IGFR-like Venus fusion knock-in Min6 cell line. IGFR-I was fused N-terminally in frame to the Venus fluorescent reporter and co-localization of the endogenous IGFR-I (anti-IGFR-I, red) and IGFR-I-Venus (anti-GFP detects Venus, green) is shown in the Golgi and trans-Golgi area. Small molecule compounds and biologics that inhibit homo- and heterodimerization via transmembrane domain (TM) or growth factor receptor cysteine-rich domain (CRD) (IPR009030) or change of intracellular localization in trans-Golgi, Golgi, lysosome and plasma membrane compartment can be identified using high-content screening approaches using this knock-in Min6 cell line.

IGFR-I Venus fusion (anti-GFP detects Venus, green) co-localizes with the endogenous IGFR-I (anti-IGFR-I, red) in the Golgi and trans-Golgi area. Small molecule compounds and biologics that inhibit homo- and heterodimerization via transmembrane domain (TM) or growth factor receptor cysteine-rich domain (CRD) (IPR009030) or change of intracellular localization in trans-Golgi, Golgi, lysosome and plasma membrane compartment can be identified using high-content screening approaches using this knock-in Min6 cell line (FIG. 27).

Example 22: IGFR-Like Receptor Localization in Endocrine Progenitors Differentiated from Induced Pluripotent Stem Cells (iPSCs)

Briefly, PDX1+/NKX6.1+ endocrine progenitors were obtained and subjected to immunohistochemistry using antibodies against PDX1, NKX6.1 and IGFR-like receptor.

Figure 28:
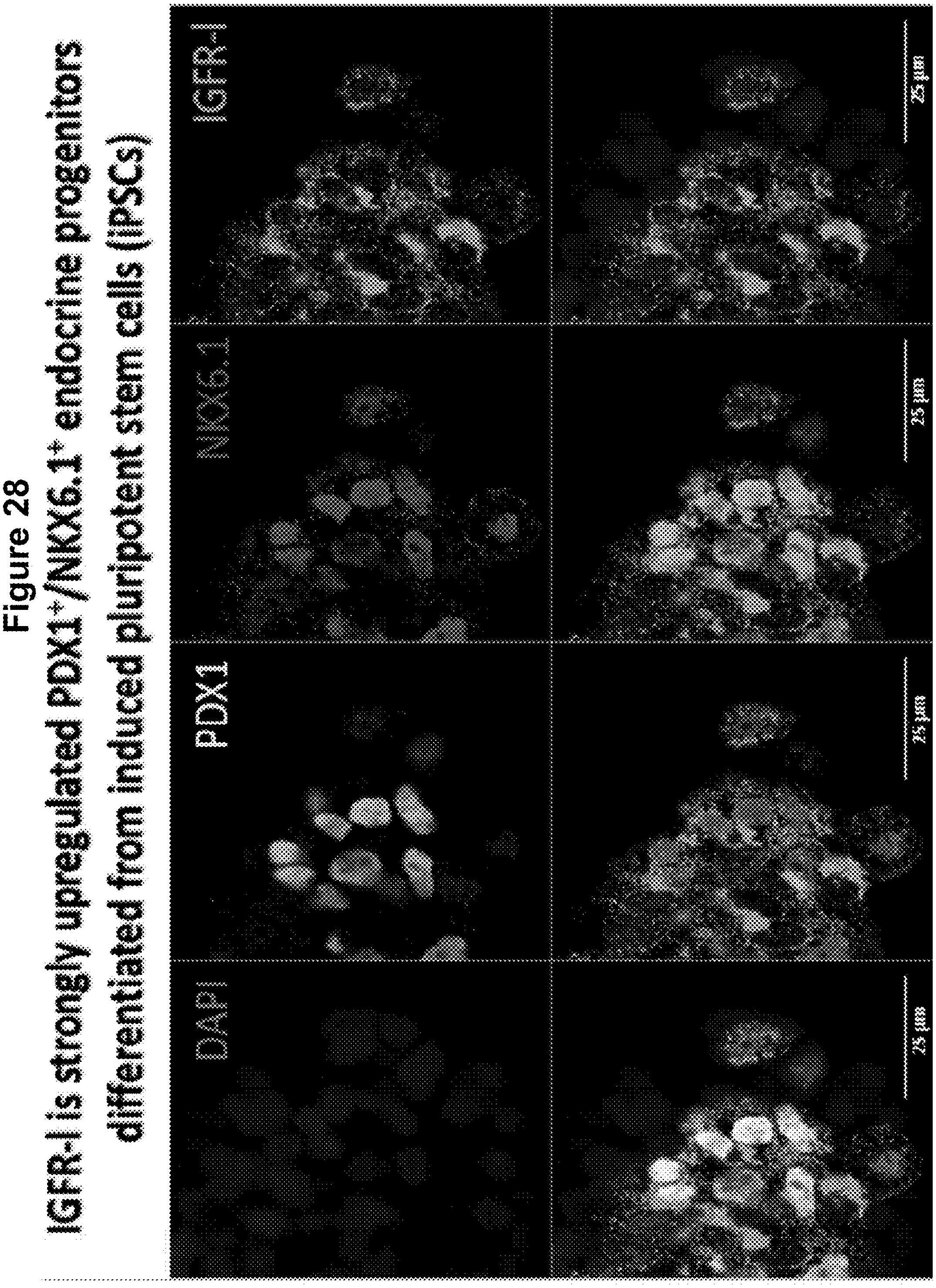
FIG. 28: IGFR-I is strongly upregulated in $PDX1^+$/$NKX6.1^+$ endocrine progenitors differentiated from human induced pluripotent stem cells (iPSCs).
Figure 29:
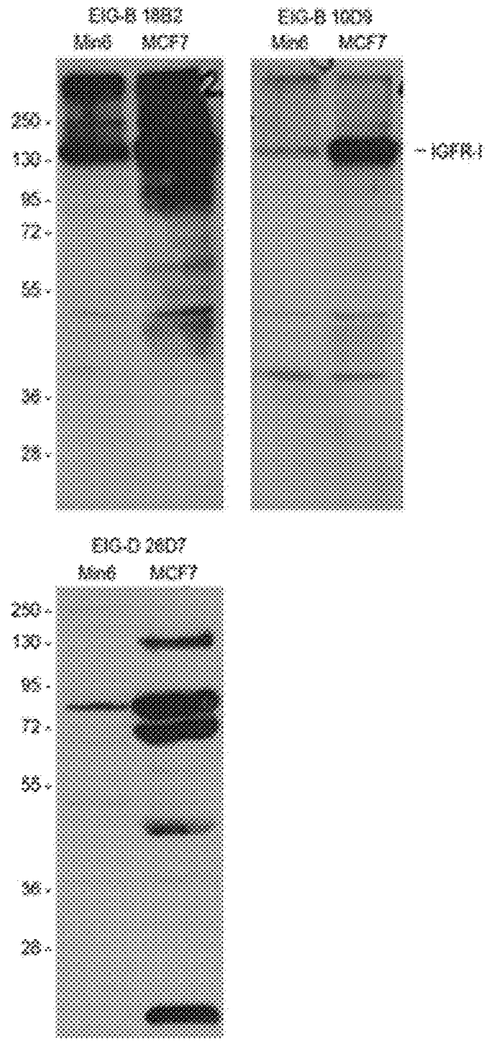
FIG. 29: Detection of IGFR-like receptor in mouse Min6 insulinoma cells and human MCF7 breast cancer cells using antibody against the extracellular domain of IGFR-like receptor. Western blotting experiments show specific recognition of a protein band of ~130 kDa in Min6 (weak) and MCF7 (strong) cell lysates by an antibody against the extracellular domain SEQ ID NO: 4 (EIG-B 1862: VHC: SEQ ID NO:31, VLC: SEQ ID NO:32; and 10D9: VHC: SEQ ID NO:33, VLC: SEQ ID NO:34) and SEQ ID NO: 6 (EIG-D 26D7: VHC: SEQ ID NO:35, VLC: SEQ ID NO:36). The EIG-B clones are monoclonal antibodies generated against the peptide SEQ ID NO: 4 in rat, whereas the EIG-D clone is a monoclonal antibody generated against the SEQ ID NO: 6 in mouse.

Confocal images of endocrine progenitors stained with antibodies against PDX1 (light blue), NKX6.1 (red) and IGFR-like receptor (green) show immunolocalization of IGFR-like receptor with PDX1 and NKX6.1 (FIG. 28). Nuclei were stained with DAPI (blue).

Example 23: Antibodies can be Generated Against Peptides B and D of IGFR-I Ectodomain in Mouse Min6 Insulinoma Cells and MCF7 Human Breast Cancer Cell Line Rat monoclonal antibodies EIG-B 18B2 (Heavy Chain Variable Region: SEQ ID NO:31, CDR-H1: SYHIS (SEQ ID NO:13), CDR-H2: AISSGGDTYYNSLLKS (SEQ ID NO:14), CDR-H3: ESY (SEQ ID NO:15), Light Chain Variable Region: SEQ ID NO:32; CDR-L1: RASENIDTYLH (SEQ ID NO:16), CDR-L2: FASQSIS (SEQ ID NO:17), and CDR-L3: QQGNILPYT (SEQ ID NO:18)), and EIG-B 10D9 (Heavy Chain Variable Region: SEQ ID NO:33, CDR-H1: SYHIS (SEQ ID NO:19), CDR-H2: AISSGGDTYYNSLLKS (SEQ ID NO:20), CDR-H3: ESY (SEQ ID NO:21), Light Chain Variable Region: SEQ ID NO:34; CDR-L1: RASENIDTYLH (SEQ ID NO:22), CDR-L2: FASQSIS (SEQ ID NO:23), and CDR-L3: QQGNILPYT (SEQ ID NO:24)), were generated and used in Western blotting against peptide B of IGFR-I ectodomain that refers to epitope SEQ ID NO. 4. Mouse monoclonal antibody EIG-D 26D7 (Heavy Chain Variable Region: SEQ ID NO:35, CDR-H1: SYWMD (SEQ ID NO:25), CDR-H2: NIYPSDGETHYNQKFK D (SEQ ID NO:26), CDR-H3: LYSEYGS (SEQ ID NO:27), Light Chain Variable Region: SEQ ID NO:36; CDR-L1: KSSQSLLNSGNQKNYLT (SEQ ID NO:28), CDR-L2: WASTRDS (SEQ ID NO:29), and CDR-L3: QNDYSYPLT (SEQ ID NO:30) was generated against peptide D of IGFR-I ectodomain that refers to epitope SEQ ID NO. 6.

Those antibodies (EIG-B and EIG-D) show specific recognition of a protein band of ~130 kDa in Min6 (weak) and MCF7 (strong) cell lysates.

Figure 30:
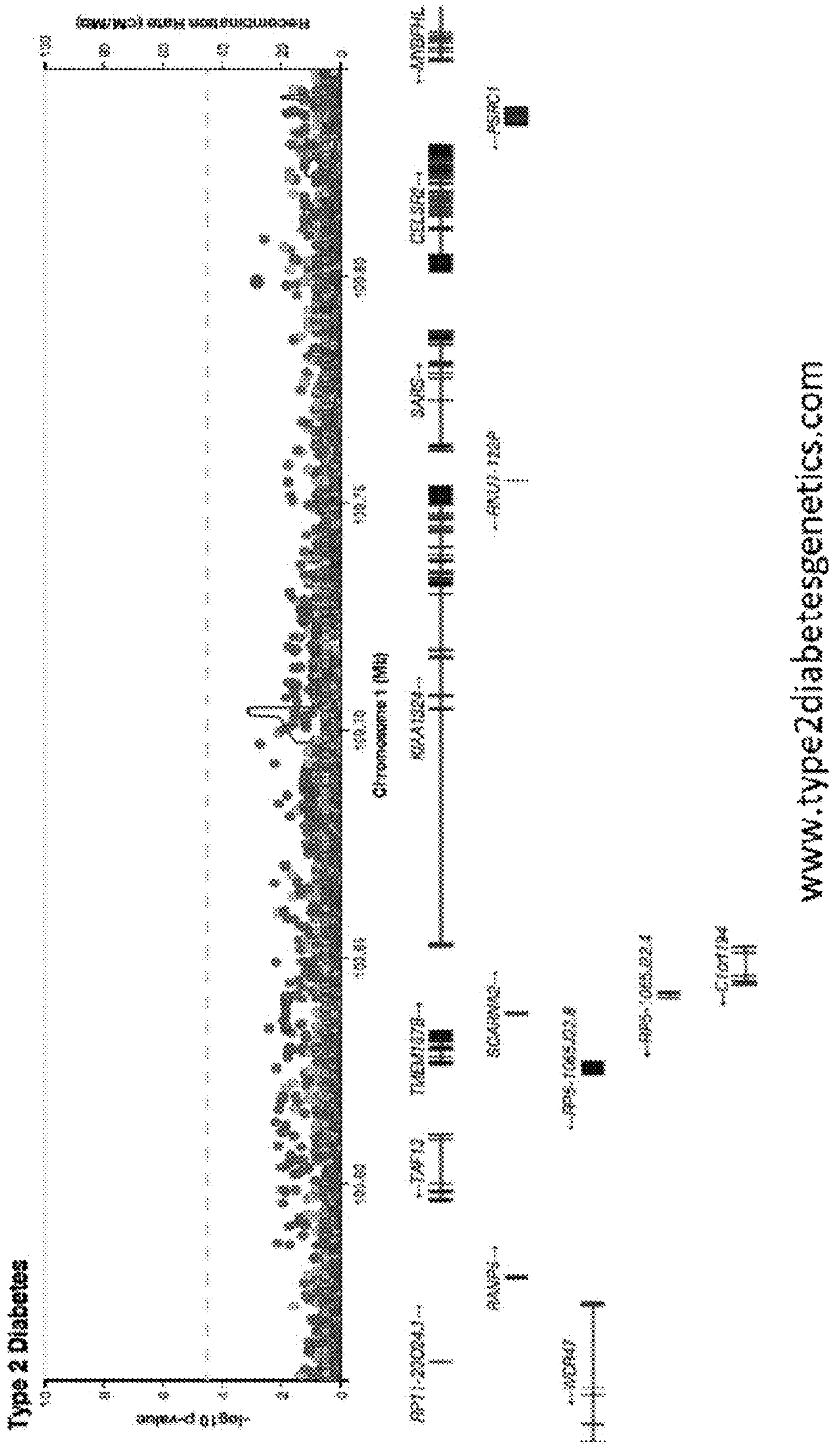
FIG. 30: IGFR-like receptor associated with type 2 diabetes in Genome-wide association metastudies. Human KIAA1324 gene encoding an IGFR-like receptor located on chromosome 1 associated with type 2 Diabetes; figure is depicted from reference www.type2diabetesgenetics.com.
Figure 31:
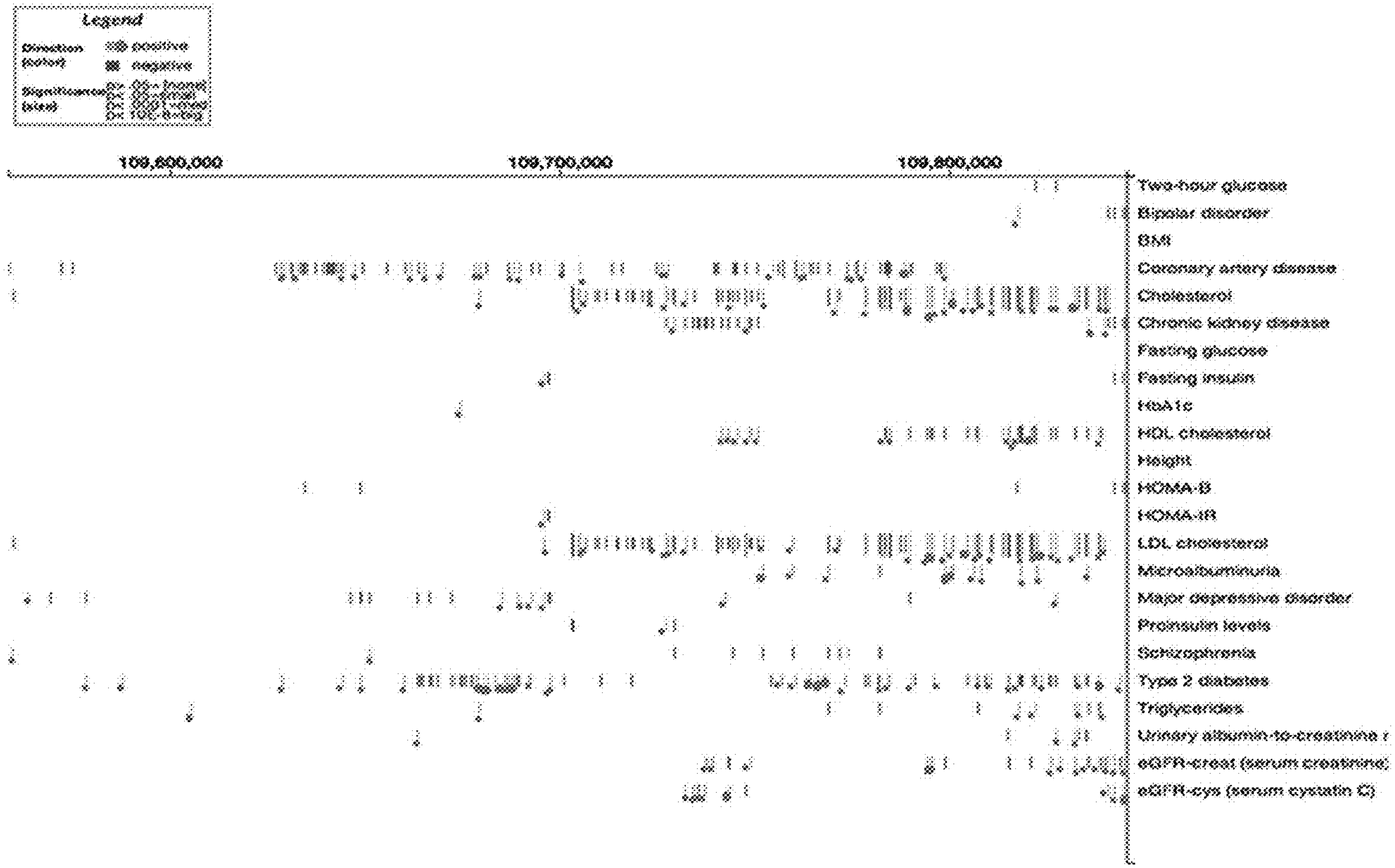
FIG. 31: SNPs in IGFR-like receptor are highly associated with coronary artery disease, LDL cholesterol and type 2 diabetes in Genome-wide association metastudies. Zoom into human chromosome 1, from 109.55-109.85 Mb. Blue bars marked with a dot refer to positive associations with disease; in return, red bars without a dot refer to negative associations. Sizes (none, small, medium and big) of bars refer to significances; figure is depicted from reference www.type2diabetesgenetics.com.

Example 24: SNPs in IGFR-Like Receptor are Highly Associated with Coronary Artery Disease, LDL Cholesterol and Type 2 Diabetes in Genome-Wide Association Metastudies Human KIAA1324 gene encoding IGFR-I on Chromosome 1 (FIG. 30) and the association of IGFR-I SNPs with specific diseases such as coronary artery disease, LDL cholesterol, and type 2 diabetes (FIG. 31). Those studies refer to Genome-wide association metastudies with half a million test persons.

What is claimed is:

1. An antibody or a fragment thereof which specifically binds to an IGFR-like receptor epitope, wherein said antibody or fragment thereof comprises complimentary determining regions (CDRs):

CDR-H1:
(SEQ ID NO: 13 or 19)
SYHIS,

-continued

CDR-H2:
(SEQ ID NO: 14 or 20)
AISSGGDTYYNSLLKS,

CDR-H3:
(SEQ ID NO: 15 or 21)
ESY,

-continued

CDR-L1: (SEQ ID NO:16 or 22)
RASENIDTYLH,

CDR-L2: (SEQ ID NO: 17 or 23)
FASQSIS, and

CDR-L3: (SEQ ID NO: 18 or 24)
QQGNILPYT; or

CDR-H1: (SEQ ID NO: 25)
SYWMD,

CDR-H2: (SEQ ID NO: 26)
NIYPSDGETHYNQKFKD,

CDR-H3: (SEQ ID NO: 27)
LYSEYGS,

CDR-L1: (SEQ ID NO: 28)
KSSQSLLNSGNQKNYLT,

CDR-L2: (SEQ ID NO: 29)
WASTRDS, and

CDR-L3: (SEQ ID NO: 30)
QNDYSYPLT.

2. The antibody or a fragment thereof of claim 1, wherein the antibody is a monoclonal antibody.

3. The antibody or a fragment thereof of claim 1, wherein the antibody fragment is any one of a dAb, an affibody, a Fab, a Fab', a F(ab')2, a Fv, a single chain Fv (scFv), a diabody, or a minibody comprising a scFv joined to a CH3 domain.

4. The antibody or a fragment thereof of claim 1, wherein the antibody specifically binds with an affinity of at least about $10^7$ $M^{-1}$ to an epitope of said IGFR-like receptor, the epitope comprising sequence:

(i) (SEQ ID NO.: 4)
MYKWAKPKICSEDLEG;

(ii) (SEQ ID NO.: 6)
CTFSRNTPTRTFNY, or (iii) both (i) and (ii).

5. The antibody or a fragment thereof of claim 1, wherein the antibody is a humanized antibody.

6. The antibody or a fragment thereof of claim 1, wherein the antibody comprises:

(i) a variable heavy chain amino acid sequence SEQ ID NO:31, and a variable light chain amino acid sequence SEQ ID NO:32, (ii) a variable heavy chain amino acid sequence SEQ ID NO:33, and a variable light chain amino acid sequence SEQ ID NO:34, or (iii) a variable heavy chain amino acid sequence SEQ ID NO:35, and a variable light chain amino acid sequence SEQ ID NO:36.

7. The antibody or a fragment thereof of claim 1, wherein the antibody comprises:

(i) a heavy chain amino acid sequence SEQ ID NO: 37, and a light chain amino acid sequence SEQ ID NO: 38, (ii) a heavy chain amino acid sequence SEQ ID NO: 39, and a light chain amino acid sequence SEQ ID NO: 40, or (iii) a heavy chain amino acid sequence SEQ ID NO: 41, and a light chain amino acid sequence SEQ ID NO: 42.

8. The antibody or a fragment thereof of claim 1, wherein the antibody specifically binds to an epitope of said IGFR-like receptor that is SEQ ID NO:1.

9. The antibody or a fragment thereof of claim 1, wherein the antibody specifically binds to an epitope of said IGFR-like receptor, the epitope comprising sequence:

(i) (SEQ ID NO.: 4)
MYKWAKPKICSEDLEG;
and/or (ii) (SEQ ID NO.: 6)
CTFSRNTPTRTFNY.

10. The antibody or a fragment thereof of claim 1, wherein the antibody is identified as an antagonist by using an in vitro screening method comprising the following steps:

(a) providing a stable cell line expressing said IGFR-like receptor;

(b) contacting said cell line of (a) with the antibody or a fragment thereof; and (c) measuring or detecting an IGFR-like receptor downstream signaling event, wherein the antibody or a fragment thereof of step (b) is identified as an antagonist by increasing said IGFR-like receptor downstream signaling event;

wherein said IGFR-like receptor comprises a sequence corresponding to sequence SEQ ID NO: 1, and wherein said downstream signaling event is InsR phosphorylation, AMPK phosphorylation, mTOR phosphorylation, and/or AKT phosphorylation.

11. A pharmaceutical composition comprising the antibody or a fragment thereof of claim 1, optionally with one or more pharmaceutical excipients.

12. The pharmaceutical composition of claim 11, wherein the antibody or a fragment thereof increases InsR-mediated signaling.

13. The pharmaceutical composition of claim 11, wherein the antibody or a fragment thereof increases phosphorylation of InsR, IGF1R, Akt, mTOR and/or AMPK.

14. A diagnostic composition comprising the antibody or a fragment thereof of claim 1.

15. A method of diagnosing diabetes or the risk of developing diabetes, the method comprising administering the diagnostic composition of claim 14 to a subject in need thereof.

* * * * *

SEQUENCE LISTING

<160> NUMBER OF SEQ ID NOS: 42

<210> SEQ ID NO 1
<211> LENGTH: 1013
<212> TYPE: PRT
<213> ORGANISM: Human

<400> SEQUENCE: 1

Met Ala Glu Pro Gly His Ser His His Leu Ser Ala Arg Val Arg Gly
1               5                   10                  15

Arg Thr Glu Arg Arg Ile Pro Arg Leu Trp Arg Leu Leu Leu Trp Ala
            20                  25                  30

Gly Thr Ala Phe Gln Val Thr Gln Gly Thr Gly Pro Glu Leu His Ala
        35                  40                  45

Cys Lys Glu Ser Glu Tyr His Tyr Glu Tyr Thr Ala Cys Asp Ser Thr
    50                  55                  60

Gly Ser Arg Trp Arg Val Ala Val Pro His Thr Pro Gly Leu Cys Thr
65                  70                  75                  80

Ser Leu Pro Asp Pro Ile Lys Gly Thr Glu Cys Ser Phe Ser Cys Asn
                85                  90                  95

Ala Gly Glu Phe Leu Asp Met Lys Asp Gln Ser Cys Lys Pro Cys Ala
            100                 105                 110

Glu Gly Arg Tyr Ser Leu Gly Thr Gly Ile Arg Phe Asp Glu Trp Asp
        115                 120                 125

Glu Leu Pro His Gly Phe Ala Ser Leu Ser Ala Asn Met Glu Leu Asp
    130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
                165                 170                 175

Leu Met Tyr Ala Val Asn Leu Lys Gln Ser Gly Thr Val Asn Phe Glu
            180                 185                 190

Tyr Tyr Tyr Pro Asp Ser Ser Ile Ile Phe Glu Phe Phe Val Gln Asn
        195                 200                 205

Asp Gln Cys Gln Pro Asn Ala Asp Asp Ser Arg Trp Met Lys Thr Thr
    210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
            260                 265                 270

Ser Glu Cys Phe Pro Cys Lys Pro Gly Thr Tyr Ala Asp Lys Gln Gly
        275                 280                 285

Ser Ser Phe Cys Lys Leu Cys Pro Ala Asn Ser Tyr Ser Asn Lys Gly
    290                 295                 300

Glu Thr Ser Cys His Gln Cys Asp Pro Asp Lys Tyr Ser Glu Lys Gly
305                 310                 315                 320

Ser Ser Ser Cys Asn Val Arg Pro Ala Cys Thr Asp Lys Asp Tyr Phe
                325                 330                 335

Tyr Thr His Thr Ala Cys Asp Ala Asn Gly Glu Thr Gln Leu Met Tyr
            340                 345                 350

Lys Trp Ala Lys Pro Lys Ile Cys Ser Glu Asp Leu Glu Gly Ala Val
        355                 360                 365

-continued

```
Lys Leu Pro Ala Ser Gly Val Lys Thr His Cys Pro Pro Cys Asn Pro
    370                 375                 380

Gly Phe Phe Lys Thr Asn Asn Ser Thr Cys Gln Pro Cys Pro Tyr Gly
385                 390                 395                 400

Ser Tyr Ser Asn Gly Ser Asp Cys Thr Arg Cys Pro Ala Gly Thr Glu
                405                 410                 415

Pro Ala Val Gly Phe Glu Tyr Lys Trp Trp Asn Thr Leu Pro Thr Asn
            420                 425                 430

Met Glu Thr Thr Val Leu Ser Gly Ile Asn Phe Glu Tyr Lys Gly Met
        435                 440                 445

Thr Gly Trp Glu Val Ala Gly Asp His Ile Tyr Thr Ala Ala Gly Ala
    450                 455                 460

Ser Asp Asn Asp Phe Met Ile Leu Thr Leu Val Val Pro Gly Phe Arg
465                 470                 475                 480

Pro Pro Gln Ser Val Met Ala Asp Thr Glu Asn Lys Glu Val Ala Arg
                485                 490                 495

Ile Thr Phe Val Phe Glu Thr Leu Cys Ser Val Asn Cys Glu Leu Tyr
            500                 505                 510

Phe Met Val Gly Val Asn Ser Arg Thr Asn Thr Pro Val Glu Thr Trp
        515                 520                 525

Lys Gly Ser Lys Gly Lys Gln Ser Tyr Thr Tyr Ile Ile Glu Glu Asn
    530                 535                 540

Thr Thr Thr Ser Phe Thr Trp Ala Phe Gln Arg Thr Thr Phe His Glu
545                 550                 555                 560

Ala Ser Arg Lys Tyr Thr Asn Asp Val Ala Lys Ile Tyr Ser Ile Asn
                565                 570                 575

Val Thr Asn Val Met Asn Gly Val Ala Ser Tyr Cys Arg Pro Cys Ala
            580                 585                 590

Leu Glu Ala Ser Asp Val Gly Ser Ser Cys Thr Ser Cys Pro Ala Gly
        595                 600                 605

Tyr Tyr Ile Asp Arg Asp Ser Gly Thr Cys His Ser Cys Pro Thr Asn
    610                 615                 620

Thr Ile Leu Lys Ala His Gln Pro Tyr Gly Val Gln Ala Cys Val Pro
625                 630                 635                 640

Cys Gly Pro Gly Thr Lys Asn Asn Lys Ile His Ser Leu Cys Tyr Asn
                645                 650                 655

Asp Cys Thr Phe Ser Arg Asn Thr Pro Thr Arg Thr Phe Asn Tyr Asn
            660                 665                 670

Phe Ser Ala Leu Ala Asn Thr Val Thr Leu Ala Gly Gly Pro Ser Phe
        675                 680                 685

Thr Ser Lys Gly Leu Lys Tyr Phe His His Phe Thr Leu Ser Leu Cys
    690                 695                 700

Gly Asn Gln Gly Arg Lys Met Ser Val Cys Thr Asp Asn Val Thr Asp
705                 710                 715                 720

Leu Arg Ile Pro Glu Gly Glu Ser Gly Phe Ser Lys Ser Ile Thr Ala
                725                 730                 735

Tyr Val Cys Gln Ala Val Ile Ile Pro Pro Glu Val Thr Gly Tyr Lys
            740                 745                 750

Ala Gly Val Ser Ser Gln Pro Val Ser Leu Ala Asp Arg Leu Ile Gly
        755                 760                 765

Val Thr Thr Asp Met Thr Leu Asp Gly Ile Thr Ser Pro Ala Glu Leu
    770                 775                 780

Phe His Leu Glu Ser Leu Gly Ile Pro Asp Val Ile Phe Phe Tyr Arg
```

-continued

```
785                 790                 795                 800

Ser Asn Asp Val Thr Gln Ser Cys Ser Ser Gly Arg Ser Thr Thr Ile
                805                 810                 815

Arg Val Arg Cys Ser Pro Gln Lys Thr Val Pro Gly Ser Leu Leu Leu
            820                 825                 830

Pro Gly Thr Cys Ser Asp Gly Thr Cys Asp Gly Cys Asn Phe His Phe
        835                 840                 845

Leu Trp Glu Ser Ala Ala Ala Cys Pro Leu Cys Ser Val Ala Asp Tyr
    850                 855                 860

His Ala Ile Val Ser Ser Cys Val Ala Gly Ile Gln Lys Thr Thr Tyr
865                 870                 875                 880

Val Trp Arg Glu Pro Lys Leu Cys Ser Gly Gly Ile Ser Leu Pro Glu
                885                 890                 895

Gln Arg Val Thr Ile Cys Lys Thr Ile Asp Phe Trp Leu Lys Val Gly
            900                 905                 910

Ile Ser Ala Gly Thr Cys Thr Ala Ile Leu Leu Thr Val Leu Thr Cys
        915                 920                 925

Tyr Phe Trp Lys Lys Asn Gln Lys Leu Glu Tyr Lys Tyr Ser Lys Leu
    930                 935                 940

Val Met Asn Ala Thr Leu Lys Asp Cys Asp Leu Pro Ala Ala Asp Ser
945                 950                 955                 960

Cys Ala Ile Met Glu Gly Glu Asp Val Glu Asp Asp Leu Ile Phe Thr
                965                 970                 975

Ser Lys Lys Ser Leu Phe Gly Lys Ile Lys Ser Phe Thr Ser Lys Arg
            980                 985                 990

Thr Pro Asp Gly Phe Asp Ser Val  Pro Leu Lys Thr Ser  Ser Gly Gly
        995                 1000                 1005

Leu Asp  Met Asp Leu
    1010


<210> SEQ ID NO 2
<211> LENGTH: 16
<212> TYPE: PRT
<213> ORGANISM: Human

<400> SEQUENCE: 2

Thr Ser Lys Arg Thr Pro Asp Gly Phe Asp Ser Val Pro Leu Lys Thr
1               5                   10                  15


<210> SEQ ID NO 3
<211> LENGTH: 11
<212> TYPE: PRT
<213> ORGANISM: Human

<400> SEQUENCE: 3

Cys His Gln Cys Asp Pro Asp Lys Tyr Ser Glu
1               5                   10


<210> SEQ ID NO 4
<211> LENGTH: 16
<212> TYPE: PRT
<213> ORGANISM: Human

<400> SEQUENCE: 4

Met Tyr Lys Trp Ala Lys Pro Lys Ile Cys Ser Glu Asp Leu Glu Gly
1               5                   10                  15


<210> SEQ ID NO 5
```

<211> LENGTH: 15
<212> TYPE: PRT
<213> ORGANISM: Human

<400> SEQUENCE: 5

Phe Gln Arg Thr Thr Phe His Glu Ala Ser Arg Lys Tyr Thr Asn
1               5                   10                  15

<210> SEQ ID NO 6
<211> LENGTH: 14
<212> TYPE: PRT
<213> ORGANISM: Human

<400> SEQUENCE: 6

Cys Thr Phe Ser Arg Asn Thr Pro Thr Arg Thr Phe Asn Tyr
1               5                   10

<210> SEQ ID NO 7
<211> LENGTH: 3042
<212> TYPE: DNA
<213> ORGANISM: Human

<400> SEQUENCE: 7
atggctgagc ctgggcacag ccaccatctc tccgccagag tcaggggaag aactgagagg 60
cgcatacccc ggctgtggcg gctgctgctc tgggctggga ccgccttcca ggtgacccag 120
ggaacgggac cggagcttca tgcctgcaaa gagtctgagt accactatga gtacacggcg 180
tgtgacagca cgggttccag gtggagggtc gccgtgccgc ataccccggg cctgtgcacc 240
agcctgcctg accccgtcaa gggcaccgag tgctccttct cctgcaacgc cggggagttt 300
ctggatatga aggaccagtc atgtaagcca tgcgctgagg gccgctactc cctcggcaca 360
ggcattcggt ttgatgagtg ggatgagctg ccccatggct ttgccagcct ctcagccaac 420
atggagctgg atgacagtgc tgctgagtcc accgggaact gtacttcgtc caagtgggtt 480
ccccggggcg actacatcgc ctccaacacg gacgaatgca cagccacact gatgtacgcc 540
gtcaacctga agcaatctgg caccgttaac ttcgaatact actatccaga ctccagcatc 600
atctttgagt tttcgttcca gaatgaccag tgccagccca atgcagatga ctccaggtgg 660
atgaagacca cagagaaagg atgggaattc cacagtgtgg agctaaatcg aggcaataat 720
gtcctctatt ggagaaccac agccttctca gtatggacca aagtacccaa gcctgtgctg 780
gtgagaaaca ttgccataac aggggtggcc tacacttcag aatgcttccc ctgcaaacct 840
ggcacgtatg cagacaagca gggctcctct ttctgcaaac tttgcccagc caactcttat 900
tcaaataaag gagaaacttc ttgccaccag tgtgaccctg acaaatactc agagaaagga 960
tcttcttcct gtaacgtgcg cccagcttgc acagacaaag attatttcta cacacacacg 1020
gcctgcgatg ccaacggaga gacacaactc atgtacaaat gggccaagcc gaaaatctgt 1080
agcgaggacc ttgagggggc agtgaagctg cctgcctctg gtgtgaagac ccactgccca 1140
ccctgcaacc caggcttctt caaaaccaac aacagcacct gccagccctg cccatatggt 1200
tcctactcca atggctcaga ctgtacccgc tgccctgcag ggactgaacc tgctgtggga 1260
tttgaataca aatggtggaa cacgctgccc acaaacatgg aaacgaccgt tctcagtggg 1320
atcaacttcg agtacaaggg catgacaggc tgggaggtgg ctggtgatca catttacaca 1380
gctgctggag cctcagacaa tgacttcatg attctcactc tggttgtgcc aggatttaga 1440
cctccgcagt cggtgatggc agacacagag aataaagagg tggccagaat cacatttgtc 1500
tttgagaccc tctgttctgt gaactgtgag ctctacttca tggtgggtgt gaattctagg 1560
accaacactc ctgtggagac gtggaaaggt tccaaaggca aacagtccta tacctacatc 1620
attgaggaga acactaccac gagcttcacc tgggccttcc agaggaccac ttttcatgag 1680
gcaagcagga agtacaccaa tgacgttgcc aagatctact ccatcaatgt caccaatgtt 1740
atgaatggtg tggcctccta ctgccgtccc tgtgccctag aagcctctga tgtgggctcc 1800
tcctgcacct cttgtcctgc tggttactat attgaccgag attcaggaac ctgccactcc 1860
tgccccacta acacaattct gaaagcccac cagccttatg gtgtccaggc ctgtgtgccc 1920
tgtggtccag ggaccaagaa caacaagatc cactctctgt gctacaacga ttgcaccttc 1980
tcacgcaaca ctccgaccag gactttcaac tacaacttct ccgctttggc aaacactgtc 2040
actcttgctg gagggccaag cttcacttcc aaagggctga aatacttcca tcactttacc 2100
ctcagtctct gtggaaacca gggtaggaaa atgtctgtgt gcaccgacaa tgtcactgac 2160
ctccggattc ctgagggtga gtcagggttc tccaaatcta tcacagccta cgtctgccag 2220
gcagtcatca tcccccccaga ggtgacaggc tacaaggccg gggtttcctc acagcctgtc 2280
agccttgctg atcgacttat tggggtgaca acagatatga ctctggatgg aatcacctcc 2340
ccagctgaac ttttccacct ggagtccttg ggaataccgg acgtgatctt cttttatagg 2400
tccaatgatg tgacccagtc ctgcagttct gggagatcaa ccaccatccg cgtcaggtgc 2460
agtccacaga aaactgtccc tggaagtttg ctgctgccag gaacgtgctc ggatgggacc 2520
tgtgatggct gcaacttcca cttcctgtgg gagagcgcgg ctgcttgccc gctctgctca 2580
gtggctgact accatgctat cgtcagcagc tgtgtggctg ggatccagaa gactacttac 2640
gtgtggcgag aacccaagct atgctctggt ggcatttctc tgcctgagca gagagtcacc 2700
atctgcaaaa ccatagattt ctggctgaaa gtgggcatct ctgcaggcac ctgtactgcc 2760
atcctgctca ccgtcttgac ctgctacttt tggaaaaaga atcaaaaact agagtacaag 2820
tactccaagc tggtgatgaa tgctactctc aaggactgtg acctgccagc agctgacagc 2880
tgcgccatca tggaaggcga ggatgtagag gacgacctca tctttaccag caagaagtca 2940
ctctttggga agatcaaatc atttacctcc aagaggactc ctgatggatt tgactcagtg 3000
ccgctgaaga catcctcagg aggcctagac atggacctgt ga 3042

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tgggtagcct ttctgtatgg 20

<210> SEQ ID NO 9
<211> LENGTH: 20
<212> TYPE: DNA
<213> ORGANISM: Artificial
<220> FEATURE:
<223> OTHER INFORMATION: Reverse Primer

<400> SEQUENCE: 9
gacatagggc agatttgtgg 20

<210> SEQ ID NO 10
<211> LENGTH: 85
<212> TYPE: PRT

<213> ORGANISM: Human

<400> SEQUENCE: 10

```
Thr Met Asp Lys Lys Asn Gln Lys Leu Glu Tyr Lys Tyr Ser Lys Leu
1               5                   10                  15

Val Met Asn Ala Thr Leu Lys Asp Cys Asp Leu Pro Ala Ala Asp Ser
            20                  25                  30

Cys Ala Ile Met Glu Gly Glu Asp Val Glu Asp Asp Leu Ile Phe Thr
        35                  40                  45

Ser Lys Lys Ser Leu Phe Gly Lys Ile Lys Ser Phe Thr Ser Lys Arg
    50                  55                  60

Thr Pro Asp Gly Phe Asp Ser Val Pro Leu Lys Thr Ser Ser Gly Gly
65                  70                  75                  80

Leu Asp Met Asp Leu
                85
```

<210> SEQ ID NO 11
<211> LENGTH: 4
<212> TYPE: PRT
<213> ORGANISM: Artificial
<220> FEATURE:
<223> OTHER INFORMATION: Motif
<220> FEATURE:
<221> NAME/KEY: X
<222> LOCATION: (2)..(3)
<223> OTHER INFORMATION: X can be selected from any amino acid
<220> FEATURE:
<221> NAME/KEY: X
<222> LOCATION: (4)..(4)
<223> OTHER INFORMATION: X can be selected from F, I, L, M or V

<400> SEQUENCE: 11

```
Tyr Xaa Xaa Xaa
1
```

<210> SEQ ID NO 12
<211> LENGTH: 74
<212> TYPE: PRT
<213> ORGANISM: Artificial
<220> FEATURE:
<223> OTHER INFORMATION: Motif

<400> SEQUENCE: 12

```
Lys Lys Asn Gln Lys Leu Glu Tyr Lys Tyr Ser Lys Leu Val Met Thr
1               5                   10                  15

Thr Asn Ser Lys Glu Cys Glu Leu Pro Ala Ala Asp Ser Cys Ala Ile
            20                  25                  30

Met Glu Gly Glu Asp Asn Glu Glu Glu Val Val Tyr Ser Asn Lys Gln
        35                  40                  45

Ser Leu Leu Gly Lys Leu Lys Ser Leu Ala Thr Lys Glu Lys Glu Asp
    50                  55                  60

His Phe Glu Ser Val Gln Leu Lys Thr Ser
65                  70
```

<210> SEQ ID NO 13
<211> LENGTH: 5
<212> TYPE: PRT
<213> ORGANISM: Artificial
<220> FEATURE:
<223> OTHER INFORMATION: EIG B 18B2 CDR-H1

<400> SEQUENCE: 13

```
Ser Tyr His Ile Ser
```

-continued 1 5

<210> SEQ ID NO 14
<211> LENGTH: 16
<212> TYPE: PRT
<213> ORGANISM: Artificial
<220> FEATURE:
<223> OTHER INFORMATION: EIG B 18B2 CDR-H2

<400> SEQUENCE: 14

Ala Ile Ser Ser Gly Gly Asp Thr Tyr Tyr Asn Ser Leu Leu Lys Ser
1 5 10 15

<210> SEQ ID NO 15
<211> LENGTH: 3
<212> TYPE: PRT
<213> ORGANISM: Artificial
<220> FEATURE:
<223> OTHER INFORMATION: EIG B 18B2 CDR-H3

<400> SEQUENCE: 15

Glu Ser Tyr
1

<210> SEQ ID NO 16
<211> LENGTH: 11
<212> TYPE: PRT
<213> ORGANISM: Artificial
<220> FEATURE:
<223> OTHER INFORMATION: EIG B 18B2 CDR-L1

<400> SEQUENCE: 16

Arg Ala Ser Glu Asn Ile Asp Thr Tyr Leu His
1 5 10

<210> SEQ ID NO 17
<211> LENGTH: 7
<212> TYPE: PRT
<213> ORGANISM: Artificial
<220> FEATURE:
<223> OTHER INFORMATION: EIG B 18B2 CDR-L2

<400> SEQUENCE: 17

Phe Ala Ser Gln Ser Ile Ser
1 5

<210> SEQ ID NO 18
<211> LENGTH: 9
<212> TYPE: PRT
<213> ORGANISM: Artificial
<220> FEATURE:
<223> OTHER INFORMATION: EIG B 18B2 CDR-L3

<400> SEQUENCE: 18

Gln Gln Gly Asn Ile Leu Pro Tyr Thr
1 5

<210> SEQ ID NO 19
<211> LENGTH: 5
<212> TYPE: PRT
<213> ORGANISM: Artificial
<220> FEATURE:
<223> OTHER INFORMATION: EIG B 10D9 CDR-H1

<400> SEQUENCE: 19

Ser Tyr His Ile Ser
1 5

<210> SEQ ID NO 20
<211> LENGTH: 16
<212> TYPE: PRT
<213> ORGANISM: Artificial
<220> FEATURE:
<223> OTHER INFORMATION: EIG B 10D9 CDR-H2

<400> SEQUENCE: 20

Ala Ile Ser Ser Gly Gly Asp Thr Tyr Tyr Asn Ser Leu Leu Lys Ser
1 5 10 15

<210> SEQ ID NO 21
<211> LENGTH: 3
<212> TYPE: PRT
<213> ORGANISM: Artificial
<220> FEATURE:
<223> OTHER INFORMATION: EIG B 10D9 CDR-H3

<400> SEQUENCE: 21

Glu Ser Tyr
1

<210> SEQ ID NO 22
<211> LENGTH: 11
<212> TYPE: PRT
<213> ORGANISM: Artificial
<220> FEATURE:
<223> OTHER INFORMATION: EIG B 10D9 CDR-L1

<400> SEQUENCE: 22

Arg Ala Ser Glu Asn Ile Asp Thr Tyr Leu His
1 5 10

<210> SEQ ID NO 23
<211> LENGTH: 7
<212> TYPE: PRT
<213> ORGANISM: Artificial
<220> FEATURE:
<223> OTHER INFORMATION: EIG B 10D9 CDR-L2

<400> SEQUENCE: 23

Phe Ala Ser Gln Ser Ile Ser
1 5

<210> SEQ ID NO 24
<211> LENGTH: 9
<212> TYPE: PRT
<213> ORGANISM: Artificial
<220> FEATURE:
<223> OTHER INFORMATION: EIG B 10D9 CDR-L3

<400> SEQUENCE: 24

Gln Gln Gly Asn Ile Leu Pro Tyr Thr
1 5

<210> SEQ ID NO 25
<211> LENGTH: 5
<212> TYPE: PRT
<213> ORGANISM: Artificial
<220> FEATURE:
<223> OTHER INFORMATION: EIG D 26D7 CDR-H1

<400> SEQUENCE: 25

Ser Tyr Trp Met Asp
1 5

<210> SEQ ID NO 26
<211> LENGTH: 17
<212> TYPE: PRT
<213> ORGANISM: Artificial
<220> FEATURE:
<223> OTHER INFORMATION: EIG D 26D7 CDR-H2

<400> SEQUENCE: 26

Asn Ile Tyr Pro Ser Asp Gly Glu Thr His Tyr Asn Gln Lys Phe Lys
1 5 10 15

Asp

<210> SEQ ID NO 27
<211> LENGTH: 7
<212> TYPE: PRT
<213> ORGANISM: Artificial
<220> FEATURE:
<223> OTHER INFORMATION: EIG D 26D7 CDR-H3

<400> SEQUENCE: 27

Leu Tyr Ser Glu Tyr Gly Ser
1 5

<210> SEQ ID NO 28
<211> LENGTH: 17
<212> TYPE: PRT
<213> ORGANISM: Artificial
<220> FEATURE:
<223> OTHER INFORMATION: EIG D 26D7 CDR-L1

<400> SEQUENCE: 28

Lys Ser Ser Gln Ser Leu Leu Asn Ser Gly Asn Gln Lys Asn Tyr Leu
1 5 10 15

Thr

<210> SEQ ID NO 29
<211> LENGTH: 7
<212> TYPE: PRT
<213> ORGANISM: Artificial
<220> FEATURE:
<223> OTHER INFORMATION: EIG D 26D7 CDR-L2

<400> SEQUENCE: 29

Trp Ala Ser Thr Arg Asp Ser
1 5

<210> SEQ ID NO 30
<211> LENGTH: 9
<212> TYPE: PRT
<213> ORGANISM: Artificial
<220> FEATURE:
<223> OTHER INFORMATION: EIG D 26D7 CDR-L3

<400> SEQUENCE: 30

Gln Asn Asp Tyr Ser Tyr Pro Leu Thr
1 5

<210> SEQ ID NO 31
<211> LENGTH: 111
<212> TYPE: PRT
<213> ORGANISM: Artificial
<220> FEATURE:
<223> OTHER INFORMATION: EIG B 18B2 heavy chain variable region

<400> SEQUENCE: 31

-continued

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Ile Ser Trp Val Arg Gln Pro Pro Gly Lys Gly Leu Glu Trp Ile
        35                  40                  45

Ala Ala Ile Ser Ser Gly Gly Asp Thr Tyr Tyr Asn Ser Leu Leu Lys
    50                  55                  60

Ser Arg Leu Ser Ile Ser Arg Asp Thr Ser Lys Ser Gln Val Phe Leu
65                  70                  75                  80

Lys Met Asn Arg Leu Gln Thr Glu Asp Thr Ala Phe Tyr Phe Cys Asn
                85                  90                  95

Gly Glu Ser Tyr Trp Gly Gln Gly Thr Leu Val Thr Val Ser Ser
            100                 105                 110


<210> SEQ ID NO 32
<211> LENGTH: 109
<212> TYPE: PRT
<213> ORGANISM: Artificial
<220> FEATURE:
<223> OTHER INFORMATION: EIG B 18B2 light chain variable region

<400> SEQUENCE: 32

Asp Val Val Leu Thr Gln Ser Pro Ala Thr Leu Ser Val Thr Pro Gly
1               5                   10                  15

Glu Arg Ile Ser Leu Ser Cys Arg Ala Ser Glu Asn Ile Asp Thr Tyr
            20                  25                  30

Leu His Trp Phe Gln Gln Lys Pro Asn Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Arg Asp Phe Thr Leu Ser Ile Asn Gly Val Glu Leu
65                  70                  75                  80

Glu Asp Leu Ser Ile Tyr Tyr Cys Gln Gln Gly Asn Ile Leu Pro Tyr
                85                  90                  95

Thr Phe Gly Ala Gly Thr Arg Leu Glu Leu Lys Arg Ala
            100                 105


<210> SEQ ID NO 33
<211> LENGTH: 111
<212> TYPE: PRT
<213> ORGANISM: Artificial
<220> FEATURE:
<223> OTHER INFORMATION: EIG B 10D9 heavy chain variable region

<400> SEQUENCE: 33

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Ile Ser Trp Val Arg Gln Pro Pro Gly Lys Gly Leu Glu Trp Ile
        35                  40                  45

Ala Ala Ile Ser Ser Gly Gly Asp Thr Tyr Tyr Asn Ser Leu Leu Lys
    50                  55                  60

Ser Arg Leu Ser Ile Ser Arg Asp Thr Ser Lys Ser Gln Val Phe Leu
65                  70                  75                  80

Lys Met Asn Arg Leu Gln Thr Glu Asp Thr Ala Phe Tyr Phe Cys Asn
                85                  90                  95
```

-continued

```
Gly Glu Ser Tyr Trp Gly Gln Gly Thr Leu Val Thr Val Ser Ser
            100                 105                 110


<210> SEQ ID NO 34
<211> LENGTH: 109
<212> TYPE: PRT
<213> ORGANISM: Artificial
<220> FEATURE:
<223> OTHER INFORMATION: EIG B 10D9 light chain variable region

<400> SEQUENCE: 34

Asp Val Val Leu Thr Gln Ser Pro Ala Thr Leu Ser Val Thr Pro Gly
1               5                   10                  15

Glu Arg Ile Ser Leu Ser Cys Arg Ala Ser Glu Asn Ile Asp Thr Tyr
            20                  25                  30

Leu His Trp Phe Gln Gln Lys Pro Asn Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Gly Val Glu Leu
65                  70                  75                  80

Glu Asp Leu Ser Ile Tyr Tyr Cys Gln Gln Gly Asn Ile Leu Pro Tyr
                85                  90                  95

Thr Phe Gly Ala Gly Thr Lys Leu Glu Leu Lys Arg Ala
            100                 105


<210> SEQ ID NO 35
<211> LENGTH: 116
<212> TYPE: PRT
<213> ORGANISM: Artificial
<220> FEATURE:
<223> OTHER INFORMATION: EIG D 26D7 heavy chain variable region

<400> SEQUENCE: 35

Gln Val Gln Leu Gln Gln Pro Gly Ala Asp Leu Val Arg Pro Gly Ser
1               5                   10                  15

Ser Val Lys Leu Ser Cys Lys Ala Ser Gly Tyr Ser Phe Thr Ser Tyr
            20                  25                  30

Trp Met Asp Trp Val Lys Gln Arg Pro Gly Gln Gly Leu Glu Trp Ile
        35                  40                  45

Gly Asn Ile Tyr Pro Ser Asp Gly Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Tyr Ser Glu Tyr Gly Ser Trp Gly Gln Gly Thr Thr Leu
            100                 105                 110

Thr Val Ser Ser
        115


<210> SEQ ID NO 36
<211> LENGTH: 115
<212> TYPE: PRT
<213> ORGANISM: Artificial
<220> FEATURE:
<223> OTHER INFORMATION: EIG D 26D7 light chain variable region

<400> SEQUENCE: 36
```

-continued

```
Asp Ile Val Met Thr Gln Ser Pro Ser Ser Leu Thr Val Thr Thr Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Arg Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Ala Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg Ala
        115


<210> SEQ ID NO 37
<211> LENGTH: 166
<212> TYPE: PRT
<213> ORGANISM: Artificial
<220> FEATURE:
<223> OTHER INFORMATION: EIG B 18B2 heavy chain

<400> SEQUENCE: 37

Met Ala Val Leu Val Leu Leu Leu Cys Leu Val Thr Tyr Pro Ile Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Ser Tyr His Ile Ser Trp Val Arg Gln Pro Pro Gly Lys Gly Leu
    50                  55                  60

Glu Trp Ile Ala Ala Ile Ser Ser Gly Gly Asp Thr Tyr Tyr Asn Ser
65                  70                  75                  80

Leu Leu Lys Ser Arg Leu Ser Ile Ser Arg Asp Thr Ser Lys Ser Gln
                85                  90                  95

Val Phe Leu Lys Met Asn Arg Leu Gln Thr Glu Asp Thr Ala Phe Tyr
            100                 105                 110

Phe Cys Asn Gly Glu Ser Tyr Trp Gly Gln Gly Thr Leu Val Thr Val
        115                 120                 125

Ser Ser Ala Arg Thr Thr Ala Pro Ser Val Tyr Pro Leu Val Pro Gly
    130                 135                 140

Cys Ser Gly Thr Ser Gly Ser Leu Val Thr Leu Gly Cys Leu Val Lys
145                 150                 155                 160

Gly Leu Tyr Pro Glu Pro
                165


<210> SEQ ID NO 38
<211> LENGTH: 221
<212> TYPE: PRT
<213> ORGANISM: Artificial
<220> FEATURE:
<223> OTHER INFORMATION: EIG B 18B2 light chain

<400> SEQUENCE: 38

Met Val Phe Ile Pro Gln Phe Phe Val Met Leu Leu Phe Trp Ile Ser
1               5                   10                  15
```

```
Asp Ser Lys Gly Asp Val Val Leu Thr Gln Ser Pro Ala Thr Leu Ser
            20                  25                  30

Val Thr Pro Gly Glu Arg Ile Ser Leu Ser Cys Arg Ala Ser Glu Asn
        35                  40                  45

Ile Asp Thr Tyr Leu His Trp Phe Gln Gln Lys Pro Asn Glu Ser Pro
    50                  55                  60

Arg Leu Leu Ile Lys Phe Ala Ser Gln Ser Ile Ser Gly Ile Pro Ser
65                  70                  75                  80

Arg Phe Ser Gly Ser Gly Ser Gly Arg Asp Phe Thr Leu Ser Ile Asn
                85                  90                  95

Gly Val Glu Leu Glu Asp Leu Ser Ile Tyr Tyr Cys Gln Gln Gly Asn
            100                 105                 110

Ile Leu Pro Tyr Thr Phe Gly Ala Gly Thr Arg Leu Glu Leu Lys Arg
        115                 120                 125

Ala Asp Ala Ala Pro Thr Val Ser Ile Phe Pro Pro Ser Thr Glu Gln
    130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Ala Asp Tyr Glu Ser
        195                 200                 205

His Asn Leu Tyr Thr Cys Glu Val Phe Ile Arg Leu Ser
    210                 215                 220


<210> SEQ ID NO 39
<211> LENGTH: 166
<212> TYPE: PRT
<213> ORGANISM: Artificial
<220> FEATURE:
<223> OTHER INFORMATION: EIG B 10D9 heavy chain

<400> SEQUENCE: 39

Met Ala Val Leu Val Leu Leu Leu Cys Leu Val Thr Tyr Pro Ser Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Ser Tyr His Ile Ser Trp Val Arg Gln Pro Pro Gly Lys Gly Leu
    50                  55                  60

Glu Trp Ile Ala Ala Ile Ser Ser Gly Gly Asp Thr Tyr Tyr Asn Ser
65                  70                  75                  80

Leu Leu Lys Ser Arg Leu Ser Ile Ser Arg Asp Thr Ser Lys Ser Gln
                85                  90                  95

Val Phe Leu Lys Met Asn Arg Leu Gln Thr Glu Asp Thr Ala Phe Tyr
            100                 105                 110

Phe Cys Asn Gly Glu Ser Tyr Trp Gly Gln Gly Thr Leu Val Thr Val
        115                 120                 125

Ser Ser Ala Arg Thr Thr Ala Pro Ser Val Tyr Pro Leu Val Pro Gly
    130                 135                 140

Cys Ser Gly Thr Ser Gly Ser Leu Val Thr Leu Gly Cys Leu Val Lys
145                 150                 155                 160
```

Gly His Tyr Gln Ile Pro
165

<210> SEQ ID NO 40
<211> LENGTH: 145
<212> TYPE: PRT
<213> ORGANISM: Artificial
<220> FEATURE:
<223> OTHER INFORMATION: EIG B 10D9 light chain

<400> SEQUENCE: 40

Met Val Phe Ile Pro Gln Phe Phe Val Met Leu Leu Phe Trp Ile Ser
1 5 10 15

Asp Ser Lys Gly Asp Val Val Leu Thr Gln Ser Pro Ala Thr Leu Ser
20 25 30

Val Thr Pro Gly Glu Arg Ile Ser Leu Ser Cys Arg Ala Ser Glu Asn
35 40 45

Ile Asp Thr Tyr Leu His Trp Phe Gln Gln Lys Pro Asn Glu Ser Pro
50 55 60

Arg Leu Leu Ile Lys Phe Ala Ser Gln Ser Ile Ser Gly Ile Pro Ser
65 70 75 80

Arg Phe Ser Gly Ser Gly Ser Gly Thr Asp Phe Thr Leu Ser Ile Asn
85 90 95

Gly Val Glu Leu Glu Asp Leu Ser Ile Tyr Tyr Cys Gln Gln Gly Asn
100 105 110

Ile Leu Pro Tyr Thr Phe Gly Ala Gly Thr Lys Leu Glu Leu Lys Arg
115 120 125

Ala Asp Ala Ala Pro Thr Val Ser Ile Phe Pro Pro Ser Thr Lys Gly
130 135 140

Arg
145

<210> SEQ ID NO 41
<211> LENGTH: 252
<212> TYPE: PRT
<213> ORGANISM: Artificial
<220> FEATURE:
<223> OTHER INFORMATION: EIG D 26D7 heavy chain

<400> SEQUENCE: 41

Phe Phe Tyr Trp Gly Gly Gly Gly Gly Gly Gly Ser Ile Arg Ser Leu
1 5 10 15

Phe Ser Leu Gln Leu Leu Ser Thr Gln Asp Leu Thr Met Gly Trp Ser
20 25 30

Cys Ile Ile Leu Phe Leu Val Ala Thr Ala Thr Gly Val His Ser Gln
35 40 45

Val Gln Leu Gln Gln Pro Gly Ala Asp Leu Val Arg Pro Gly Ser Ser
50 55 60

Val Lys Leu Ser Cys Lys Ala Ser Gly Tyr Ser Phe Thr Ser Tyr Trp
65 70 75 80

Met Asp Trp Val Lys Gln Arg Pro Gly Gln Gly Leu Glu Trp Ile Gly
85 90 95

Asn Ile Tyr Pro Ser Asp Gly Glu Thr His Tyr Asn Gln Lys Phe Lys
100 105 110

Asp Lys Ala Thr Leu Thr Val Asp Lys Ser Ser Ser Thr Ala Tyr Met
115 120 125

Gln Leu Ser Ser Leu Thr Ser Glu Asp Ser Ala Val Tyr Tyr Cys Ala

-continued

```
    130                 135                 140

Arg Leu Tyr Ser Glu Tyr Gly Ser Trp Gly Gln Gly Thr Thr Leu Thr
145                 150                 155                 160

Val Ser Ser Ala Lys Thr Thr Pro Pro Ser Val Tyr Pro Leu Ala Pro
                165                 170                 175

Gly Cys Gly Asp Thr Thr Gly Ser Ser Val Thr Leu Gly Cys Leu Val
            180                 185                 190

Lys Gly Tyr Phe Pro Glu Ser Val Thr Val Thr Trp Asn Ser Gly Ser
        195                 200                 205

Leu Ser Ser Ser Val His Thr Phe Pro Ala Leu Leu Gln Ser Gly Leu
    210                 215                 220

Tyr Thr Met Ser Ser Ser Val Thr Val Pro Ser Ser Thr Trp Pro Ser
225                 230                 235                 240

Gln Thr Val Thr Leu Gln Arg Cys Pro Gln His Gln
                245                 250


<210> SEQ ID NO 42
<211> LENGTH: 173
<212> TYPE: PRT
<213> ORGANISM: Artificial
<220> FEATURE:
<223> OTHER INFORMATION: EIG D 26D7 light chain

<400> SEQUENCE: 42

Phe Pro Pro Ala Leu Lys Gly Gly Gly Gly Gly Gly Asp Leu His Leu
1               5                   10                  15

Lys Gly Arg Trp Ser Lys Met Glu Ser Gln Thr Gln Val Leu Met Ser
            20                  25                  30

Leu Leu Phe Trp Val Ser Gly Thr Cys Gly Asp Ile Val Met Thr Gln
        35                  40                  45

Ser Pro Ser Ser Leu Thr Val Thr Thr Gly Glu Lys Val Thr Met Ser
    50                  55                  60

Cys Lys Ser Ser Gln Ser Leu Leu Asn Ser Gly Asn Gln Lys Asn Tyr
65                  70                  75                  80

Leu Thr Trp Tyr Gln Gln Arg Pro Gly Gln Pro Pro Lys Leu Leu Ile
                85                  90                  95

Tyr Trp Ala Ser Thr Arg Asp Ser Gly Val Pro Asp Arg Phe Thr Gly
            100                 105                 110

Ser Gly Ser Gly Thr Asp Phe Thr Leu Thr Ile Ser Ser Val Gln Ala
        115                 120                 125

Ala Asp Leu Ala Val Tyr Tyr Cys Gln Asn Asp Tyr Ser Tyr Pro Leu
    130                 135                 140

Thr Phe Gly Ala Gly Thr Lys Leu Glu Leu Lys Arg Ala Asp Ala Ala
145                 150                 155                 160

Pro Thr Val Ser Ile Phe Pro Pro Ser Gln Ser Phe Pro
                165                 170
```